United States Patent
Parker et al.

(10) Patent No.: US 10,203,268 B2
(45) Date of Patent: Feb. 12, 2019

(54) METHODS FOR MEASURING AND MODELING THE PROCESS OF PRESTRESSING CONCRETE DURING TENSIONING/DETENSIONING BASED ON ELECTRONIC DISTANCE MEASUREMENTS

(71) Applicant: Sophie Lin, Charlottesville, VA (US)

(72) Inventors: David H. Parker, Earlysville, VA (US); John M. Payne, Charlottesville, VA (US)

(73) Assignees: Laura P. Solliday, Green Bank, WV (US); Sophie Lin, Charlottesville, VA (US), Trustee of the John Michael Payne Family Trust ( * ) Notice: Subject to any disclaimer, the term of this patent is extended or adjusted under 35 U.S.C. 154(b) by 377 days.

(21) Appl. No.: 15/165,563

(22) Filed: May 26, 2016

(65) Prior Publication Data
US 2016/0274001 A1    Sep. 22, 2016

(51) Int. Cl.
*G01M 99/00* (2011.01)
*G01B 11/00* (2006.01)
(Continued)

(52) U.S. Cl.
CPC ......... *G01M 99/007* (2013.01); *G01B 11/002* (2013.01); *G01B 11/03* (2013.01);
(Continued)

(58) Field of Classification Search
CPC .... G01M 99/007; G01B 11/002; G01B 11/03; G01B 11/14; G01B 11/16; G01C 15/002;
(Continued)

(56) References Cited

U.S. PATENT DOCUMENTS 611,907 A    10/1898   Hennebique
2,826,800 A   3/1958   Buren
(Continued)

OTHER PUBLICATIONS

Lun et al., "Design and Construction Aspects of Post-Tensioned LNG Storage Tanks in Europe and Australasia", 2006, The New Zealand Concrete Industry Conference, Christchurch, 2006.*
(Continued)

*Primary Examiner* — Regis Betsch
(74) *Attorney, Agent, or Firm* — David H. Parker

(57) ABSTRACT

Methods are disclosed for nondestructive testing and measuring the structural health of prestressed concrete structures, such as slabs, columns, girders, bridges, towers, elevated storage tanks, silos, cooling towers, wind power generation towers, liquefied gas storage tanks, nuclear power containment buildings, and the like. Measurements are made as the structure undergoes tensioning and detensioning operations. By measuring actual movements of cardinal points on the structure, in an absolute three-dimensional coordinate system, and comparing the measurements to a model—as tension on a tendon is changed—a margin of safety is assured. High accuracy measurements are made by electronic distance measurement (EDM) instruments over hundreds of meters, which yield coordinates of cardinal points with an uncertainty of the order of one part per million. The methods are proposed as possible alternatives to prior failures of post-tensioned concrete, including the Las Lomas Bridge, the Kapiolani Interchange On-Ramp, Turkey Point Unit 3 Nuclear Power Plant, and Crystal River Unit 3 Nuclear Power Plant. An extensive review of the most closely related prior arts is included.

5 Claims, 16 Drawing Sheets

(51) Int. Cl.
  *G06F 17/50* (2006.01)
  *G01B 11/03* (2006.01)
  *G01B 11/14* (2006.01)
  *G01B 11/16* (2006.01)
  *G01C 15/00* (2006.01)
  *G01N 33/38* (2006.01)

(52) U.S. Cl.
  CPC ............ *G01B 11/14* (2013.01); *G01B 11/16* (2013.01); *G01C 15/002* (2013.01); *G01N 33/383* (2013.01); *G06F 17/5004* (2013.01); *G06F 17/5018* (2013.01)

(58) Field of Classification Search
  CPC ............ G06F 17/5018; G06F 17/5004; G01N 33/383
  See application file for complete search history.

(56) References Cited

U.S. PATENT DOCUMENTS

| | | |
|---|---|---|
| 3,633,328 A | 1/1972 | Closner |
| 3,865,688 A | 2/1975 | Kleimola |
| 4,041,722 A | 8/1977 | Terlesky |
| 4,045,289 A | 8/1977 | Seidensticker |
| 4,050,983 A | 9/1977 | Kleimola |
| 4,080,256 A | 3/1978 | Braun |
| 4,091,583 A | 5/1978 | Genis |
| 4,092,811 A | 6/1978 | Lin |
| 4,113,381 A | 9/1978 | Epstein |
| 4,128,011 A | 12/1978 | Savage |
| 4,175,005 A | 11/1979 | Harstead |
| 4,265,066 A | 5/1981 | Lin |
| 4,409,842 A | 10/1983 | Scott |
| 4,457,625 A | 7/1984 | Greenleaf |
| 4,473,528 A | 9/1984 | Kleimola |
| 4,480,480 A | 11/1984 | Scott |
| 4,549,437 A | 10/1985 | Weins |
| 4,574,545 A | 3/1986 | Reigstad |
| 4,621,926 A | 11/1986 | Merry |
| 4,691,446 A | 9/1987 | Pitches |
| 4,714,339 A | 12/1987 | Lau |
| 4,790,651 A | 12/1988 | Brown |
| 4,805,540 A | 2/1989 | Mundloch |
| 4,927,596 A | 5/1990 | Minnick |
| 5,076,173 A | 12/1991 | Baker |
| 5,180,969 A | 1/1993 | Kwun |
| 5,195,046 A | 3/1993 | Gerardi |
| 5,351,625 A | 10/1994 | Culligan |
| 5,455,670 A | 10/1995 | Payne |
| 5,467,719 A | 11/1995 | Dalrymple |
| 5,633,467 A | 5/1997 | Paulson |
| 5,657,003 A | 8/1997 | Fuentes |
| 5,764,360 A | 6/1998 | Meier |
| 5,814,731 A | 9/1998 | Alexander |
| 5,841,353 A | 11/1998 | Chisholm |
| 5,850,185 A | 12/1998 | Canty |
| 5,948,984 A | 9/1999 | Hedberg |
| 6,006,163 A | 12/1999 | Lichtenwalner |
| 6,119,526 A | 9/2000 | Reigstad |
| 6,192,758 B1 | 2/2001 | Huang |
| 6,240,783 B1 | 6/2001 | Mcgugin |
| 6,246,468 B1 | 6/2001 | Dimsdale |
| 6,257,064 B1 | 7/2001 | Duron |
| 6,357,363 B1 | 3/2002 | Miltaru |
| 6,412,348 B1 | 7/2002 | Iemura |
| 6,484,381 B2 | 11/2002 | Cunningham |
| 6,501,550 B1 | 12/2002 | Mihaljov |
| 6,581,466 B1 | 6/2003 | Costley |
| 6,597,973 B1 | 7/2003 | Barich |
| 6,598,480 B2 | 7/2003 | Horiuchi |
| 6,637,266 B1 | 10/2003 | Froom |
| 6,718,270 B2 | 4/2004 | Horiuchi |
| 6,751,821 B1 | 6/2004 | Han |
| 6,757,620 B1 | 6/2004 | Yoon |
| 6,779,404 B1 | 8/2004 | Brincker |
| 6,832,183 B1 | 12/2004 | Barich |
| 6,915,217 B2 | 7/2005 | Springer |
| 6,944,550 B2 | 9/2005 | Marchetti |
| 6,955,100 B1 | 10/2005 | Barich |
| 6,989,890 B2 | 1/2006 | Riegl |
| 7,006,947 B2 | 2/2006 | Tryon |
| 7,024,343 B2 | 4/2006 | El-ratal |
| 7,101,053 B2 | 9/2006 | Parker |
| 7,180,072 B2 | 2/2007 | Persi |
| 7,190,465 B2 | 3/2007 | Froehlich |
| 7,193,690 B2 | 3/2007 | Ossig |
| 7,194,326 B2 | 3/2007 | Cobb |
| 7,199,872 B2 | 4/2007 | Van Cranenbroeck |
| 7,228,240 B2 | 6/2007 | Duron |
| 7,352,446 B2 | 4/2008 | Bridges |
| 7,358,516 B2 | 4/2008 | Holler |
| 7,403,268 B2 | 7/2008 | England |
| 7,512,500 B2 | 3/2009 | Wilt |
| 7,546,224 B2 * | 6/2009 | Campbell .............. G05B 17/02 702/33 |
| 7,580,800 B1 | 8/2009 | Winter |
| 7,584,075 B2 | 9/2009 | Kim |
| 7,596,470 B2 | 9/2009 | Kim |
| 7,623,974 B2 | 11/2009 | Cipra |
| 7,637,166 B2 | 12/2009 | Hecht |
| 7,647,206 B2 | 1/2010 | Ford |
| 7,667,827 B2 | 2/2010 | Nelson |
| 7,668,692 B2 | 2/2010 | Tatom |
| 7,672,793 B2 | 3/2010 | Beard |
| 7,672,817 B2 | 3/2010 | Marsh |
| 7,681,468 B2 | 3/2010 | Verl |
| 7,739,843 B2 | 6/2010 | Cortina-cordero |
| 7,756,321 B2 | 7/2010 | Marsh |
| 7,787,979 B2 | 8/2010 | Marsh |
| 7,800,758 B1 | 9/2010 | Bridges |
| RE41,877 E | 10/2010 | Parker |
| 7,806,058 B2 | 10/2010 | Saxton |
| 7,819,008 B2 | 10/2010 | Winter |
| 7,856,334 B2 | 12/2010 | Parker |
| 7,895,015 B2 * | 2/2011 | Parker .................... G01B 11/03 250/203.2 |
| 7,957,825 B2 | 6/2011 | Marsh |
| 7,975,622 B2 | 7/2011 | Dalrymple |
| 7,978,322 B2 | 7/2011 | Marsh |
| 7,996,998 B2 | 8/2011 | Nakaniwa |
| 8,091,432 B2 | 1/2012 | Hecht |
| 8,176,800 B2 | 5/2012 | Cesare |
| 8,209,134 B2 * | 6/2012 | Parker .................... G01B 11/03 250/203.2 |
| 8,220,212 B2 | 7/2012 | Stiesdal |
| 8,285,495 B2 | 10/2012 | Purekar |
| 8,510,061 B2 | 8/2013 | Grant |
| 8,688,408 B2 | 4/2014 | Marsh |
| 8,706,428 B1 | 4/2014 | Righi |
| 8,830,477 B2 | 9/2014 | Schreiber |
| 8,919,074 B2 | 12/2014 | Meyer |
| 8,953,153 B2 | 2/2015 | Wall |
| 9,354,043 B2 * | 5/2016 | Parker ...................... E04B 1/00 |
| 2004/0035218 A1 | 2/2004 | Paulson |
| 2006/0248954 A1 | 11/2006 | Snieder |
| 2008/0059086 A1 | 3/2008 | Duron |
| 2009/0171619 A1 | 7/2009 | Van Cranenbroeck |
| 2010/0154318 A1 | 6/2010 | Shockley |
| 2010/0179771 A1 | 7/2010 | Shim |
| 2010/0238027 A1 | 9/2010 | Bastianini |
| 2011/0029276 A1 | 2/2011 | Cabral Martin |
| 2012/0123981 A1 | 5/2012 | Graves |
| 2015/0254376 A1 | 9/2015 | Pettersson |
| 2015/0316649 A1 | 11/2015 | Marsh |

OTHER PUBLICATIONS

Kansas Department of Transportation, Post-tensioned Concrete Haunched Slab Bridges—Design and Construction, Feb. 2013.*
Saouma et al., "Statistical and 3D Nonlinear Finite Element Analysis of Schlegeis Dam" 2001.*

(56) References Cited

OTHER PUBLICATIONS

Boavida et al., "Dam monitoring using combined terrestrial imaging systems", 2009, CES Dec./Jan. 2009 pp. 33-38.*
Scott Sandwith et al., "Real-time 5-Micron Uncertainty with Laser Tracker Interferometer System using Weighted Trilateration", 2001 Boeing Large-Scale Metrology Conference, St. Louis, recovered from the internet Sep. 27, 2016, http://www.kinematics.com/images/TrilaterationPaperR1.pdf.
Howard Newlon, Jr. "Twentieth-Century Building Materials: History and Conservation", Chapter 11—Prestresses Concrete, Thomas C. Jester, ed, 2014.
Sanabra-Loewe, et al., "The four ages of early prestressed concrete structures", pp. 93-120, PCI Journal, Fall 2014.
Howard Newlon, Jr., "Prestressed Concrete", Prestressed Concrete Institute, 1981.
"New Directions for Florida Post-Tensioned Bridges, vol. 1 of 10: Post Tensioning in Florida Bridges, 2002", Florida Department of Transportation, 2002.
Kaźmierczak, "Selected issues of prestressed concrete containment tanks for the storage of liquified gases design in accordance with EN 14620", Cracow University of Technology.
Lun et al., "Design and construction aspects of post-tensioned LNG storage tanks in Europe and Australia", The New Zealand Concrete Industry Conference, Christchurch, 2006.
Hjorteset et al., "Development of large-scale precast, prestressed concrete liquified natural gas storage tanks", PCI Journal, Fall 2013.
"Concrete Storage Structures—Use of the VSL Special Construction Methods", VSL International Ltd, 1983.
Dwight Clayton, et al., "Research and Development Roadmaps for Nondestructive Evaluation of Cables, Concrete, Reactor Pressure Vessels, and Piping Fatigue", Proc. SPIE vol. 8694, 2013.
Dwight Clayton, et al., "Summary of Large Concrete Samples", Oak Ridge National Laboratory, ORNL_TM_2013_223, 2013.
Dwight Clayton, et al., "Comparative testing of nondestructive examination techniques for concrete structures", Proc. SPIE vol. 9063, 2014.
Dwight Clayton, et al., "Nondestructive Evaluation of Thick Concrete Using Advanced Signal Processing Techniques", Oak Ridge National Laboratory, ORNL/TM-2015/428, 2015.
Dwight Clayton, "Nondestructive Evaluation of Thick Concrete Structures", Proc. SPIE vol. 9439, 2015.
Dwight Clayton, "Improving Synthetic Aperture Focusing Technique for Thick Concrete Specimens via Frequency Banding", Proc. SPIE 9804, 2016.
Ola Jovall, et al, "Concrete containment management using finite element technique combined with in-situ non-destructive testing of conformity with respect to design and constructive quality (CONMOD)", EU research in reactor safety; FISA 2003.
Klinghoffer, et al., "Condition assessment of concrete structures at nuclear power plants by state of the art non-destructive testing", EPJ Web of Conferences 12, 03002 (2011).
D. J. Naus, "Inspection of Nuclear Power Plant Structures—Overview of Methods and Related Applications", Oak Ridge National Laboratory, ORNL/TM-2007-191, 2009.
Walter Podolny, Jr., "The Cause of Cracking in Post-Tensioned Concrete Box Girder Bridges and Retrofit Procedures", PCI Journal, Mar.-Apr. 1985.
"Florida Power and Light Company, Turkey Point Unit 3, Containment Dome Report", 1970.
"Special Inspection Report 05000302/2009007", Nuclear Regulatory Commission, 2010.
"Crystal River Unit #3 Containment Delamination Update, Nov. 20, 2009", Progress Energy, 2009.
"Crystal River Nuclear Plant—Steam Generator Replacement Inspection Progress Report 05000302/2011009", Nuclear Regulatory Commission, 2011.
Press Release, Duke Energy, Jun. 27, 2011.
"Crystal River Unit 3—NRC Integrated Inspection Report 05000302/2011004" Nuclear Regulatory Commission, 2011.
Report by Zapata Inc to Duke Energy, cover letter to Florida Public Service Commission, table of contents, and executive summary of 994 page report, 2012.
Press Release, Duke Energy, Feb. 5, 2013.
Brinker and Minnick, "The Surveying Handbook", Chapter 5—Linear Measurements: EDM Instruments, 1995.
Brinker and Minnick, "The Surveying Handbook", Chapter 12—Trilateration, 1995.
Bob Marsh, "Metrology Controlling Aircraft Shape Technology", CMSC 2016, recovered from the internet Sep. 17, 2016, https://www.cmsc.org/stuff/contentmgr/files/1/09da31da5ae016f3b8adf908c6c4a013/misc/12_marsh_cmsc_2016_presentation.pdf.
Michael Lazar, "Photogrammetry Measurements of Passenger Entry Doors", Journal of the CMSC, vol. 10, No. 2, Autumn 2015, pp. 22-25.
Bala Muralikrishnan, et al., "Laser trackers for large-scale dimensional metrology: A review", Precision Engineering 44 (2016) 13-28.
Etalon product literature, "Absolute Multiline Technology", 2014.
Boavida et al., Dam Monitoring Using Combined Terrestrial Imaging Systems, May 2008, 13th Symposium of Deformation Measurement and Analysis.
Burge et al., "Use of a commercial laser tracker for optical alignment", Sep. 2007, Optical System Alignment and Tolerancing, SPIE vol. 6676.
Saouma et al. "Statistical and 3D nonlinear finite element analysis of Schlegeis Dam", 2003, online http://civil.colorado.edu/~balajir/my-papers/souma-rajagopalan.pdf.
Verification of High-Accuracy and contact measurement system using FSF Laser Optical Coordinate, Nov. 2007, 3rd INtl. Conf. on Struct. Health Monitoring.
Benedikt Weber, "Rational Transmitting Boundaries for Time-Domain Analysis of Dam-Reservoir Interaction", 1994, vol. 205 of the series Institut für Baustatik and Konstruktion pp. 1-14.
B. T. Wand, et al., "A single beam laser tracker as an alignment tool", SLAC-PUB-5847, Stanford, CA, 1992.
G. Gassner, et al., "Instrument tests with the new Leica AT401, SLAC-PUB-14300", Stanford, CA, 2011.
Public Law 108-426, 118 STAT. 2423-2429, 2004.
Osha Instruction Pub 8-1.5, Washington, DC, 1989.
"Inspecting rail tank cars", Inspection Trends, p. 15-17, summer 2007.
Federal hazmat law-an overview, US DOT Pipeline and Hazardous Materials Safety Administration, Washington, DC, 2008.
Virginia Tech, "Guidelines for the operation, assembly, repair, testing and inspection of hazardous material cargo tanks", US DOT Federal Motor Carrier Safety Administration, Washington, DC, 2009.
"Facts about propane", National Propane Gas Association, 2001.
"Railroad tank car nondestructive methods evaluation", DOT/FRA/ORD-01104, US DOT Federal Railroad Administration, Washington, Dc, 2004.
"ASME boiler and pressure vessel code", vol. V, table of contents, ASME 2007.
"Crashworthiness protection requirements for tank cars; detection and repair of cracks, pits, corrosion, lining flaws, thermal protection flaws and other defects of tank car tanks", US DOT Research and Special Programs Administration, 60 FR 49048-49083, 1995.
"Detection and repair of cracks, pits, corrosion, lining flaws, thermal protection flaws, and other defects of tank car tanks", US DOT Research and Special Programs Administration, 52 FR 46510-46511, 1987.
"Hazardous materials: improving the safety of railroad tank car transportation of hazardous materials", US DOT Pipeline and Hazardous Materials Safety Administration, 74 FR 1770-1802, 2009.
"Possible cause of reactor building explosion", All Things Nuclear, 2011.
Frank Von Ripple, "Second Chances: containment of a reactor meltdown", Bulletin of the Atomic Scientists, 2011.

(56) References Cited

OTHER PUBLICATIONS

"Five year strategic plan for railroad research, development, and demonstrations"; Section 4.8 hazardous materials transportation, US DOT Federal Railroad Administration, Washington, DC, 2002.
"Ten years of incident reports underscore human error as primary cause of accidents", p. 10-15, National Board Bulletin, 2002.
"Proposed Rule: Railroad tank car safety standards", US DOT Federal Railroad Administration, Washington, DC, 2008.
Frank Von Hippel, "From the Bulletin Archives: Containment of a reactor meltdown", reprint of 1982 article, Bulletin of the Atomic Scientists, 2011.
"Electronic total station speeds survey operations", Hewlett-Packard Journal, Apr. 1976.
"A fully integrated, microprocessor-controlled total station", Hewlett-Packard Journal, vol. 31, No. 9, 1980.
"Electronic distance measurement for industrial and scientific applications", Hewlett-Packard Journal, vol. 31, No. 6, 1980.
"Rupture of a railroad tank car containing hazardous waste, Freeport, Texas, Sep. 13, 2002", NTSB/HZM-04/02, National Transportation Safety Board, Washington, DC, 2004.
"Rupture of a railroad tank car containing hazardous waste near Clymers, Indiana, Feb. 18, 1999", NTSB/HZM-01/01, National Transportation Safety Board, Washington, DC, 2001.
"DOT requires stronger railroad hazmat tank cars to improve crashworthiness", DOT 05-09, USDOT Office of Public Affairs, Washington, DC, 2009.
"Derailment of Canadian Pacific Railway freight train 292-16 and subsequent release of anhydrous ammonia near Minot, North Dakota, Jan. 18, 2002", NTSB/RAR-04/01, National Transportation Safety Board, Washington, DC, 2004.
"Collision of Union Pacific Railroad train MHOTU-23 with BNSF Railway Company train MEAP-TUL-126-D with subsequent derailment and hazardous materials release, Macdona, Texas Jun. 28, 2004", NTSB/RAR-06103, National Transportation Safety Board, Washington, DC, 2006.
"Collision of Norfolk Southern freight train 192 with standing Norfolk Southern local train P22 with subsequent hazardous materials release at Graniteville, South Carolina, Jan. 6, 2005", NTSB/RAR-05/04, National Transportation Safety Board, Washington, DC, 2005.
"Editor's Desk: the first total station?", Professional Surveyor Magazine, Apr. 2002.
New tracker "X" targets 3-D measurement extremes, FARO, 2006.
"Detection and repair of cracks, pits, corrosion, lining flaws and other defects of tank car tanks", 58 FR 48485-48501, US DOT Research and Special Programs Administration, Washington, DC, 1993.
Robert Ruland, "The Chesapeake Laser Tracker in industrial metrology", Proc. Third Int. Workshop on accelerator alignment, p. I/101-118, Annecy, 1993.
Ryuhei Sugahara, et al., "Performance test of a laser tracker", Smart 310, p. III/261-269, Proc. 4th. International Workshop on Accelerator Alignment (IWAA 1995), Tsukuba, Japan, 1995.
"Aloha Airlines, Flight 243 Boeing 737-200, N73711, near Maui, Hawaii, Apr. 28, 1988", NTSB/AAR-89/03, National Transportation Safety Board, Washington, DC, 1989.
US 7,276,718, Holler (withdrawn).
The Surveying Handbook, Brinker and Minnick, section 5-11 "Total-Station Instruments", pp. 77-79, second edition, Chapman & Hall, 1995.
Electronic Distance Measurement, J. M. Rueger, Chapter 1 "History", pp. 1-2, third edition, Springer-Verlag, 1990.
"Nuclear Power Plants, World-Wide", European Nuclear Society, 2012.
Appendix J to Part 50-Primary Reactor Containment Leakage Testing for Water-Cooled Power Reactors, US Nuclear Regulatory Commission, 2012.
Hewlett Packard 1971 catalog supplement, "Laser Interferometer Model 5525A", p. 31.
Assessment and Management of Ageing of Major Nuclear Power Plant Components Important to Safety: Concrete Containment Buildings, IAEA-TECDOC-1025, International Atomic Energy Agency, Vienna, 1998.
Overpressurization Test of 1:4 Scale Prestressed Concrete Containment Vessel Model, NUREG/CR-6810, SAND2003-0840P, Sandia National Laboratories, Albuquerque, 2003.
Demonstrating Structural Adequacy of Nuclear Power Plant Containment Structures for Beyond Design-Basis Pressure Loadings, BNL-91336-2010 CP, Brookhaven National Laboratory, Upton, NY, 2010.
Quantitative Nondestructive Testing of Railroad Tank Cars Using the Probability of Detection Evaluation Approach, DOT/FRA/ORD-09110, Federal Railroad Administration Office of Research and Development, Washington, 2009.
New Regulations on Railroad Bridge Safety: Opportunities and Challenges for Railroad Bridge Monitoring, Fernando Moreu et al., Sensors and Smart Structures Technologies for Civil, Mechanical, and Aerospace Systems 2012, SPIE vol. 8345, paper 834540, May 9, 2012.
Non-Contact Bridge Deflection Measurement: Application of Laser Technology, Upul Attanayake et al., Proceedings of the International Conference Structural Engineering Construction and Management 2011, ICSEM 2011, Peradeniya, Sri Lanka, 2011.
Structural Health Monitoring Method for Curved Concrete Bridge Box Girders, Branko Gli{hacek over (s)}ić, et al., Sensors and Smart Structures Technologies for Civil, Mechanical, and Aerospace Systems 2008, SPIE vol. 6932, paper 693204, 2008.
A. Emin Aktan et al., "Development of a Model Health Monitoring Guide for Major Bridges", Drexel Intelligent Infrastructure and Transportation Safety Institute, Report submitted to Federal Highway Administration Research and Development for contract/order No. DTFH61-01-P-00347, 2003.

* cited by examiner

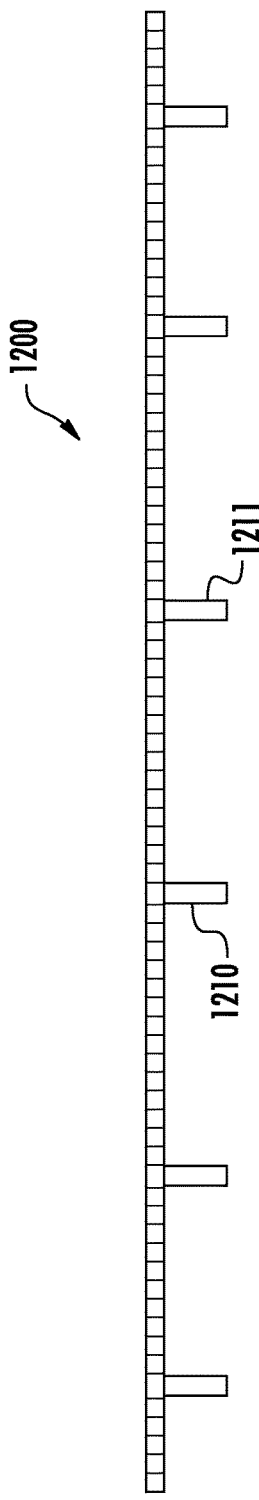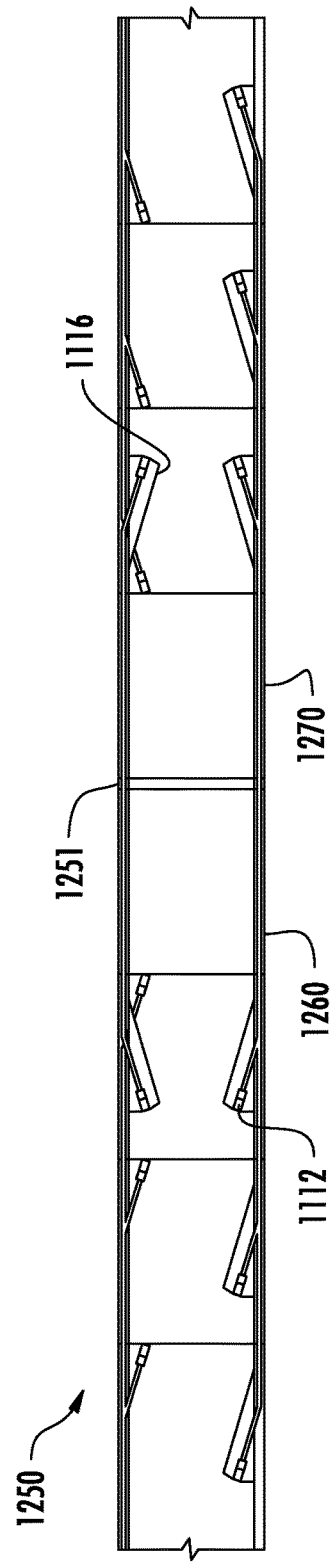
FIG. 12A (PRIOR ART)
FIG. 12B (PRIOR ART)

METHODS FOR MEASURING AND MODELING THE PROCESS OF PRESTRESSING CONCRETE DURING TENSIONING/DETENSIONING BASED ON ELECTRONIC DISTANCE MEASUREMENTS

CROSS-REFERENCE TO RELATED APPLICATIONS

This application is related to U.S. Pat. No. 9,354,043 filed May 31, 2012, which is a continuation-in-part of U.S. Pat. No. 8,209,134 filed Dec. 20, 2010, which is a continuation-in-part of U.S. Pat. No. 7,895,015 filed Dec. 4, 2008, all three of which are incorporated by reference herein.

FIELD OF INVENTION

Methods are disclosed wherein the structural health of prestressed concrete is determined by nondestructive testing during tensioning and detensioning operations, based on electronic distance measurements. Applications include slabs, columns, girders, bridges, towers, elevated storage tanks, silos, cooling towers, wind power generation towers, liquefied gas storage tanks, nuclear power containment buildings, and the like. Electronic distance measurements are also used to verify structural models, such as finite element models.

BACKGROUND OF THE INVENTION

This is the fourth US patent application in an ongoing family of patents related to the use of electronic distance measurements in a triangulation/multilateration architecture for large-scale metrology applications.

U.S. Pat. No. 7,895,015 Method for measuring the structural health of a civil structure, is drawn to methods using trilateration/multilateration for measuring structural health parameters for a bridge, a building, and a crane. U.S. Pat. No. 8,209,134 Methods for modeling the structural health of a civil structure based on electronic distance measurements, is drawn to methods using differences between measurements made by trilateration/multilateration and finite element models, or empirical models, to determine a structural health parameter for a civil structure. U.S. Pat. No. 9,354,043 Methods for measuring and modeling the structural health of pressure vessels based on electronic distance measurements, is drawn to methods using trilateration/multilateration to determine a structural health parameter of a pressure vessel.

This application is drawn to methods using differences between measurements made by trilateration/multilateration and a finite element model of prestressed concrete for the process of tensioning/detensioning the concrete.

This is a pioneering field that brings together heretofore unrelated disciplines of those skilled in the art of high precision electronic distance measurement metrology instrumentation, those skilled in the art of nondestructive testing, those skilled in the art of finite element modeling, and those skilled in the art of large-scale structural engineering. Due to the fact that these disciplines typically belong to non-overlapping professional societies, read different journals and trade magazines, attend different conferences and trade shows, and work in different industries, a large section of the cumulative application is necessary in order to teach the fundamentals and nomenclature of the most closely associated prior arts in order to bring together those unrelated disciplines.

At least part of the motivation for the inventions is drawn from lessons learned from past experiences. A survey of some examples related to each invention is described in the BACKGROUND OF THE INVENTION. The state-of-the art of conventional instrumentation for each discipline is also included.

Historical Overview of Civil Structural Failures

Bridge Failures

On Aug. 1, 2007, the I-35W bridge over the Mississippi River in Minneapolis, Minn. experienced a catastrophic failure. The National Transportation Safety Board (NTSB) concluded in press release SB-08-53, incorporated by reference herein, that the probable cause of the collapse was the inadequate load capacity, due to a design error by Sverdrup & Parcel and Associates, Inc., of the gusset plates at the U10 nodes, which failed under a combination of (1) substantial increases in weight of the bridge, which resulted from previous modifications and (2) the traffic and concentrated construction loads on the bridge on the day of the accident.

On Apr. 1, 1989 the US 51 bridge over the Hatchie River near Covington, Tenn. experienced a catastrophic failure. The NTSB concluded in Highway Accident Report HAR-90-1, incorporated by reference herein, that the probable cause was the northbound migration of the main river channel which the Tennessee Department of Transportation failed to evaluate and correct. Contributing to the severity of the accident was a lack of redundancy in the design of the bridge spans.

On Apr. 5, 1987 the I-90 bridge over the Schoharie Creek near Amsterdam, N.Y., experienced a catastrophic failure. The NTSB concluded in Highway Accident Report HAR-88-02, incorporated by reference herein, that the—probable cause of the collapse of the Schoharie Creek Bridge was the failure of the New York State Thruway Authority to maintain adequate riprap around the bridge piers, which led to severe erosion in the soil beneath the spread footings. Contributing to the accident were ambiguous plans and specifications used for construction of the bridge, an inadequate NYSTA bridge inspection program, and inadequate oversight by the New York State Department of Transportation and the Federal Highway Administration. Contributing to the severity of the accident was a lack of structural redundancy in the bridge.

On Jun. 28, 1983, the I-95E bridge over the Mianus River in Greenwich Conn. experienced a catastrophic failure. The NTSB concluded in Highway Accident Report HAR-84-3, incorporated by reference herein, Sometime before the collapse of the suspended span, the Inside hanger in the southeast corner of the span came off of the inside end of the lower pin. This action shifted the entire weight of the southeast corner of the span onto the outside hanger. The outside hanger gradually worked its way farther outward on the pin, and over a period of time, a fatigue crack developed in the top outside end of the upper pin. The shoulder of the pin fractured off, the pin and hanger assembly failed, and the span collapsed into the river.

On Dec. 15, 1967, the US 35 bridge over the Ohio River in Point Pleasant, W. Va. experienced a catastrophic failure. The NTSB concluded in Highway Accident Report HAR-71-1, incorporated by reference herein, that the cause of the bridge collapse was the cleavage fracture in the lower limb of the eye of eyebar 330 at joint C13N of the north eyebar suspension chain in the Ohio side span. The fracture was caused by the development of a critical size flaw over the 40-year life of the structure as the result of the joint action of stress corrosion and corrosion fatigue.

Other Civil Structural Failures

Catastrophic failures of cranes are much more common than bridges. Investigations are conducted by the U.S. Department of Labor Occupational Safety & Health Administration (OSHA). Unfortunately, the OSHA Accident Investigation Reports are not easily accessible, but from news reports the following crane accidents occurred recently.

On Jul. 18, 2008, a crane collapsed in Houston, Tex. at an oil refinery. On May 31, 2008, a crane collapsed at the Black Thunder Mine in northeast Wyoming. On May 30, 2008, a crane collapsed in New York at the corner of 91st Street and First Avenue. On Mar. 15, 2008 a crane collapsed in New York at the corner of 51st Street between Second and First Avenues.

According to Congressional Research Service report RL34658 *Worker Safety in the Construction Industry: The Crane and Derrick Standard*, updated Nov. 21, 2008, and incorporated by reference herein, there were 66 fatal injuries involving cranes in 2007; 69 in 2006; 83 in 2005; 85 in 2004; and 61 in 2003.

Railroad bridge failures occurred following flooding in Cedar Rapids on Jun. 12, 2008 and in Columbus Junction, Iowa on Jun. 24, 2008. In both cases, the bridges collapsed into the river with trains on the bridges.

On Nov. 15, 1988 the National Radio Astronomy Observatory 300-Foot Radio Telescope at Green Bank, W. Va. collapsed while observing. Prior to the collapse, it had been noted that the pointing had changed. Extensive visual inspections by maintenance mechanics climbing on the telescope earlier in the day, prompted by the pointing change, failed to identify a gusset plate which was subsequently identified as the probable cause of the collapse in a National Science Foundation Report. Without conclusive engineering data, the pointing change was dismissed as possibly due to electronic instrumentation problems.

Catastrophic failures during construction are all to frequent. For example: On Oct. 30, 2008, a parking garage under construction collapsed in Atlantic City, N.J. On Oct. 27, 2008, a bridge under construction in Nampa, Id. collapsed while concrete was being poured. On Feb. 10, 2008, a stadium under construction in Fort Worth, Tex. collapsed.

There have also been catastrophic failures of standing buildings. On Jul. 7, 1981 suspended walkways in the Kansas City Hyatt Regency Hotel collapsed killing 114 and injuring 200. On Jun. 4, 1979 the Kemper Arena roof collapsed in 70 mph wind and heavy rain. On Jan. 18, 1978 the Hartford Civic Center roof collapsed due to snow loading.

Clearly there is a need in the art for additional Structural Health Monitoring measures to prevent the loss of life and property.

Preventative Measures for Civil Structural Failures

Bridge Inspection

In the United States, Highway bridge inspection is under the Department of Transportation Federal Highway Administration and Title 23 of the Code of Federal Regulations (CFR) Part 650-Bridges, Structures, and Hydraulics. Specifically, 23 CFR Part 650 Subpart C-National Bridge Inspection Standards, the index of which is incorporated by reference herein, specifies the inspection frequency, inspection procedures, and reference manuals.

The American Association of State Highway and Transportation Officials (AASHTO) provides additional guidance for bridge inspections through publications such as the Manual for Bridge Evaluation. It was noted in the I-35W investigation that AASHTO guidance used by states to perform bridge inspections does not include gusset plates as a CoRe element. Moreover, it had been observed that one of the gusset plates in question had actually been observed to be bowed in the prior inspections, but was not identified as a problem.

Railroad bridge inspection is under the Department of Transportation Federal Railroad Administration and Title 49 of the Code of Federal Regulations (CFR) Part 237—Bridges Safety Standards. The American Railroad Engineering and Maintenance-of-Way Association (AREMA) develops industry standards for inspection and maintenance of railway bridges.

Crane Inspection

Crane inspection is under the Occupational Safety and Health Administration (OSHA) and Title 29 of the Code of Federal Regulations (CFR) Subpart N-Cranes, Derricks, Hoists, Elevators, and Conveyors. Section 1926.550 covers Cranes and Derricks in under eight pages. The spirit of the regulations is captured in subsection (a) paragraph (1)

(a) General requirements. (1) The employer shall comply with the manufacturer's specifications and limitations applicable to the operation of any and all cranes and derricks. Where manufacturer's specifications are not available, the limitations assigned to the equipment shall be based on the determinations of a qualified engineer competent in this field and such determination will be appropriately documented and recorded. Attachments used with cranes shall not exceed the capacity, rating, or scope recommended by the manufacturer.

Academic Research in Civil Structural Health Monitoring

Structural Health Monitoring is a relatively new field of formal study. The 1st International Workshop on Structural Health Monitoring was held in 1997, with additional workshops and Proceedings published every 2 years thereafter. The 7th International Workshop on Structural Health Monitoring will be held Sep. 9-11, 2009 at Stanford University. In the call for papers, incorporated by reference herein, under the heading Sensors and Actuator Development, papers are requested for; integrated sensors, wireless sensors, "smart" sensors, fiber optics, piezoelectrics, shape memory, alloys/polymers, MEMS sensors and micro-actuators, nano-sensors, etc.

SPIE has sponsored a number of conferences on Smart Structures. A search of the SPIE Proceedings produces 194 published Proceedings starting with Volume 0986 in 1988, a listing of which is incorporated by reference herein. SPIE will hold Smart Structures/NDE Mar. 8-12, 2009 in San Diego. The Program will include 10 sessions including 7292: Sensors and Smart Structures for Civil, Mechanical, and Aerospace Systems 7294: Nondestructive Characterization of Composite Materials, Aerospace Engineering, Civil Infrastructure, and Homeland Security III 7295: Health Monitoring of Structural and Biological Systems III the program listings of which are incorporated by reference herein, from which it will be understood that the topics of the papers are similar to the International Workshop on Structural Health Monitoring topics listed hereinabove.

Los Alamos National Laboratory has a project on Structural Health Monitoring, and has produced *A Review of Structural Health Monitoring Literature: 1996-2001*. The Web Page, Publication list, and Review is hereby incorporated by reference herein, from which it will also be understood that the topics of the papers are similar to the International Workshop on Structural Health Monitoring topics listed hereinabove.

The University of Illinois at Urbana Champaign established the Smart Structures Technology Laboratory in 2002, and has a large Graduate Program focusing on the areas of structural health monitoring, structural control, and smart sensor technologies.

Missouri Science and Technology University (formerly the University of Missouri-Rolla) operates the Center for Transportation Infrastructure and Safety. They have conducted a number of interesting studies of bridge deflections using a single total station. A summary listing of reports were cited in the parent application Ser. No. 12/973,842 and will not be repeated herein.

The Federal Highway Administration awarded a $25.5 million contract to the Rutgers Center for Advanced Infrastructure and Transportation establishing a Long-Term Bridge Performance Program (LTBPP).

Sage Journals Online publishes Structural Health Monitoring, An International Journal, with Volume 1 published in 2002. Edited by Fu-Kuo Chang of Stanford University, the web link and description is incorporated by reference herein. Yet again, the topics of the papers are similar to the International Workshop on Structural Health Monitoring topics listed hereinabove.

Books are beginning to be published on the subject. Useful references include *Structural Condition Assessment*, Robert T. Ratay, Wiley, 2005; and *Health Monitoring of Bridges*, Helmut Wenzel, Wiley, 2009.

A review of the aforementioned bibliographic sources presents one with a clear understanding of the prior art in the academic community at the time of the invention. In particular, the measurement techniques tend to concentrate on either localized strain measurements, vibrational analysis, localized movements of such things as joints, or wireless sensor technology. Moreover, measurements are directed toward measuring the expected performance of a healthy structure. For example, where LVDT transducers are placed to measure deflections, they are typically placed in the direction of the maximum expected deflection. However, in the case of a defective structure, detection of unexpected motions would provide even more valuable information.

The concentration of research into such a closed set of fields is possibly due in part to the emphasis of the National Science Foundation (NSF) by the Strategic Civil Infrastructure Systems Research Program, developed in 1993, as described by Liu and Tomizuka in *Vision and Strategy for Sensors and Smart Structures Technology Research*, incorporated by reference herein, i.e., the research follows the funding. It is also possibly due to the historic development of large-scale metrology around manufacturing, which may not attract the attention of structural engineers.

Historical Overview of Pressure Vessel Structural Failures

Electronic Distance Measurement instrumentation can also be used to measure the structural health of large pressure vessels, including boilers, receivers, nuclear reactor containment structures, tank trucks, railway tank cars, storage tanks, ships, buoyant devices, reservoirs, vacuum chambers, aircraft, spacecraft, and the like. As used hereinbelow, a pressure vessel will be understood to include any enclosed or open pressure vessel or container which is structured to support the forces of a differential pressure between two sides of a boundary. The differential pressure may be generated by the static weight of a material, compression, vapor pressure of a liquid, heat, vacuum, etc. The pressure may be higher internally, as in the case of a boiler or storage tank, or higher externally, as in the case of a vacuum chamber or ship hull.

Nuclear Power Plant Containment Buildings

From the outset of commercial nuclear power plant design, it was recognized that there is a need to provide a primary containment structure to contain radioactive material in the event of an accident. U.S. Pat. No. 3,865,688 Passive containment system; U.S. Pat. No. 4,050,983 Passive containment system; and U.S. Pat. No. 4,473,528 Passive containment system to Kleimola: U.S. Pat. No. 4,045,289 Nuclear reactor containment structure with continuous ring tunnel at grade to Seidensticker et al.: U.S. Pat. No. 4,080,256 Nuclear reactor apparatus to Braun: U.S. Pat. No. 4,091,583 Wall of pressurized reinforced concrete tank to Genis et al.: U.S. Pat. No. 4,175,005 Component nuclear containment structure to Harstead: and U.S. Pat. No. 4,927,596 Self-actuating pressure relief device and method for nuclear containment to Minnick, all eight of which are incorporated by reference herein, provide a good overview of containment structures for boiling water reactors (BWR) and pressurized water reactors (PWR). A primary concern, and the subject of many studies, has been a loss of coolant to the reactor core.

On Mar. 11, 2011, a magnitude 9.0 earthquake off the coast of Tohoku triggered a tsunami which disrupted power at the Tokyo Electric Power Company (TEPCO) Fukushima I (Fukushima dai-ichi) Nuclear Power Plant, in the Fukushima Prefecture, Japan. At the time of the earthquake, BWR Units 1-3 were operating and Units 4-6 were out of service. Following the earthquake, Units 1-3 automatically shut down. Site power delivered by the grid was lost as a result of the earthquake. Backup diesel generator power was later lost as a result of the tsunami. Backup battery power was soon exhausted, which resulted in loss of coolant to the reactors.

As explained in *Possible Cause of Reactor Building Explosions*, David Lochbaum, incorporated by reference herein, in a BWR, the reactor pressure vessel is enclosed within a relatively small primary containment structure (as compared to a PWR). Due to the loss of coolant, and subsequent high temperature and pressure of the reactor vessel, steam was relieved from the reactor vessel into the primary containment structure. As explained by Lochbaum, a loss of coolant accident can produce hydrogen in addition to steam. In the case of the Fukushima accident, there were explosions outside the primary containment structure-which indicate that the primary containment structures failed to contain the pressure of the vented steam and hydrogen. The Unit 1 building exploded on March 12, the Unit 3 building exploded on March 14, and the Unit 2 building exploded on March 15, i.e., three out of three primary containment structures failed to contain the steam and hydrogen in a loss of coolant accident.

Lochbaum makes a good argument that the drywell flange seal probably failed at around 62 psi. This problem was outlined in *Containment of a reactor meltdown*, Jan Beyea and Frank von Hippel, incorporated by reference herein, which was originally published September 1982 and republished March 2011. The authors state;

> If for any reason the emergency core cooling system were not effective and a core meltdown occurred, the build-up of internal pressure in a sealed reactor containment building could rupture it within a matter of hours. The threat would come from steam, hydrogen and other gases.

Frank von Hippel published another article *Second chances: Containment of a reactor melt-down* in March 2011, incorporated by reference herein, which used the Fukushima I as an example.

According to the European Nuclear Society article *Nuclear power plants, world-wide*, incorporated by reference herein, as of Mar. 30, 2012, there are 436 operating nuclear power plants, with 104 in the US. In light of the Fukushima I accident, and the failure of all three primary containment structures, there is sure to be a renewed emphasis on ways to assure integrity of the primary containment structures.

In the US, nuclear power plants are regulated under Title 10 of the Code of Federal Regulations, 10 CFR. In particular, 10 CFR Appendix J to Part 50—Primary Reactor Containment Leakage Testing for Water-Cooled Power Reactors, incorporated by reference herein, specifies the testing regulations for primary containment structures. The testing methods basically call for pressurizing the building to the design pressure and checking that the pressure holds for a predetermined time after closing the valve to the pressure source. Leaks are found by using standard soap bubble solution and visual inspections, i.e., much like checking a tire.

Boilers and Unfired Pressure Vessels

The National Board of Boiler and Pressure Vessel Inspectors maintains a database of boiler and pressure vessel incident statistics. A report published in the Summer 2002 issue of the National Board Bulletin, incorporated by reference herein, compiled incident data between 1992 and 2001. Over the ten year period, there were; 127 fatalities, 720 injuries, and 23,338 accidents. Of the fatalities; 64 were killed by unfired pressure vessels, 44 by power boilers, 14 by water-heating boilers, and 5 by steam-heating boilers. Of the injuries; 289 were due to unfired pressure vessels, 250 due to power boilers, 92 due to water-heating boilers, and 89 due to steam-heating boilers. Of the accidents; 9,588 were due to steam-heating boilers, 6,928 due to water-heating boilers, 4,311 due to power boilers, and 2,511 due to unfired pressure vessels. Note that the fatality and injury rate per accident is much higher for unfired pressure vessels than the other classifications.

In the US, general use pressure vessels are regulated by the Occupational Safety and Health Administration (OSHA), Department of Labor, under Title 29 of the Code of Federal Regulations Part 1910, i.e., 29 CFR 1910. In particular; Subpart H covers hazardous materials, and subpart M covers compressed gas and compressed air equipment.

OSHA publication 8-1.5, GUIDELINES FOR PRESSURE VESSEL ASSESSMENT, 1989, incorporate by reference herein, provides a good overview of problems experienced by pressure vessels and prior art inspection methods. Section 5.0 Inspection Methods and Implementation, provides a good overview of conventional nondestructive examination (NDE) methods and cites the role of organizations such as; the American Society of Mechanical Engineers (ASME) Boiler and Pressure Vessel Code (BPVC), the American Petroleum Institute (API) Standards, the National Board of Boiler and Pressure Vessel Inspectors-National Board Inspection Code (NBIC), and the American Society for Nondestructive Testing (ASNT) Recommended Practice. Section V of the ASME BPVC covers Nondestructive Examination, the table of contents of which is incorporated by reference herein.

Transportation of Hazardous Materials

In the US, transportation of hazardous materials is subject to the Federal Hazardous Materials Transportation Law under Title 49 of the United States Code, Chapter 51, i.e., 49 U.S.C. 5101 et seq. and administered by the Department of Transportation (DOT). A good overview is provided in the pamphlet *Federal Hazardous Materials Transportation Law An Overview*, published by the DOT Pipeline and Hazardous Materials Safety Administration, incorporated by reference herein. Under § 5103 (b)(1) the Secretary of Transportation is given authority to prescribe regulations. Under § 5103(b)(1)(A)(iii) the regulations apply to a person who—

> (iii) designs, manufactures, fabricates, inspects, marks, maintains, reconditions, repairs, or tests a package, container, or packaging component that is represented, marked, certified, or sold as qualified for use in transporting hazardous material in commerce;

which of course covers those involved in pressure vessels used in transportation.

Responsibilities are shared by the DOT Pipeline and Hazardous Materials Safety Administration (PHMSA), the DOT Federal Motor Carrier Safety Administration (FMCSA), the DOT Federal Railroad Administration (FRA), the DOT Research and Innovative Technology Administration (RITA), and others. Hazardous Materials Regulations (HMR) are covered under Title 49 of the Code of Federal Regulations Parts 171-180, i.e., 49 CFR 171-180. Transportation by highway is regulated under 49 CFR 350-399. Transportation by railroad is regulated under 49 CFR 200-268.

A good overview of the FMCSA regulations is found in a report by Virginia Tech, *Guidelines for the Operation, Assembly, Repair, Testing and Inspection of Hazardous Material Cargo Tanks*, incorporated by reference herein. In particular, section 4 covers Cargo Tank Repair. It cites the ASME BPVC Section XII—Rules for Construction and Continued Service of Transportation Tanks, and the National Board of Boiler and Pressure Vessel Inspectors NBIC for guidance.

Section 5 covers Test and Inspection Guidelines. Section 5.9 covers Requirements for Test and Inspection of Specification Cargo Tanks. Details of the six tests prescribed in 49 CFR 180.407 are given for; external visual inspection (V) § 180.407(d), internal visual inspection (I) § 180.407(e), lining test (L) § 180.407(f), pressure retest (P) § 180.407(g), leakage test (K) § 180.407(h), and thickness test (T) § 180.407(i).

Statistics on the number of trucks regulated by the FMCSA are not readily available, but *Facts about Propane*, published by the National Propane Gas Association (NPGA), incorporated by reference herein, cites a fleet of 6,000 transport trucks (7,000-12,000 gallons), 36,500 bobtails (1,000-5,000 gallon delivery trucks), and 22,000 railway tank cars. The vapor pressure of propane is listed at 287 psig at 130° F.

Prior to the creation of the Pipeline and Hazardous Materials Safety Administration under Public Law 108-426 on Nov. 30, 2004, the DOT Research and Special Programs Administration (RSPA) handled hazardous materials. On Dec. 8, 1987, RSPA published an Advanced Notice of Proposed Rulemaking (ANPRM) in the Federal Register, 52

FR 46510, incorporated by reference herein. RSPA for Detection and Repair of Cracks, Pits, Corrosion, Lining Flaws, Thermal Protection Flaws, and Other Defects of Tank Car Tanks. The fleet affected by HM-201 is estimated by the FRA to be 240,000 railway tank cars. The opening paragraph of the advanced notice stated;

> As a result of actions taken in response to an incident involving a tank car leaking ethylene oxide on Dec. 31, 1984, at North Little Rock, Ark., RSPA and FRA have identified a problem concerning tank cars with small cracks.

The advanced notice concluded with a request for comments on 5 questions, including;

> 3. What inspection techniques (e.g. ultrasonic, magnetic particle, acoustic emission, and radiographic) are appropriate to detect small cracks, pits, corrosion, lining flaws, thermal protection flaws, and other defects?

On Sep. 16, 1993, RSPA published a Notice of Proposed Rulemaking (NPRM) in the Federal Register, 58 FR 48485, incorporated by reference herein. The NPRM commented on 14 comments received in response to the 5 questions in the ANPRM. In addition, section A Adequacy of Hydrostatic Test is particularly interesting. The history of hydrostatic testing was tied to a legacy of riveted or forge welded construction. It went on to make a case that hydrostatic testing at 1.3 times the maximum allowable working pressure (MAWP) is limited with respect to detecting fatigue cracks in fusion welded tanks.

It recited an incident on Jan. 18, 1992 at Dragon, Miss. where a tank car loaded with liquefied petroleum gas split apart at a circumferential weld seam as the train began to pull out of a siding. As a result, the National Transportation Safety Board subjected seven cars with known cracks to a hydrostatic test. None of the test showed any indication that a crack was present. It also recited an incident on Mar. 25, 1992 at Kettle Falls, Wash. in which a tank car failed on its first post-test loaded move.

> Section A concluded with the statement;
> Based on the ineffectiveness of hydrostatic tests in detecting significant fatigue cracking in tank cars resulting from severe loadings, stress risers, and welding defects, RSPA and the FRA no longer consider the hydrostatic test part of the optimum way to qualify fusion welded tank cars for continued service.

On Sep. 21, 1995, RSPA published the Final Rule 60 FR 49047, incorporated by reference herein. The Final Rule for HM-201 was combined with Crashworthiness Protection Requirements for Tank Cars, starting on page 49058. The Final Rule commented on 31 comments received in response to the NPRM and concluded with amendments to 49 CFR §§ 171, 172, 173, 179, and 180.

In support of HM-201, the FRA Office of Research and Development contracted with the Transportation Technology Center, Inc. (TTCI) a subsidiary of the American Association of Railroads (AAR) to perform joint government/industry evaluation of possible replacement test/inspections for the presently prescribed hydrostatic test/visual inspection of tank cars. The Federal Railroad Administration Office of Research and Development published the research in report Railroad Tank Car Nondestructive Methods Evaluation in January 2002, incorporated by reference herein.

> Subsection 3.3 covers Developing a Validation Methodology. Subsubsections cover: 3.3.1 Liquid Penetrant Test Method, 3.3.2 Magnetic Particle Test Method, 3.3.3 Radiographic Test Method, 3.3.4 Ultrasonic Test Method, 3.3.5 Visual Test Method, and 3.3.6 Acoustic Emission Test Method.

On Nov. 30, 2004, Congress created the Pipeline and Hazardous Materials Safety Administration in the DOT, under Public Law 108-426. Duties of the Research and Special Programs Administration were transferred to PHMSA. On Jan. 13, 2009, PHMSA published Final Rule for *Hazardous Materials: Improving the Safety of Railroad Tank Car Transportation of Hazardous Materials*. The rules amend the Hazardous Materials Regulations under 49 CFR §§ 171, 172, 173, 174, and 179. In particular it deals with poison inhalation hazard (PIH) materials, also called toxic inhalation hazard (TIH) materials. The Final Rule recites three incidents involving PIH;

> In the last several years, rail tank cars have been breached in numerous accidents, resulting in large releases of hazardous materials. Of particular concern, three of these accidents involved PIH materials: (1) The Jan. 18, 2002, derailment of a Canadian Pacific (CP) train in Minot, N. Dak. which resulted in a release of anhydrous ammonia; (2) the Jun. 28, 2004 collision between trains operated by Union Pacific Railroad Company (UP) Burlington Northern and Santa Fe Railway Company (now known as BNSF Railway Company) in Macdona, Tex. involving a breach of a loaded tank car containing chlorine; and (3) the Jan. 6, 2005 collision between two Norfolk Southern Railway Company (NS) trains in Graniteville, S.C., also involving the catastrophic rupture of a loaded chlorine tank car. As noted in the NPRM, although none of these accidents was caused by the hazardous materials tank cars, the failure of the tank cars involved led to fatalities, injuries, evacuations, and property and environmental damage.

The NPRM proposed replacement of the entire fleet of tank cars used to transport PIH materials, estimated at 15,300 of the 240,000 tank cars in the fleet, within eight years of the effective date. The industry responded that it lacked the technological and engineering ability to manufacture tank cars meeting the proposed standards. The rule was changed to be an interim response based on current engineering judgments within the affected market sector. It is anticipated that additional regulatory proceedings will result as continuing government and private sector research and development are validated and the resulting technology is successfully implemented by industry.

Aircraft and Spacecraft

Pressurized aircraft and spacecraft are another embodiment of pressure vessels. On Apr. 18, 1988, Aloha Airlines flight 243 experienced an explosive decompression at 24,000 feet, near Kahului, Hi. According to the National Transportation Safety Board Aircraft Accident Report NTSB/AAR-89/03 executive summary, incorporated by reference herein, > The National Transportation Safety Board determines that the probable cause of this accident was the failure of the Aloha Airlines maintenance program to detect the presence of significant disbonding and fatigue damage which ultimately led to failure of the lap joint at S-10L and the separation of the fuselage upper lobe.

On Apr. 1, 2011 Southwest Airlines flight 812 experienced a 9 inch wide by 59 inch long rupture in the fuselage at 34,000 feet, near Yuma, Ariz. A final report has not yet been issued, but a press release on Apr. 25, 2011 stated, > Non-destructive eddy current inspections conducted around intact rivets on the removes skin section forward of the rupture revealed crack indications at nine rivet holes in the lower rivet row of the lap joint. To assess the condition of the intact rivets and the skin rivet holes, X-ray inspections were performed on the skin located forward of the rupture location. The inspection revealed gaps between the shank portions of several rivets and the corresponding rivet holes for many rivets associated with S-4L. Upon removing selected rivets, the holes in the upper and lower skin were found to be slightly offset relative to each other and many of the holes on the lower skin were out of round.

Aircraft are regulated under Title 49 of the United States Code 49 U.S.C. which authorizes the FAA to regulate air safety under 14 CFR. Subchapter C of 14 CFR sections 21-49 cover aircraft standards and 14 CFR 39.13 provides for the FAA to issue Airworthiness Directives (AD) as amendments to § 39.13. On Apr. 5, 2011, in response to the flight 812 accident, the FFA issued AD #2011-08-51 which directed that a Boeing Alert Service Bulletin dated Apr. 4, 2011 be followed to conduct eddy current inspections of the lap joint stringers. While eddy current inspections could identify cracks, it is not clear how eddy current inspections could detect improper fitting holes between the upper and lower skin as described in the April 25 press release.

Prestressed Concrete

It is well known in the art that just as a chain is strong in tension, but weak in compression; concrete is strong in compression, but weak in tension. For design purposes, it is assumed that concrete has no tensile strength. Stress $\sigma=F/A$, where F is force and A is the area over which the force F is applied. Strain $\epsilon=\Delta L/L$, where L is length and $\Delta L$ is the change in the length L due to the stress $\sigma$. The modulus of elasticity E is the ratio of stress $\sigma$ to strain $\epsilon$, i.e., $$E = \frac{F/A}{\Delta L/L}. \qquad (1)$$

From the *Schaum's Outline of Reinforced Concrete Design*, the modulus of elasticity depends on the density of the concrete and the compressive strength. The density is typically between 80 and 145 lb/ft$^3$, the compressive strength is typically between 2,500 and 8,000 psi, and the modulus of elasticity is typically between 1×10$^6$ and 5×10$^6$ psi. For a typical density of 120 lb/ft$^3$, modulus of elasticity E of 3×10$^6$ psi, and a maximum compression stress $\sigma$ of 5,000 psi, the maximum strain $\epsilon$ before the concrete fractures would be about 1.666×10$^{-3}$, or 1,666 microstrains. In other words, in order for concrete with these properties not to crack, the strain $\epsilon$ should be controlled such that it is always in compression, and $$0 \leq \epsilon < 1.666 \times 10^{-3}. \qquad (2)$$

In order to avoid failure, all of the elements in a concrete structure should be maintained in compression, with a margin of safety, under all dead and live load conditions—including during intermediate construction phases, shipping, handling, erection, intended use, wind, earthquake, accidents, etc.

Francois Hennebique understood these principles, for which he was inducted into the National Inventors Hall of Fame in 2011 for "the pioneering technique of construction with reinforced concrete", as disclosed in his 1898 U.S. Pat. No. 611,907 Construction of Joist, Girders, and the Like, which is incorporated by reference herein. The invention is characterized in the second paragraph:

The use of strengthened benton in buildings has within recent years greatly developed. It has been thought possible by mixing beton and iron or steel to replace the purely metallic elements of building construction by parts equally incombustible but lighter and more simply and rapidly made. In any case the mixture of cement or hydraulic lime, which resists perfectly compression with iron or steel, which more particularly resists tension and flexion, has not hitherto been capable of being carried out in a judicious and rational manner.

By arranging at useful points in a mass of benton of suitable form longitudinal bars of iron of a given shape in order to constitute the tension-cord, by distributing them in the mass in a judicious manner in order that the whole mass of iron and beton may have at every point of the piece formed the desired resistance to flexion and tension, and by further connecting the longitudinal bars by brace-pieces or stirrups of suitable form I have succeeded in producing the practical joists, girders, and the like which form the object of my present invention.

The coefficient of thermal expansion for Portland cement concrete is about 8 to 12 parts per million per ° C.—which is about the same as steel. For steel reinforced concrete, the steel reinforcing bars (rebar) are embedded in the concrete as the concrete is placed, i.e., at the same temperature. For all practical purposes the steel and concrete expand and contract together under thermal changes.

Under conditions where the concrete would be placed in tension when cooling and contracting, such as a slab or sidewalk dragging with a shear force against the ground, the reinforcing steel provides the tensile strength to prevent the concrete from cracking. In cases where a load is applied to the cured concrete that would put the concrete in tension, as in the bottom cord of a joist, the reinforcing steel again provides the tensile strength to prevent the concrete from cracking.

While this is a simple construction technique, it does not fully exploit the compressive strength of concrete, nor the tensile strength of steel. For reinforced concrete starting with a strain $\epsilon=0$, the steel produces no tensile force F. In order for the steel to produce a tensile force, as explained by Hooke's law, it must be subjected to a stress $\sigma$ that elongates the steel, like a spring, to produce a strain $\epsilon$ in tension. However, the bonded concrete is subjected to the same elongation strain $\epsilon$, which puts the concrete under tension. Far before the steel reaches its maximum strain, the concrete will have cracked and openings will have developed.

In the late 1940s, the steel reinforced technique was improved by prestressing the structure by using cable tendons and hydraulic jacks to tension the tendons. By biasing the concrete in compression and the steel in tension, additional loading, such as the live load, that causes the steel to further elongate, simply reduces the compression of the concrete, rather than subjecting it to the highly nonlinear condition of reversing the strain from compression to tension. In other words, the response to the additional loading will be linear.

Another way to think of the difference is that in steel reinforced concrete, the steel and concrete complement each other, i.e., one is strong in tension and the other is strong in compression. Whereas in prestressed concrete, the steel and concrete are engineered to work in harmony so as to optimize the performance of the concrete by maintaining it in compression at all times.

The first prestressed bridge in the United States was the Walnut Lane Bridge in Philadelphia, which was designed in 1949 and opened to traffic in 1951. A short history of prestressed concrete by Howard Newlon, Jr. is included in Chapter 11 of *Twentieth-Century Building Materials: History and Conservation*, which is incorporated by reference herein. A more detailed history, with a number of patent references, is found in *The four ages of early prestressed concrete structures*, Sanabra-Loewe and Capellà-Llovera, pp. 93-120, PCI Journal, Fall 2014, which is incorporated by reference herein.

Prestress is typically introduced by pre-tensioning or post-tensioning, where the tendons are tensioned before the concrete cures for pre-tensioning and after the concrete cures for post-tensioning. In the case of pre-tensioning, the concrete bonds to the tendon when it cures. Since the concrete is uncured, the jacks must push against external fixed anchors. This process lends itself well to factory precast concrete operations. However, due to shipping and handling constraints, precast concrete has maximum size constraints.

In the case of post-tensioning, the tendons are placed in conduits embedded in the concrete. Grout may be added to bond the tendon to the concrete, or the tendon may remain unbonded in order to adjust, or detension, the tendon at a later time. The jacks typically push against the cured concrete structure, which lends itself well to poured in place concrete structures of unlimited size and geometrical shape. However, due to the fact that tensioning is conducted in the field, forces may be over 1,000,000 lbf, and the geometric shapes may be one of a kind construction, each tensioning may require additional engineering and rigging.

In addition, whereas with precast concrete all tendons are stressed before the concrete is placed, post-tensioning is usually conducted one tendon at a time, i.e., in series. This can temporarily produce high stresses in other parts of the structure. Because of the interactions, additional engineering and operations may be required to determine the tensioning sequence-including repeating some tensioning operations several times, i.e., much like tuning a piano. The technique is well known in the art and will not be described in greater detail, but an overview is found in Wikipedia article *Prestressed concrete*, which is incorporated by reference herein.

The use of post-tensioned concrete for slabs, columns, girders, and bridges are disclosed in U.S. Pat. No. 2,826,800 Pre-stressing of concrete assemblies to Van Buren; U.S. Pat. No. 4,574,545 Method for installing or replacing tendons in prestressed concrete slabs to Reigstad et al.; and U.S. Pat. No. 6,751,821 Prestressed concrete girder of adjustable load bearing capacity for bridge and adjustment method for load bearing capacity of bridge to Han; all three of which are incorporated by reference herein.

The use of prestressed concrete for bridge construction is well known in the art and will not be described in detail herein. However, a good overview of post-tensioned concrete for bridge applications is in Florida Department of Transportation (FDOT) publication, *New Directions for Florida Post-Tensioned Bridges, Volume 1 of 10: Post-Tensioning in Florida Bridges*, 2002, which is incorporated by reference herein. Unless otherwise noted, the definitions of terms in Appendix A will be assumed herein.

Chapter 2 of the FDOT publication presents an overview, with drawings, of post-tensioning by various bridge types, e.g.;
2.1 Precast Segment Balanced Cantilever Bridges
   2.1.1 Cantillever Tendons
   2.1.2 Continuity Tendons
   2.1.3 Continuity Tendons At Expansion Joints
2.2 Precast Segmental Span-by-Span Bridges
2.3 Post-Tensioned AASHTO, Bulb-T, and Splice Girders
2.4 Cast-in-Place Segmental Balanced Cantilever Bridges
2.5 Cast-in-Place Bridges on Falsework
2.6 Temporary Longitudinal Post-Tensioning (Bars)
2.7 Transverse Post-Tensioning of Superstructures
   2.7.1 Transverse Top Slab Post-Tensioning
   2.7.2 Transverse Post-Tensioning in Diaphragms
   2.7.3 Vertical Post-Tensioning in Diaphragms
   2.7.4 Transverse Post-Tensioning in Deviator Ribs of Precast Segments
   2.7.5 Vertical Post-Tensioning Bars in Webs
2.8 Post-Tensioning of Substructures
   2.8.1 Hammerhead Piers
   2.8.2 Straddle Bents
   2.8.3 Cantilever Piers
   2.8.4 Precast Box Piers
   2.8.5 Precast I-Section Pier Columns
   2.8.6 Transverse, Confinement Tendons at top of Piers Prestressed concrete is widely used for towers, such as for elevated water storage tanks, cooling towers, and wind power generation, e.g., U.S. Pat. No. 4,092,811 Cooling tower, construction method therefor and precast prestressed concrete building units to Lin et al.; U.S. Pat. No. 7,739,843 Pre-stressed concrete tower for wind power generators to Cortina-Cordero; U.S. Pat. No. 8,220,212 Concrete tower to Stiesdal; and U.S. Pat. No. 8,919,074 Telescopic tower assembly and method to Meyer et al.; all four of which are incorporated by reference herein.

Prestressed concrete is widely used for storage tanks-including cryogenic fluids, such as liquefied natural gas (LNG), which is stored at −165° C. Example applications include U.S. Pat. No. 3,633,328 Pressurized storage tank to Closner et al.; U.S. Pat. No. 4,041,722 Impact resistant tank for cryogenic fluids to Terlesky et al.; U.S. Pat. No. 4,265,066 Prestressed concrete pressure vessels to Lin et al., and published application US 2010/0154318 Ring beam and method for constructing the same to Shockley et al., all four of which are incorporated by reference herein.

Review articles include:
Kaźierczak, *Selected issues of prestressed concrete containment tanks for the storage of liquefied gases design in accordance with EN 14620*;
Lun et al., *Design and construction aspects of post-tensioned LNG storage tanks in Europe and Australia*;
Hjorteset et al., *Development of large-scale precast, prestressed concrete liquefied natural gas storage tanks*; and
VSL International LTD., Concrete Storage Structures;
all four of which are incorporated by reference herein.

US safety standards include:
49 CFR 193.2001-193.2917, *Liquefied natural gas facilities*; and
American Concrete Institute 376-11, *Code Requirements for Design and Construction of Concrete Structures for Containment of Refrigerated Liquefied Gases and Commentary.*

British safety standards include:
BS EN 14620-3:2006, *Design and manufacture of site built, vertical, cylindrical, flat-bottomed steel tanks for the storage of refrigerated, liquefied gases with operating temperatures between 0° C. and −165° C., Part 3: Concrete components.*

Due to the extreme temperature differential between LNG and the ambient, and the inherent fire, explosion, and inhalation safety hazards, there are a number of unique considerations. For example, even though there is a thick insulation layer between the inside metal liner and the outside concrete structure, the concrete structure (and tendons) contracts by several inches when it is loaded with the cold LNG, and expands when the LNG is removed.

BS EN 14620-3:2006 recommends, in section 8.6, that the tendons be placed in the center of the concrete wall for protection against external fires. In other words, care must be taken to ensure the tendons don't fail due to an external fire. This fire protection requirement is in conflict with structural requirements, which would place the tendons near the outside wall in order to put the entire wall in compression. Note that this requirement imposes a shear force in the concrete between the layer inside the hoop tendons (which will be in compression), and the layer outside the tendons (which will be in tension). This is in addition to the forces produced when LNG is introduced into the tank and the walls are contracting radially due to the cooling of the inside concrete surface. The concrete inside the hoop tendons remains in compression during the contraction, whereas the concrete outside the hoop tendons is pulled inward by the contraction. This could easily produce a delamination along the tendon line. Moreover, such a delamination could easily go undetected in normal service.

Prestressed concrete is widely used for nuclear power plant containment buildings. A good overview of the art is covered by the eight patents incorporated by reference hereinabove, under the section: Nuclear Power Plant Containment Buildings.

In 1998, the International Atomic Energy Agency (IAEA) produced the 157 page report, IAEA-TECDOC-1025, *Assessment and management of aging of major nuclear power plant components important to safety: Concrete containment buildings*, which is incorporated by reference herein. Section 4 covers test methods used in current practice.

In the US, nuclear power plants are licensed for 40 years, with one 20 year renewal. The oldest plants reached the 40 year mark in 2009 and have started on the 20 year renewal, i.e., plants will start reaching the 60 year retirement in 2029.

The US Department of Energy, Office of Nuclear Energy, has a Light Water Reactor Sustainability (LWRS) Program to develop the scientific basis to extend existing nuclear power plant operating life beyond the current 60-year licensing period. One of the areas being investigated is Materials Aging and Degradation (MAaD) Assessment, which includes the concrete containment buildings. Research is being conducted at Oak Ridge National Laboratory.

A review of the research is found in the following articles and reports:
Clayton, et al., *Research and Development Roadmaps for Nondestructive Evaluation of Cables, Concrete, Reactor Pressure Vessels, and Piping Fatigue;*
Clayton, et al., *Summary of Large Concrete Samples;*
Clayton, et al., *Comparative testing of nondestructive examination techniques for concrete structures;*
Clayton, et al., *Nondestructive Evaluation of Thick Concrete Using Advanced Signal Processing Techniques;*
Clayton, *Nondestructive Evaluation of Thick Concrete Structures;* and
Clayton, *Improving Synthetic Aperture Focusing Technique for Thick Concrete Specimens via Frequency Banding;*
all six of which are incorporated by reference herein.

A European project to combine finite element analysis with nondestructive testing operated under the acronym CONMOD. Reports include:
Jovall, et al., *Concrete containment management using the finite element technique combined with in-situ non-destructive testing of conformity with respect to design and construction quality (CONMOD);*
Klinghoffer, et al., *Condition assessment of concrete structures at nuclear power plants by state of the art non-destructive testing;* and
Naus, *Inspection of Nuclear Power Plant Structures-Overview of Methods and Related Applications—Section 5;*
all three of which are incorporated by reference herein.

Historical Overview of Post-Tension Concrete Failures

Box Girder Bridges

Walter Podolny, Jr., of the Federal Highway Administration, documented a number of problems that have led to cracking in post-tensioned concrete box girder bridges. This was published in the March-April 1985 issue of PCI Journal in the 58 page article, *The Cause of Cracking in Post-Tensioned Concrete Box Girder Bridges and Retrofit Procedures*. The article, which is incorporated by reference herein, covered the following topics:
Flexural Cracking
Shear Cracking
Thermal Stress Cracking
Cracking at or near Anchorages
Cracks Resulting From Vertical Curvature of Soffit Tendons
Pullout of Horizontally Curved Tendons
Other Cracking Modes Associated With Curved Tendons
Cracking and Spalling From Tendon Misalignment
Retrofit Measures
Design/Construction Recommendations.

Of particular relevance to the invention is a summary of incidents that occurred during post-tensioning, as detailed in the section on Pullout of Horizontally Curved Tendons. On the Las Lomas Bridge project, the failure was described as follows.

The bridge was post-tensioned with 12 draped tendons, which are continuous throughout the entire length of the structure. Four bundled tendons were placed in each web and all tendons were jacked from both ends at the abutments.

The first failure (FIG. 39) occurred during prestressing operations when the twelfth and last tendon, located in the north web along the inside of the curve, was near its full prestress. A loud noise, described as a "bang", was heard and all four tendons in that web broke away from the web for almost the entire length of the curved east span, tearing the curved reinforcing web along the profile of the tendons. Two days later, the east quarter-span length of tendons in the south web, along the outside of the curve, suddenly broke out of the concrete web, again making a loud noise [emphasis added].

An immediate inspection of the structure indicated that the horizontally curved tendons, exerting a radial horizontal pressure, had overloaded the reinforced concrete webs. This overload had caused the concrete to fail, allowing the tendons to straighten out and pull away from the webs (FIG. 40).

On the Kapiolani Interchange On-Ramp Project, the failure was described as follows.

During the first post-tensioning operations, four tendons out of six in each web were fully post-tensioned, then noise was heard and cracking and spalling were observed along the south web [emphasis added]. After that, most of the tendons were released except two tendons along the north web and one tendon along the center web which was not released.

Note that in all cases, noise due to catastrophic failure was the first indication of a problem, i.e., there was no mention of instrumentation monitoring the post-tensioning process. The article continues to summarize the two failures.

In both these structures, there was a combination of relatively sharp curvature, thin concrete cover over the tendons and the bundling of a number of large sized tendons close together. These failures are somewhat unique in that the problem would not have surfaced in the case of a flatter curvature, thicker concrete cover over the tendons, or adequate spreading of the tendons into individual ducts as compared to bundled ducts.

Turkey Point Unit 3 Nuclear Power Plant

Turkey Point Unit 3 is a 693 MW Westinghouse pressurized water reactor, located near Homestead, Fla., operated by Florida Power & Light. During construction, the containment dome concrete experienced delamination during post-tensioning of the tendons, prior to Jun. 17, 1970. Details of the failure are reported in a 117 page Florida Power and Light Company report: *Turkey Point Unit 3, Containment Dome Report*. The report is not dated and the authors are not listed, but a copy recovered from the Florida International University web site was stamped: "received Dec. 24, 1970". No other reports on the failure were found in a Nuclear Regulatory Commission ADAMS Public Documents search.

The dome is 125.5 feet in diameter and the concrete is 39 inches thick with a construction joint between the lower 8 inches and the upper 31 inches. The upper 39 inches was placed in 9 sections, with various construction joints. There are 165 tendons, in three groups of 55 tendons per group, with the groups rotated by 60 degrees and centered on one of the 6 buttresses. FIG. 2-3 shows all of group 1 tendons are 20" from the bottom; half of group 2 tendons are 16 "from the bottom and half are 24" from the bottom; half of group 3 tendons are 12" from the bottom and half are 28" from the bottom, i.e., no tendons are in the upper 11" of concrete.

Section 3.1 of the report documents the initial observations.

On Jun. 17, 1970, when 110 of 165 dome tendons had been tensioned, sheathing filler was observed leaking from a crack in the dome surface [emphasis added]. Nine sheaths had been filled on June 16, 4 were filled on June 17, and this work was considered to be the source of the sheathing filler leak.

The leakage location was at azimuth 216 degrees and a radius of 35' from the dome center. A small amount of concrete was chipped away adjacent to the crack.

A crack plane parallel to the surface (delamination) was found within an inch or so of the surface. There was evidence of sheathing filler flow on the surfaces created by the delamination.

On Jun. 22, 1970, a small bulge in the dome surface was noticed at azimuth of 296 degrees and a radius of 25 feet [emphasis added]. The concrete was broken through in one small spot with a hammer and a delamination was discovered at about ½" depth. The exploratory chipping was expanded laterally and towards the center of the dome, revealing that the delamination became thicker as the dome center approached. This stage of chipping was stopped at about 15 feet radius, at which point the separated layer was about 4" thick.

The initial investigation to determine the extent of the concrete separation below the surface was performed by soundings with a Swiss hammer and a steel sledge hammer. The steel hammer was found to be more effective in finding separations deeper into the concrete, and is considered reliable up to a depth of about 10 inches [emphasis added].

Sonic investigations with a V-scope were conducted. The pulse velocity technique does not lend itself to a concrete mass with large numbers of embedded conduits and a linear plate on the underside of the dome.

Four-inch diameter core samples were taken in 65 locations and concrete in a 7'×7' area was removed to a depth of 12" to 15". The results are summarized in section 3.2 of the report.

(1) The depth and extent of the delaminations has considerable symmetry about the meridional construction joint with major delaminations occurring on the south side of the dome.

(2) The delaminations appear to have originated at the meridional construction joint and then progressed away from the joint getting closer to the surface with eventual outcropping or termination at a circumferential construction joint.

(3) The adequacy of the meridional construction joint varied throughout the joint because of small voids and other evidence of lack of proper consolidation found. Also sheathing filler was found on the joint to within about 6" of the concrete surface.

(4) Some of the core holes show multiple delaminations with gaps between delaminatied surfaces of as much as 1".

(5) Many of the core holes had sheathing filler in them after coring, indicating that the delamination plane is continuous over areas other than those immediately around the sheath which was the source of the sheathing filler.

All of the tendons were detensioned to allow safe concrete removal. Strain, temperature, and deformation measurements were made at locations, along azimuth 256 degrees, during tendon detension. Strain was measured by electrical resistance strain gages installed before concrete placement. FIG. 3-4 shows strain gages located near the top and bottom of the dome at azimuth 256 degrees and radius 2'-6", 16'-5", 32'-5", and 45'-10", i.e., 4 locations near the top, and 4 locations near the bottom. Gages were oriented in the meridional and circumferential directions at each of the 8 locations. One meridional gage near the top, and one near the bottom, as well as one circumferential gage near the top and one near the bottom failed, leaving 12 active strain gages. Temperature was measured by thermocouples installed in holes drilled in the top and bottom of the dome, at radius 15'-0" and 43'-9", after concrete placement. Deformation measurements were manually made using a level and level rod.

It should be noted that FIG. 3-2 shows the contours of deepest delaminations, which showed no symmetry. Moreover, the gage locations along azimuth 256 did not cover the area with the deepest delamination of 15".

Results of the measurements are reported in section 3.4.

The cause of the delamination cannot be independently proven by the strain measurements [emphasis added]. Symptoms of unusual strain patterns are shown. The symptoms include the nonuniformity of strain at radii 2.5 and 46 feet (FIGS. 3-5 to 3-7 and 3-10 to 3-12). The measurements show a general trend to circumferential strains that are larger than meridional strains. They also show nonuniform strain patterns that are indicative of nonuniform force distribution in planes that are parallel to the shell middle surface and/or bending perpendicular to the middle surface.

Elevations at the dome apex were measured before placement of concrete; after completion of dome tendon post-tensioning; and after completion of dome tendon detensioning. The dome apex moved downward 1⅜"±⅛" as a result of dome post-tensioning and concrete dead load, shrinkage, creep and temperature change. The apex moved upward ⅞"±⅛" as a result of detensioning dome tendons, any creep recovery, and temperature changes. As expected, the upward movement of ⅞" was closest to ⅔" of movement predicted by calculations which assumed material elasticity and did not consider the effect of delaminations. Further, the small movements confirm that the effective prestress should be, as measured, within the range expected.

The small measurements and measurement differences, show that the cause of delaminations cannot be independently identified from the measurements [emphasis added]. They further show that the delaminations did not contribute significantly to the dome deformation.

Section 5.5 of the Analytical Investigation looked at unbalanced loads from prestressing. It begins with the statement:

A study was made to determine the force distribution on the dome due to the reported prestressing sequence. Each tendon group was divided into 2 zones giving a total of 6 zones. At various times, such as when 50% of the total tendons were tensioned, each zone was examined to determine the amount of normal pressure from the tensioned tendons within a particular zone. The normal pressures from each zone were then superimposed. Since the normal pressure from all the tendons being tensioned is approximately 100 psi, then the resulting pressure also indicates the percentage complete for a particular area. FIG. 5-4 shows the results for 40, 50 and 60% completion of prestressing. When 50% of the total tendons were tensioned, one area had effectively 73.8% of its total load whereas another area only had 28.4%.

In order to determine the effect of these unbalanced loads an analysis was performed for a homogeneous containment structure dome. The analysis did not include the effects of concrete cracking or construction joints. The dome was analyzed for the most severe case when the prestressing was 50% complete . . . .

The section concludes with the statement:

As indicated above the bending stresses are great enough, so that when combined with membrane stresses, the combined stresses at 50% loading are slightly higher than the stresses under full uniform loading. These loads are considered to be a contributor [emphasis added].

It should be noted that the table actually shows the bending stresses over three times higher for 50% unequal loading vs 100% uniform loading, i.e., 974 psi vs 300 psi for the meridional direction, and 660 psi vs 200 psi for the circumferential direction.

Section 5.6 of the Analytical Investigation looked at the construction joints.

In the analysis of why the delaminations occurred the construction joints deserved special attention because of the following:

(1) As shown by the coring results, the delaminations reached a maximum depth adjacent to the meridional construction joint.

(2) The delaminations appear to have some degree of symmetry about the meridional construction joint with a tendency to approach the surface as they progress away from the joint.

(3) Sheathing filler is present in the meridional construction joint indicating that separation existed.

In the model, the construction joints were simulated by hinges. It was shown that prestressing loads caused segments of the dome to rotate about the construction joints. The analysis concluded:

This analysis shows that the unbalanced load from post-tensioning together with rotating construction joints (eccentric thrust) would lead to large predicted stresses. These two items acting in conjunction with each other are considered the major cause for the concrete delamination [emphasis added].

Prestressed Concrete Containment Vessel Model

The Nuclear Power Engineering Corporation (NUPEC) of Japan, and the US Nuclear Regulatory Commission (NRC), Office of Nuclear Regulatory Research, co-sponsored and jointly funded a cooperative containment research program at Sandia National Laboratories (SNL). A 1:4-scale model of the Japanese Ohi-3 Pressurized Water Reactor Prestressed Concrete Containment Vessel (PCCV) was constructed and tested by SNL at Kirtland Air Force Base in Albuquerque, N. Mex. Nearly 1500 transducers were installed on the PCCV to monitor displacements, liner, rebar, concrete and tendon strains and tendon anchor forces. The instrumentation also included acoustic monitoring, video, and still photography. Pressure testing was conducted between September 2000 and Nov. 14, 2001—when it was filled with water and loaded to failure at 3.6 times the design pressure. A complete detailed report, *Overpressurization Test of a 1:4-Scale Prestressed Concrete Containment Vessel Model*, is incorporated by reference herein.

There were 98 hoop tendons, each of which went around the entire cylinder and anchored to one of two buttresses. There were 90 vertical tendons that went up the cylinder, over the dome, and back down the cylinder, i.e., the cylinder contained 180 tendon conduits. Thirty-four of the 188 tendons were instrumented with load cells. The tendons were tensioned, one at a time, according to a tensioning plan, between Mar. 10, 2000 and May 3, 2000.

A structural steel instrument frame was erected inside, before the containment building concrete was poured, to serve as a stable reference point for displacement transducers. Displacements were measured by Cable Potentiometers (CPOT), Linear Variable Differential Transformers (LVDT), and magnetostrictive transducers, all of which were referenced to the instrument frame or basemat.

Section 5.2.4 describes a Structural Failure Mode Test (SFMT) that was conducted at the conclusion of the experiments. The vessel was filled with water and pressurized to the point of failure. The first indications of failure were visible signs of wetting of the concrete surface, followed by acoustic noise which was interpreted as tendon wires breaking. Acoustic events were followed by water spraying and increasing frequency of acoustic events. Within 7 minutes of the first acoustic noise, the structure failed, as described in the report.

Pressurization of the model continued until a second spray of water was observed and suddenly, at 10:46:12.3, at an effective pressure of 3.63 $P_d$ (1.42 MPa or 206.4 psig), the PCCV model ruptured violently at ≈6 degrees azimuth near the mid-height of the cylinder. The rupture propagated in both directions and then radiated circumferentially about 2 m above the basemat, shearing off the cylinder wall. The dome and cylinder wall then came to rest on the instrument frame, which apparently prevented the model from toppling over. The entire collapse was over in slightly more than one second . . . .

Dramatic photographs of the failure and destruction are shown in FIGS. 5.34 and 5.35 of the report.

Crystal River Unit 3 Nuclear Power Plant

Crystal River Unit 3 was a 860 MW Babcock & Wilcox pressurized water reactor in Crystal River, Fla., operated by Progress Energy Florida, a subsidiary of Duke Energy. It was built for $400 million and commissioned in 1977. In a press release dated Feb. 5, 2013, it was announced that it would be retired, rather than repair cracks in the containment building estimated to cost between $1.49 billion and $3.43 billion.

Events leading to the initial cracks are well documented in United States Nuclear Regulatory Commission (NRC) *Special Inspection Report* 05000302/2009007, written by a Special Inspection Team (SIT), dated Oct. 12, 2010, which is incorporated by reference herein. The Executive Summary states:

Crystal River shut down for a planned refueling outage on Sep. 26, 2009. One of the major work activities planned for this outage was a steam generator replacement. In order to take the old steam generators out and put the new steam generators in, the licensee created a construction opening in the side of the containment building. On Oct. 2, 2009, while creating this opening, workers saw that there was a gap, or separation, affecting the outer layer of concrete of the building wall. The gap or separation in the concrete has been commonly referred to as a delamination.

The Executive Summary continues to state:

The licensee's investigation concluded that the delamination was caused during the creation of the opening in containment. As part of preparing the containment building for making the opening, tendons in the containment building were detensioned. The main cause of the delamination was attributed to the scope and sequence of this tendon detensioning [emphasis added]. Tendon detensioning began after the plant was shut down in Operating Mode 5, when containment operability was not required.

The licensee commissioned Performance Improvement International (PII) to conduct a root cause assessment. A 268 page non-proprietary version of the 15 member PII team report, dated Aug. 10, 2010, is included as Enclosure 3 of the October 12 NRC report. FIG. 3.1 shows that Crystal River is one of 35 US containment buildings using a similar design (including Turkey Point Unit 3), i.e., post-tensioned concrete cylinder with steel liner. The report includes a summary of the main design features of the containment wall.

The wall is 42 inches thick with a ⅜" steel liner on the internal surface. Approximately 10 inches into the concrete on the outside, the horizontal tendons (sleeve OD is 5.25 inches) each typically provides about 1400 kips of force (hoop tendon) to post-stress the concrete wall. Just inside the horizontal tendons are the vertical tendons.

There are a total of 94 horizontal tendons in the containment wall which covers one-third of the circumference for a total of 282 tendons. Each tendon has a near neighbor 13" away and a far neighbor on the other side 26" away. Each tendon has a length of ⅓ of the circumference of the containment from one buttress past one buttress to the next buttress. Buttress #1 is facing north and buttress #2 is at WNW 60 degrees counter-clockwise.

The remaining buttresses are numbered sequentially. Each of the six wall segments are located between two buttresses. Thus bay 34 lies between buttress 3 and buttress 4. Horizontal tendon 42H21 runs between buttress 4 and buttress 2 and is the 21st tendon going up from 42H1 at the bottom of the containment wall. Bay 34 also has 53H21 which is the other tendon in the set.

FIG. 1.5 is a sketch of the containment structure unfolded. It shows that the buttresses extend from elevation 90' to elevation 250'

The Executive Summary concludes:

Crystal River Unit 3 (CR3) is unique in that no other plants that have cut openings in their containments have experienced similar delamination. As discussed above, the root cause analysis determined that delamination was caused by scope and sequence of this tendon detensioning in preparation for making the opening. The Licensee developed new analytic methods to adequately identify the redistribution of stresses in the containment wall and identify an acceptable expanded detensioning scheme to perform the repair [emphasis added]. The licensee has been communication to other plants, through the INPO and other industry organization, lessons learned from the event.

The design is summarized in the BACKGROUND of the report, which states:

. . . The Crystal River containment structure is a steel lined post-tensioned cylindrical concrete structure of about 157 feet in height with an outside diameter of about 138 feet. The containment has 42-inch thick concrete walls and has a flat foundation mat and a shallow torispherical dome. Post-tensioning is achieved by utilizing an outer array of horizontal tendons immediately adjacent to an inner array of vertical tendons that are embedded in the walls about 15 inches from the outside surface. Tendons are also provided in the dome. In addition, steel rebar is embedded in the concrete walls at the outside surface and at other locations.

. . . The dome is post-tensioned by 123 tendons that are arranged in a three-way (layer) configuration and are anchored to a ring girder. The containment walls include 282 horizontal and 144 vertical tendons that are anchored to 6 vertical buttresses equally spaced circumferentially around the containment. Each tendon consists of numerous small diameter wires, which are greased and housed inside a conduit. The conduit for each tendon is about five inches in diameter and is made of galvanized steel. The concrete has a minimum 28-day compressive strength of 5,000 pounds per square inch (psi).

The BACKGROUND also summarized an earlier delamination problem with the dome.

On Apr. 14, 1976, about two years after completion of concrete placement of the containment dome and one year after tensioning the tendons, electricians were attempting to secure drilled-in anchors to the top surface of the dome and certain anchors would not hold. Upon further investigation a delamination in the containment dome was discovered. The area of the delaminated concrete was approximately circular in shape with a 105-foot diameter. The approximate thickness of the delamination was 15 inches, with a maximum gap of approximately two inches between layers. No cracks appeared on the dome surface and, except for springiness when walking on the dome, there were no indications of any problems [emphasis added].

. . . The dome investigation team concluded that a compression-tension interaction failure had occurred. The dome delamination was caused by the effects of radial tensile stresses combined with biaxial compressive stress and lower-than-normal concrete tensile strength and aggregate strength [emphasis added] . . . .

The dome repair included: removal of the delaminated dome cap; meridional, hoop, and radial reinforcement; and placing of a new dome cap. Instrumentation was installed to monitor the dome during tendon detensioning, retensioning and during a structural integrity test. The structural integrity test subjected the repaired containment to 115 percent design.

Section 1.0 of the report describes problems encountered when cutting a 25 foot wide by 27 foot high construction opening in the bay between buttresses #3 and #4, approximately forty feet above the equipment hatch.

The licensee began Refueling Outage 16 on Sep. 25, 2009 with a reduction in power mode 1. The unit continued down in power through Modes 2, 3, 4, and 5 on September 26. Upon reaching Mode 5 at about 5:00 μm. on September 26, tendon work activities began. Two vertical tendons (34V12 and 34V13) were detensioned simultaneously. These tendons were detensioned prior to cutting the button heads. From September 26 through October 1, eight additional vertical tendons and seventeen hoop tensions were detensioned by plasma cutting the button heads as part of the process to make the required construction opening. The licensee began the removal of concrete by hydrolazing (hydro-demolition) on Sep. 30, 2009, as the first step in making the construction opening. This process was accomplished by using water under pressure (as great as 25000 psi) to "cut" the concrete. On October 3, during hydro-demolition work to expose the first layer of tendon sheaths, water from the work was observed leaking from the exterior surface of the containment at various locations below the elevation of the bottom of the construction opening [emphasis added]. The leaking water was not limited to the construction opening, but was observed at the edges of the construction opening extending into undisturbed concrete for an indeterminate distance but at least as far as the post-tensioning buttresses (Buttresses #3 and #4). As the work continued, some of the concrete rubble unexpectedly broke off into large pieces. Licensee personnel inspected the construction opening and discovered a concrete separation condition. It was located approximately in the cylindrical plane of the centerline of the hoop tendons, approximately nine to twelve inches from the exterior surface of the containment building. Approximately 30 inches of concrete remained in apparent good condition all the way to the liner plate. The hydro-demolition of the concrete continued through October 7, when the containment building liner was exposed and all concrete had been removed down to the liner.

Section 5.1b describes observations of non-destructive testing that was conducted.

The licensee contracted CTLGroup to perform the non-destructive testing (NDT) in support of the analysis to determine the extent of the condition associated with the delamination. CTLGroup's main objective was to characterize the extent of the delamination around the opening, and assess whether similar delamination existed elsewhere within the wall structure. CTLGroup performed initial trial testing to evaluate suitability of several NDT techniques in detection of the delamination in the containment wall structure. A test procedure/program was developed for the selected methods. Impulse Response (IR) was selected as the most suitable method for detecting a delamination consistent with the delamination of Bay 3-4 [emphasis added]. Documentation was provided related to quality control, safety training, qualification requirements, and equipment calibration.

The SIT reviewed the licensee's information on the NDT that was performed at all accessible areas, including nearly all of the exposed exterior containment building wall surface, portions of wall areas accessed inside adjacent building, and a portion of the containment dome . . . . The expansive scope of this IR testing over the containment surface provided assurance that sufficient testing has been performed to detect delamination similar to what has been observed between Buttresses 3 and 4.

Section 5.1b continues to explain the IR test methods.

The IR test method employs a low strain transient impact, generated by a hammer, to send a stress wave into the concrete structure. The resulting bending behavior of the structure is analyzed to characterize the integrity of the structure. The IR analysis produces an average mobility, which is the principal parameter. Presence of significant voiding or an internally delaminated or unbounded layer will result in an increased average mobility value. On the other hand, a sound concrete element without distress will produce a relatively low average mobility value. The presence of delamination will effectively reduce the thickness of wall or slab responding to the impact, which results in a drastically increased average mobility value.

The results of the IR testing around the Steam Generator Replacement (SGR) opening and other bays were described as follows.

Bay 3-4 was found to have large delamination with an hour glass shape centered at the SGR opening. The delamination was concluded to be within an area of approximately 80 ft by 60 ft, extending between the edges of the two buttresses in horizontal direction, and from the top of the equipment hatch opening to approximately ten feet below the ring girder in the vertical direction. Average mobility values exceeded the potential damage threshold in the delaminated area. Based on core sampling and boroscope examination of core holes, the depth of delamination ranged from three to ten inches, with an average delamination depth between seven and eight inches from the exterior face. The delamination appeared to be in the plane of the hoop tendons. The extent of the delamination was confirmed by the core samples and boroscope examination.

The remaining five bays were found to have sound concrete, based on IR test results [emphasis added]. Significant delamination similar to that noted in Bay 3-4 was not found in other areas of the containment wall structure . . . .

Section 8.0 of the report includes generic issues for the industry. In particular:

Some of the contributing causes (such as high radial tension without radial reinforcement, stress concentrations around the tendon sleeves, etc.) may be inherent in the containment designs of many post-tensioned plants, and therefore, licensees should be aware of the potential adverse effects of these conditions when evaluating potential containment modifications that involve detensioning tendons. From the licensee's root cause analysis, it appears that standard industry analysis tools typically used for predicting radial tension may be limited in their ability to predict the potential delamination failures for major modification activities, such as the creation of SRG construction openings that involve detensioning of tendons [emphasis added].

Progress Energy put together a nice slide presentation of the investigation, *Crystal River Unit #3 Containment Delamination Update*, Nov. 20, 2009, which is incorporated by reference herein.

Subsequent to the Oct. 12, 2010 NRC Special Inspection Report, the licensee made repairs to the delamination in Bay 3-4. Section 9 of the PII report in Enclosure 3 of the Oct. 12, 2010 NRC report included RECOMMENDATIONS TO PREVENT RECURRENCE. Items B and C are particularly relevant to the invention.

B. Repair to De-Tensioning Analysis

In March, 2010 it was necessary to de-tension bay 34 so that delaminated concrete could be removed and replaced. As such, this represented the conditions addresses in recommendation items A and C. The specific action for this topic (B.1) was performed prior to de-tensioning and it is included here to maintain consistency between this report and Progress Energy assessment.

B.1 Perform a detailed analysis of the tendon de-tensioning plan in support of the containment repair effort. Modify the plan as necessary and ensure the stresses show positive margin as validated using CR3 delamination data. (Performed successfully in March, 2010).

C. Re-Tensioning Containment in R 16

Delamination is typically associated with the process of changing tendon tension on a large scale so the upcoming re-tensioning of the containment is relevant [Emphasis added].

C.1 Perform a detailed analysis of the tendon re-tensioning plan in support of the containment repair effort. Modify the plan as necessary and ensure the stresses show positive margin as validated using CR3 delamination data.

Better Actions

C.2 Monitor displacement of the RB walls during re-tensioning to confirm the building response relative to computer prediction [emphasis added].

C.3 Monitor the RB wall with strain gauges and acoustic instruments during retensioning to ensure responses are within established limits per the repair design documents.

On Mar. 14, 2011, during the final stages of the re-tensioning process, the licensee had indication that a new delamination occurred in Bay 5-6 of the containment structure, i.e., between buttresses 5 and 6—which is separated from the repaired Bay 3-4 by Bay 4-5. Details are provided in NRC Report 05000302/2011009, dated May 12, 2011, which is incorporated by reference herein. The Background states:

The licensee's containment building repair plan included: (1) additional detensioning of containment; (2) removal of delaminated concrete; (3) installation of reinforcement, including radial reinforcement through the delaminated plane; (4) placing of new concrete; (5) retensioning containment; and (6) post-repair confirmatory system pressure testing. In early 2011, the licensee had completed repair steps 1 through 4 and was in the process of retensioning the containment. On Mar. 14, 2011, during the final stages of the re-tensioning process, the licensee had indications that a new delamination occurred in Bay 5-6 of the containment structure.

The May 12, 2011 report continued to detail the events of Mar. 14, 2011.

On the afternoon of Mar. 14, 2011, the licensee had completed the first retensioning sequence (Sequence #100, Hoop Tendons 42H41, 62H41, and 64H41) of the final pass (Pass #11). Per procedure, the licensee was waiting for the containment building to stabilize before beginning the next sequence and monitoring the structural behavior of the containment building via acoustical emissions monitors and strain gages, specifically placed at various points of the structure to detect any abnormal/unexpected response to tendon retensioning. During this monitoring period, the strain gages indicated an increase in strain and then failed high, and the acoustic monitors indicated a high level of acoustic activity in the bay bordered by Buttresses #5 and #6 (Bay 5-6). The phenomenon reportedly lasted for about twenty minutes. The licensee conducted impulse responsive (IR) non-destructive examination NDE techniques to determine the condition of the wall in Bay 5-6. The IR scans of the bay determined that there were numerous indications consistent with a delamination. By the end of the inspection period, the licensee had determined that the delamination was extensive in Bay 5-6 and was continuing to evaluate the condition of the entire containment structure. Future inspection activities by the NRC relating to the Mar. 14, 2011, event are to be determined.

Bechtel Power Corporation and URS Corporation developed plans to repair the containment building. Option 10 was to replace all concrete in all bays above elevation 150', except Bay 3-4, and install radial anchors below elevation 150', i.e., replace between elevation 150' and elevation 250', and install anchors between elevation 90' and elevation 150'. Duke Energy made a statement of plans for additional repairs in a press release dated Jun. 27, 2011, which is incorporated by reference herein. The press release states:

Progress Energy engaged outside engineering experts to perform an analysis of possible repair options for the second delamination. The consultant analyzed 22 potential repair options and ultimately narrowed those to four. Progress Energy, along with independent experts, reviewed the four options for technical, constructibility, and licensing feasibility as well as cost.

Based on that initial analysis, the company selected the best repair option. The option would entail systematically removing and replacing concrete in the containment structure walls. The planned option does not include the area where concrete was replaced during the initial repair. The preliminary cost estimate for this repair is between $900 million and $1.3 billion.

On Jul. 26, 2011, an area of concrete measuring about 3 to 4 feet wide by 12 feet long and 1 inch thick fell from Bay 1-2, i.e., between Buttresses 1 and 2. Note that this was the third of the six bays to experience delamination, and the three bays were equally spaced around the circumference of the containment building, i.e., Bay 3-4 (first), Bay 5-6 (second), and Bay 1-2 (third) experiencing delamination; and Bay 4-5, Bay 6-1, and Bay 2-3 apparently remaining intact—although no additional testing of those bays was recited. Details are documented in NRC Integrated Inspection Report 05000302/2011004, dated Oct. 26, 2011, which is incorporated by reference herein. Section 4OA5.2a states:

On Jul. 26, 2011, acoustical monitors indicated a high level of acoustic activity in Bay 1-2. The initial licensee inspection found that an approximately 1 inch thick piece of concrete had fallen from Bay 1-2 onto the intermediate building 119' elevation. The falling concrete had no adverse effect on safety-related equipment. The area of spalled concrete measured about 3 to 4 feet wide by 12 feet long. Additional inspections found surface cracks at higher elevations above the intermediate building adjacent to buttresses 1 and 2. Non-destructive examination using impulse response testing was used to determine the condition of the concrete. At the close of this inspection period, impulse response testing of Bay 1-2 had not been completed, but numerous indications consistent with cracking or delamination within the concrete wall of Bay 1-2 had been detected [emphasis added]. Those delaminations appeared to have propagated in a plane parallel to the surface of the containment wall. At the end of the inspection period, the licensee had installed temporary radial anchor bolts in Bay 1-2 to prevent the propagation of the delamination. The inspectors observed the installation of several anchor bolts to verify that the work was properly conducted per approved work documents.

The report continued:

During the inspection period, the licensee detensioned all the vertical tendons to 75 percent tension. The licensee determined that this partial detensioning would reduce stress in the reactor building concrete and would add additional margin to any further delamination events . . . .

Duke Energy commissioned an independent technical review by Zapata Inc. in March 2012, which was reported in a press release dated Oct. 1, 2012. The cover letter to the Florida Public Service Commission, the table of contents, and the executive summary of the 994 page report are incorporated by reference herein.

The review found that the current repair plan appears to be technically feasible, but significant risks and technical issues still need to be resolved, including the ultimate scope of any repair work. The Zapata report estimated the repair cost at approximately $1.49 billion. Progress Energy's prior assessment indicated expected repair cost of $900 million to $1.3 billion, with the cost trending up.

The report confirmed, as Progress Energy's assessment had indicated, that an increase in the scope of repairs will increase the cost and extend the schedule.

Zapata also prepared approximate estimates for more extensive work based on potential unplanned scenarios, up to and including its worst-case scenario. This scenario assumed that the company would perform Progress Energy's more limited scope of work, and at the conclusion of that work, additional damage would occur in the dome and in the lower elevations, which would force replacement of each. Under the worst-case scenario, Zapata estimated that the cost would be $3.43 billion with a 96 month schedule.

Four months later, Duke Energy announced the decision to retire the plant in a press release dated Feb. 5, 2013, which is incorporated by reference herein.

"We believe the decision to retire the nuclear plant is in the best overall interests of our customers, investors, the state of Florida and our company," said Jim Rogers, chairman, president and CEO of Duke Energy. "This has been an arduous process of modeling, engineering, analysis and evaluation over many months. The decision was very difficult, but the right choice."

Concrete Inspection Techniques

Various methods have been used to evaluate concrete structures. U.S. Pat. No. 5,633,467 Apparatus and method for non-destructive testing of structures to Paulson, which is incorporated by reference herein, discloses an apparatus using a laser interferometer to measure deflection of concrete under load. The most widely accepted method for detecting delaminations in concrete is by dragging a chain across the concrete and listening for changes in the sound. This is specified in ASTM Standard D4580/D4580M, *Standard Practice for Measuring Delaminations in Concrete Bridge Decks by Sounding*. U.S. Pat. No. 5,180,969 Detection of reinforcing steel corrosion in concrete structures using non-linear harmonic and intermodulation wave generation to Kwun et al., which is incorporate by reference herein, discloses the use of electromagnetic signals inducing signals in rebar which generates harmonic frequencies that depend on rust. U.S. Pat. No. 5,814,731 Ultrasonic scanning apparatus for nondestructive site characterization of structures using a planar based acoustic transmitter and receiver in a rolling pond to Alexander et al., and U.S. Pat. No. 6,581,466 Acoustic inspection of structures to Costley et al., both of which are incorporated by reference herein, disclose variations of ASTM D4580. U.S. Pat. No. 6,119,526 Method and apparatus for detecting tendon failures within pre-stressed concrete to Reigstad et al., which is incorporated by reference herein, discloses use of a metal sensor to detect rebar. U.S. Pat. No. 8,285,495 Corrosion inspection and monitoring system to Purekar et al., which is incorporated by reference herein, discloses the use of high frequency sound to detect corrosion of rebar. U.S. Pat. No. 8,953,153 System and method for post-tensioned tendon monitoring to Wall, which is incorporated by reference herein, discloses optical strain gages to monitor post-tensioned tendons. US 2004/0035218 Monitoring of concrete vessels and structures to Paulson, which is incorporated by reference herein, discloses the use of acoustic emission.

An extensive review of nondestructive examination techniques is included in, *Inspection of Nuclear Power Plant Structures—Overview of Methods and Related Applications*, which is incorporated by reference herein. Section 3 covers, Review of Methods for Detection of Degradation in Nuclear Power Plant Concrete Structural Members. This includes:
3.1.1 Nondestructive Testing
   3.1.1.1 Visual Inspection
   3.1.1.2 Acoustic/Stress Waves
   3.1.1.3 Nuclear/Radiographic Techniques
   3.1.1.4 Electromagnetic
   3.1.1.5 Infrared Thermography
   3.1.1.6 Audio
   3.1.1.7 Rebound Hammer
   3.1.1.8 Fluid Penetrability
   3.1.1.9 Concrete Moisture Content
   3.1.1.10 Laser-Induced Breakdown Spectroscopy Section 5 is a Review of Applications of Nondestructive Evaluation (NDE) To Thick-Section Reinforced Concrete Structures.

General Inspection Techniques

There is a lot of prior art teaching of general inspection techniques. The use of vibration analysis is particularly popular. The following patent publications represent an overview of vibration analysis due to active excitations.

U.S. Pat. No. 4,128,011 Investigation of the soundness of structures to Savage. U.S. Pat. No. 5,195,046 Method and apparatus for structural integrity monitoring to Gerardi et al. U.S. Pat. No. 6,006,163 Active damage interrogation method for structural health monitoring to Lichtenwalner et al. U.S. Pat. No. 6,192,758 Structure safety inspection to Huang. U.S. Pat. No. 6,257,064 Wave speed bridge damage detection method to Durón. U.S. Pat. No. 7,596,470 Systems and methods of prognosticating damage for structural health monitoring to Kim. U.S. Pat. No. 7,647,206 System and method for monitoring structures for damage using nondestructive inspection techniques to Ford. U.S. Pat. No. 7,584,075 Systems and methods of generating diagnostic images for structural health monitoring to Kim. U.S. Pat. No. 7,672,793 Method for calculating probabilistic damage sizes in structural health monitoring systems to Beard. U.S. Pat. No. 8,176,800 Method for determining tension in a rod to Cesare et al. All ten of which are incorporated by reference herein.

The following patent publications represent an overview of vibration analysis due to ambient excitations and ultrasound. U.S. Pat. No. 4,549,437 Acoustic testing of complex multiple segment structures to Weins et al. U.S. Pat. No. 5,948,984 Structural integrity recovery system to Hedberg. U.S. Pat. No. 6,779,404 Method for vibration analysis to Brincker et al. U.S. Pat. No. 7,228,240 Device and method for determining and detecting the onset of structural collapse to Duron et al. U.S. Pat. No. 7,623,974 System and method for detecting onset of structural failure to Cipra. US 2008/0059086 System and method for determining and detecting stability loss in structures to Duron et al. All six of which are incorporated by reference herein.

Most vibrations are measured by accelerometers or strain gages. However, some use lasers to measure displacement, along a single axis, of retroreflective targets attached to a structure. Examples include the following. U.S. Pat. No. 6,240,783 Bridge monitoring system to McGugin et al. U.S. Pat. No. 6,915,217 Laser doppler vibrometer for remote assessment of structural components to Springer, III et al. U.S. Pat. No. 7,667,827 Systems and methods for remote monitoring of vibrations in machines to Nelson et al. All three of which are incorporated by reference herein.

Some applications measure tilt and deflection. Examples include the following. U.S. Pat. No. 4,480,480 System for assessing the integrity of structural systems to Scott et al. U.S. Pat. No. 5,841,353 Relating to the determination of verticality in tall buildings and other structures to Chisholm et al. U.S. Pat. No. 5,850,185 Deflection monitoring system to Canty. U.S. Pat. No. 5,657,003 Structure movement monitoring and emergency alarm system to Fuentes. U.S. Pat. No. 8,830,477 Method for determining loads on a mechanical structure and the resultant damage to Schreiber et al. All five of which are incorporated by reference herein.

Some applications measure strain or crack growth at discrete locations. Examples include the following. U.S. Pat. No. 7,637,166 Monitoring system for concrete pilings and method of installation to Hecht et al. U.S. Pat. No. 8,091,432 Monitoring system for concrete pilings and method of installation to Hecht et al. U.S. Pat. No. 8,510,061 Methods, systems, and computer readable media for wireless crack detection and monitoring to Grant et al. All three of which are incorporated by reference herein.

Examples of software include the following. U.S. Pat. No. 7,006,947 Method and apparatus for predicting failure in a system to Tryon, III et al. U.S. Pat. No. 7,024,343 Method for calibrating a mathematical model to El-Ratal. U.S. Pat. No. 7,546,224 Method for assessing the integrity of a structure to Campbell. All three of which are incorporated by reference herein.

Shortcomings of the Prior Art

Vibrational analysis inherently integrates all components of the structure into a few vibrational measurements, e.g., a shift in loading anywhere in the structure, or a change in the mechanical properties of the structure, produces a change in vibrational modes. For example, if a bit of metal is filed off a tuning fork, the frequency will change. If any of the metal is annealed, the frequency will change. If the tuning fork corrodes, the frequency will change. The problem is that analysis of the data is very complex, and may not point to suspect areas for follow-up human inspection.

Strain measurements are localized measurements and therefore require a large number of transducers to map a civil structure. For example, typical resistance strain gages are less than 1 inch in length and the sensitivity is along the direction of the wires. Arrays are arranged in patterns, such as a rosette, to measure in two directions, but measurements are limited to a plane, i.e., they don't measure strain in three dimensions. Moreover, bonding of the strain transducers to the structural elements may make retrofitting an existing structure, or replacement of embedded transducers, difficult, i.e., preexisting strain is unmeasurable when the gage is bonded to a structural member, so absolute strain can not be measured by a replacement gage. The incremental cost for additional measurement points is approximately linear with the number of points. The most significant problem is that analysis requires extrapolation of the localized measurements of a large number of transducers to model the structure.

Hydrostatic testing has been shown to be unreliable for detecting fatigue cracks in railroad tank cars. Visual inspections, ultrasonic, magnetic particle, acoustic emission, radiographic, leak, and other traditional nondestructive testing techniques are useful, but in need of additional techniques to augment conventional measurement capabilities.

From the high-profile cases described hereinabove, it is clear that the instrumentation to predict failures in post-tensioned and detensioning concrete is totally inadequate.

It is somewhat disconcerting to think that the structural integrity of structures such as bridges and nuclear power plant containment buildings is determined by listening to the sound of impact hammers and chains being dragged across the surface. Moreover, it is of some concern that the first indications of a problem are when a tendon pulls out of the concrete, a loud bang is heard, water or grease leaks out of what is though to be a solid wall, concrete anchors don't hold, the concrete "feels spongy" under workers feet, pieces of a thick concrete dome spontaneously fall off, etc.

Luckily none of these incidents were under full load at the time. What if the tendons had not pulled out of the bridges during construction—but while in use? What if the delaminations in the nuclear containment buildings occurred during an accident when the containment building was under the pressure it was intended to hold? The initial Crystal River incident, and the subsequent incidents following detailed engineering analysis, causes some concerns as to the level of understanding of these complex structures by the leading experts in the field.

Need Fulfilled by the Invention

Direct measurements of the coordinates of a structure at cardinal points which provide unambiguous indications as to the health of the structure are needed. This can be achieved by incorporating advances in Electronic Distance Measurement (EDM) to Structural Health Monitoring. A significant advantage is that the large capital investment for instrumentation and software is a one-time expense which can be shared over hundreds of structures, while the incremental cost for additional cardinal points on the structure is small.

The only known proposal of EDM using trilateration for Structural Health Monitoring is described in *Measurement Program for the Green Bank Telescope*, Hall et al, SPIE Conference on Advanced Technology MMW, Radio, and Terahertz Telescopes, Kona, Hi., March 1998, SPIE Vol. 3357, which is incorporated by reference herein. This proposal was not reduced to practice, and was limited to the specific case of a radio telescope rotating in azimuth and elevation. The project was abandoned in 2004, when the management of the National Radio Astronomy Observatory (NRAO) and an advisory committee decided it was not needed, and the necessary measurements could be obtained by astronomical pointing measurements made by the telescope, i.e., the methods traditionally used to point radio telescopes-including the collapsed 300 Foot Radio Telescope the $75 million Green Bank Telescope replaced.

As illustrated by the recited case histories, there is a long-felt but unresolved need to prevent civil structural failures in order to protect life and property. It would therefore be desirable and advantageous to address the problems of Structural Health Monitoring and to obviate shortcomings in the prior art by bringing the advantages afforded by modern Electronic Distance Measurement instrumentation to the problem.

BRIEF SUMMARY OF THE INVENTION

Electronic Distance Measurement is used for Structural Health Measurement and Nondestructive Testing of civil structures, pressure vessels, and the process of prestressing concrete. An architecture for making electronic distance measurements from at least three locations and converting the distances to (x,y,z) coordinates is described. Data analysis examples are described for a bridge, including applications to historic bridge collapses. An example of how a finite element model may be verified against experimental measurements is given. An example of how experimental measurements may be used to check characteristic behavior as an indicator of structural health is given. Examples of measurements for bridges, cranes, containment buildings, and railway tank cars are given.

BRIEF DESCRIPTION OF THE DRAWINGS

FIG. 12A shows an erected box girder bridge.

FIG. 12B shows a detail of a box girder bridge.

DETAILED DESCRIPTION OF THE INVENTION

Electronic Distance Measurement

Figure 1:
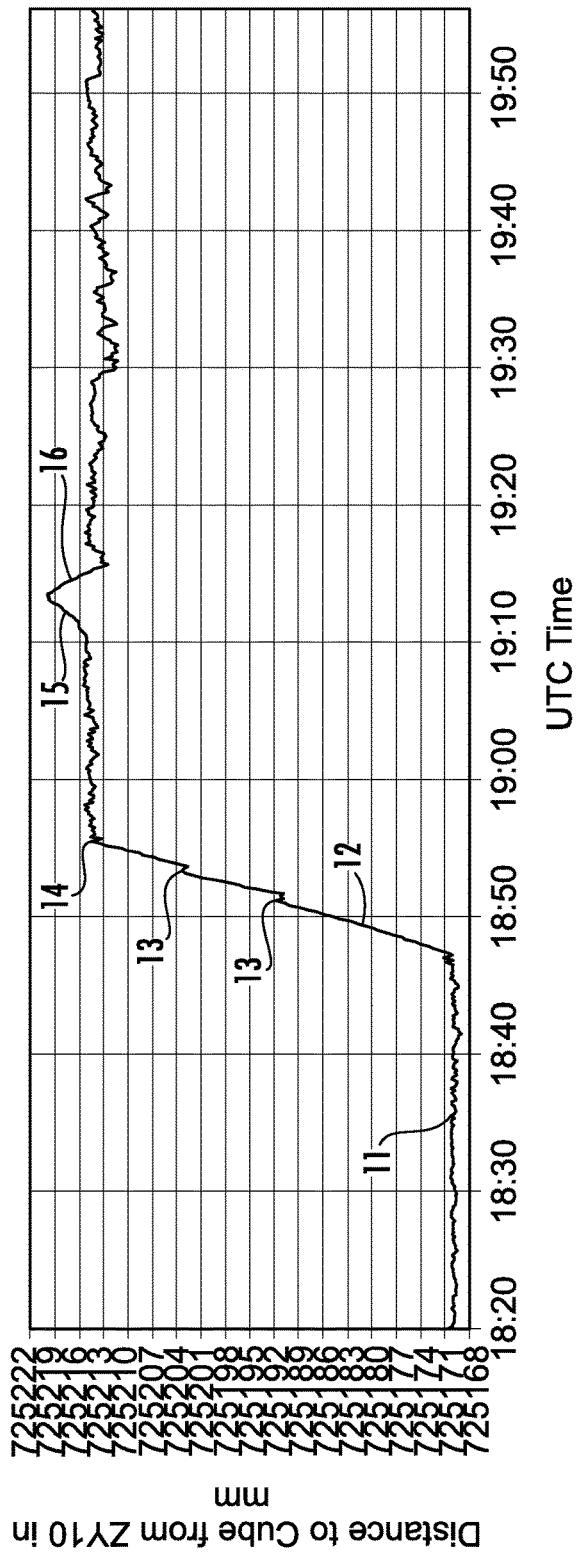
FIG. 1 is a plot of prior art EDM measurements of a crane deflections.

The most common surveying instrument used by Civil and Structural engineers is the Total Station. The early history of the introduction of the Total Station is not clear. Chapter 5 of *The Surveying Handbook*, second edition, Brinker and Minnick, 1995, credits Hewlett-Packard with inventing the name total station for the Model 3810A, which was introduced in the April 1976 edition of HEWLETT-PACKARD JOURNAL, both of which are incorporated by reference herein. This was disclosed by Hewlett-Packard Company in U.S. Pat. No. 4,113,381 Surveying instrument and method to Epstein, as filed in 1976 and incorporated by reference herein.

Chapter 1 of *Electronic Distance Measurement*, third edition, Rüeger, 1990, incorporated by reference herein, cites the Zeiss Reg ELTA 14 as the first Total Station introduced in 1970, and the AGA Geodimeter 700 as the second in 1971. In an article in the April 2003 issue of Professional Surveyor Magazine, incorporated by reference herein, Marc Cheves recounts a claim by former employees of Zeiss and Geodimeter that both introduced the total station at the same show in 1971, i.e., the Zeiss Reg ELTA 14 and the AGA Geodimeter 700. Cheves goes on to say "My first experience with the term total station, (as was the experience of many other surveyors in the United States), was associated with Hewlett Packard."

As explained in Chapter 4 of *The Surveying Handbook*, prior to the total station, surveyors measured distance by steel or invar tapes, which required corrections for slope, temperature, catenary curve, and tension. Distances were also measured optically by stadia tacheometry. By measuring the angle subtended by a known length, such as a stadia rod or subtense bar, distance could be determined using a theodolite to measure angles. The total station combined distance and angle measurements into one instrument.

The total station incorporates electronic distance measurement with measurement of two angles, as well as automatic electronic compensation for mechanical level errors. Typical uncertainty is around 1 arc second for angles and 3 mm for distance under ideal conditions. Total stations operate at ranges up to several kilometers, with large target arrays. Measurements are made by a surveyor sighting through a telescope to measure the angles and pressing a button to initiate a distance measurement, which typically takes several seconds to complete. Beginning around the year 2000, total stations began being automated, and now totally automatic instruments with automatic tracking for angle measurements are available. Due to the nature of the applications for total stations, there has not been a driving need to reduce the distance error or increase the speed of measurement. Compared to the prior art of pulling measuring tapes, the speed and accuracy of even a modest performance total station is almost overkill for the construction industry. Few construction projects require distance accuracies less than 5 mm or measurement speeds faster than a few seconds. For reasons that will be discussed in detail hereinbelow, the uncertainty of single instrument measurements using angle measurements are still too large for structural health monitoring of many stiff structures, which undergo small deformations under load.

In a parallel path to the development of the Total Station for surveying, Hewlett-Packard introduced the HP 5525A laser interferometer in 1971. This quickly became the length standard for machine shops and metrology labs. A major limitation was that the retroreflector target had to be carefully controlled while moving from a starting point to an end point down a static laser beam in order to measure the differential distance. This was easy enough for machine movements and laboratory environments, but almost impossible across a shop floor or field. Typically, a temporary straight track had to be constructed and a trolley translated the retroreflector down the beam.

U.S. Pat. No. 4,457,625 ('625) Self calibrating contour measuring system using fringe counting interferometers to Greenleaf et al., filed in 1981; U.S. Pat. No. 4,621,926 ('926) Interferometer system for controlling non-rectilinear movement of an object to Merry et al., filed in 1985; U.S. Pat. No. 4,714,339 ('339) Three and five axis laser tracking systems to Lau et al., filed in 1986; and U.S. Pat. No. 4,790,651 ('651) Tracking laser interferometer to Brown, et al., filed in 1987; all disclosed tracking laser interferometers that were developed under various US Government sponsored programs to develop higher accuracy three-dimensional measurement capabilities, all four of which are incorporated by reference herein. Tracking laser interferometers incorporated a control system to automatically track a retroreflector by moving the beam to follow the retroreflector, which allowed an operator to simply carry the retroreflector between points. Operation and performance of an early instrument is described in Stanford Linear Accelerator Center publication SLAC-PUB-5847, incorporated by reference herein.

It will be understood by those skilled in the art that a laser interferometer inherently measures the phase of a light signal and is thus limited to integrating distances from a starting point to an end point to measure a differential length. There is no inherent "zero" reference for an interferometer. For that reason, laser trackers include a "home" location fixed to the instrument housing which is used to reference measurements to a reference point at the intersection of the azimuth and zenith axes. A significant advantage of the laser tracker is that the interferometer is fast, which allows the laser tracker to make dynamic measurements at over 1 kHz—in contrast with the total station which operates at fractions of a Hz.

Due to the metrology lab and interferometer heritage, laser trackers were developed for the most demanding dimensional metrology applications. Emphasis was placed on accuracy over working distance, since most applications were in machine shops, optics shops, metrology labs, scientific experiments, accelerators, etc. For the most part, total stations and laser trackers developed independently along parallel lines for different applications, i.e., total stations for longer range less accurate surveying and laser trackers for shorter range higher precision metrology.

In October 2004, FARO Technologies introduced the FARO X, a laser tracker architecture (without the interferometer) that adopted absolute distance measurement capabilities—like total stations—but retaining the emphasis on short range accuracy and fast measurement speed. Even though most laser trackers are no longer limited to tracking laser interferometers, the instruments are still called by the legacy name "trackers" to distinguish them from less accurate, and slower, total stations-which now also track targets in order to eliminate the operator at the instrument. Absolute distance measurement-unlike interferometers-enables the instrument to freely switch between targets as needed. This is a critical requirement for structural health monitoring applications.

Commercial laser tracker instruments are available from FARO Technologies, Inc., Lake Mary, Fla., Leica AG, Heerbrugg, Switzerland, and Automated Precision Inc. (API), Rockville, Md., that could (and most surely will) be adapted for the purpose of structural health monitoring. Laser trackers, using absolute distance measurement, have distance measurement accuracies of the order of 1 part per million, but suffer from the same inherent weakness in angle measurements as theodolites and total stations of around 1 arc second, or 5 parts per million-under ideal conditions.

To put 1 part per million in perspective, 1 ppm in 100 meters is 0.100 mm, 100 microns ($\mu$m), or 0.004 inches. This is the thickness of a sheet of standard 20 pound printer paper. The accuracy for differential measurements, such as the delta between two points, is typically around 10 $\mu$m or better. In contrast, the most common instrument used by a machinist in a machine shop for precision measurements is a micrometer—in fact the micrometer is the iconic symbol for high precision measurement. A typical micrometer has an accuracy of 0.000 050 inch, i.e., for a 1 inch micrometer, the accuracy is 50 parts per million. Stated another way, EDM measurements with an accuracy of 1 ppm for large-scale metrology measurements is proportionally 50 time more accurate than measurements made by a micrometer in a machine shop.

Such high accuracy presents practical problems for field calibration of these instruments, i.e., there are no better instruments to check them against. A practical test method which detects a number of common problems is disclosed in U.S. Pat. No. 7,856,334 Method for calibrating a laser-based spherical coordinate measurement system by a mechanical harmonic oscillator to Parker, incorporated by reference herein.

Previously available commercial Laser trackers were limited in range to under 100 meters—although there is no inherent limitation that prevents them from being extended to several kilometers, as will be shown in experimental data hereinbelow and in the Figures. The model PSH97, described herein, made distance measurements at the 1 ppm level at distances over 1000 meters, and measurement speed of 1 kHz—although better results were obtained by integrating over around 100 ms, with the most significant improvement for integration over 17 ms (period of 60 Hz noise). In April 2010, Leica introduced the model AT401 laser tracker which has a range of 160 meters. Experimental test results for the AT401 are published in SLAC-PUB-14300, incorporated by reference herein. Where the FARO X adapted absolute distance measurement to a laser tracker architecture, the Leica AT401 adapted the accuracy of a laser tracker to the total station architecture. The distinction between so-called total stations and laser trackers is no longer clear.

The remaining advancement is to extend the range and adapt the instruments for dynamic multilateration, i.e., combine the accurate length measurement and speed of a laser tracker with the range of a total station and use three or more instruments in cooperation and time synchronization to obviate the angle measurement weakness of single instruments.

There has been a long development history of multilateration. Chapter 12 of *The Surveying Handbook*, which is incorporated by reference herein, covers Trilateration. The examples in section 12-14 are somewhat dated by assuming instrument errors of 5 mm+5 ppm for distance measurements, but goes on to speculate what a hypothetical instrument with errors of 5 mm+1 ppm would produce. Of course modern instruments are much better that even the hypothetical specifications of that time. Moreover, the error in angle measurements for conventional triangulation measurements remain the same, i.e., limited by the physics of the atmosphere and optics.

The Greenleaf '625 and Merry '926 patents both used multilateration of laser interferometers in the early 1980s. Pitches et al. disclosed a Three-Dimensional Position Measuring Apparatus in U.S. Pat. No. 4,691,446 Three-dimensional position measuring apparatus in 1987, incorporated by reference herein, which comprises a plurality of laser rangefinders measuring the distances to a plurality of corner cube reflectors. By trilateration, the coordinate of a target point may be determined. However, the '446 patent does not disclose the details of the laser rangefinders or coordinate system and it is not directed to Structural Health Monitoring.

In order to switch between a plurality of points, it is necessary to use an absolute distance measurement, or incorporate a priori knowledge of the approximate distance to a target within the ambiguity of the distance measurement. Payne et al. disclosed such a *Rangefinder with Fast Multiple Range Capability* in Rev. Sci. Instrum. 63(6), June 1992, and U.S. Pat. No. 5,455,670 ('670) Optical Electronic Distance Measuring Apparatus with Movable Mirror in 1995, both of which are incorporated by reference herein. The modulation of 1500 MHz results in an ambiguity of approximately 100 mm. For a quasi static structure, the location of a target will normally be known within an uncertainty of 50 mm, and thus there was no need to provide additional capabilities to resolve the uncertainty.

Note that the 20 custom designed and built instruments, the Model PSH97, did not incorporate tracking capability, since it was designed to switch between a plurality of quasi static targets. Pointing was achieved based on the a priori target coordinate, a finite element model of the structure, and instrument coordinate and orientation with minor adjustments made based on signal strength peaking by searching around the calculated instrument azimuth and elevation encoder readings.

The PSH97 instrument incorporates a six degrees of freedom Kelvin mount, which in combination with laboratory calibration of the instrument and field calibration of the mounting monuments provide for instrument replacement wherein a specific instrument placed on a specific monument can point to a coordinate by dead reckoning by loading a few calibration parameters into the control software.

In order to facilitate strong baseline measurements between instruments, the mirror mounting incorporates a retroreflector on the back side. A measurement between instruments is conducted by a first instrument turning its retroreflector toward a second instrument, and the second instrument measuring the distance to the first instrument. By correcting for the retroreflector offset and mounting, the distance between instruments is measured. The same distance is measured by the first instrument to the second instrument in the same manner. It will be recognized that instruments in a plane cannot determine the z coordinate by measuring between instruments. This is accomplished by a hydrostatic level as described in *Advances in hydrostatic leveling with the NPH6, and suggestions for further enhancements*, Parker, Radcliff, and Shelton, Precision Engineering, 29 (2005) 367-374, incorporated by reference herein.

U.S. Pat. No. 5,764,360 Electro-optical measuring device for absolute distances to Meier in 1998, incorporated by reference herein, discloses Electro-Optical Measuring Device for Absolute Distances which comprises the combination of absolute distance measurement with tracking.

U.S. Pat. No. 7,352,446 Absolute distance meter that measures a moving retroreflector to Bridges and Hoffer in 2008, incorporated by reference herein, discloses combining absolute distance while moving and tracking.

U.S. Pat. No. 7,800,758 Laser-based Coordinate Measuring Device and Laser-based Method for Measuring Coordinates to Bridges et al., incorporated by reference herein, discloses the combination of an absolute distance meter, and interferometer, tracking, and a camera.

Other than the PSH97, there are no other known EDM instruments that incorporate a Kelvin mount or integral retroreflector to facilitate measurements between cooperating instruments. Moreover, the '670 patent teaches the use of plural instruments measuring plural targets—although it has yet to be fully realized for the intended purpose on the Green Bank Telescope, i.e., the '670 patent has not been fully reduced to practice at this time.

A related development to the total station is the laser scanner, which began in the mid 1990s. Laser scanners typically measure distances to surfaces by rapidly scanning a laser beam over the surface, i.e., retroreflectors are not used. The laser beam typically scans by rotating a mirror about two axes, and measuring the angles of the two axes in synchronization with the distance to the surface to produce a point cloud of three-dimensional measurements of the reflected laser beam. Laser scanner architectures tradeoff accuracy for speed and number of points measured.

Measurements of points in the point cloud are typically made based on intervals of the angles or time, i.e., unlike total stations that measure to retroreflector targets and dwell on the measurement for a period of time, laser scanner measurements are made on the fly to nonspecific points on the surface. Example architectures are disclosed in U.S. Pat. No. 6,246,468 Integrated system for quickly and accurately imaging and modeling three-dimensional objects to Dimsdale; U.S. Pat. No. 7,190,465 Laser measurement system to Froehlich et al.; U.S. Pat. No. 6,989,890 Apparatus for taking up an object space to Riegl et al.; and U.S. Pat. No. 7,193,690 Laser scanner and method for optically scanning an environment to Ossig et al., all four of which are incorporated by reference herein.

Laser scanners are particularly useful for large surveys, such as crime scenes, accident reconstruction, construction sites, architectural preservation, as-built facility modifications, and the like. These surveys typically require making scans from multiple locations and later combining the multiple point clouds into a single coordinate system to produce a registered point cloud. Each point cloud is in a local spherical coordinate system of the instrument, i.e., two angles and a radial distance. However, the position and orientation of the center of the instrument is generally unknown.

Registration is the process of determining the six degrees of freedom of each instrument location, i.e., x,y,z, pitch, roll, and yaw. Once these are determined for each measurement location, the point cloud can be transformed as a rigid body translation and rotation into the common coordinate system. It will be recognized that this process does not use trilateration between the various points in the point clouds to combine distances for a common point, but rather combines the points to make a larger number of points in the registered point cloud. In fact, it would be merely coincidental if two measurements corresponded to the same point location on the surface, and highly unlikely if three measurements corresponded to the same point location on the surface.

Moreover, if points in three point clouds did randomly happen to correspond to the same point on the surface, the only way to determine that they corresponded to the same point would be to use the angle measurements and registration process-which is limited by the accuracy of the angle measurements. For example, a scan of the front side of a car may be registered with a scan of the right side of the car to produce a point cloud that includes the front and right side, which may include a higher density of points in the overlapping scans. This process is explained in detail in U.S. Pat. No. 7,180,072 Method and apparatus for creating a registration network of a scene to Persi et al.; and U.S. Pat. No. 7,403,268 Method and apparatus for determining the geometric correspondence between multiple 3D rangefinder data sets to England et al., both of which are incorporated by reference herein.

Large-Scale Metrology

An excellent review of Large Scale Metrology can be found in *Large-Scale Metrology—An Update*, Estler et al., Annals of the CIRP, Vol. 51/2/2002, which is incorporated by reference herein. This series was updated by Peggs, et al., in *Recent developments in large-scale dimensional metrology*, Proceedings of the Institution of Mechanical Engineers, Part B; Journal of Engineering Manufacture 2009, review paper 571, pp. 571-595, incorporated by reference herein. In section 2.4, Estler discusses turbulence, whereby the noise of an angle measurement to a target at a distance L increases roughly as $L^{3/2}$.

Particularly for long outdoor measurements, such as for a civil structure, this is a significant limitation for single tracking instruments, such as the '339, '360, and '446 instruments. This is explained in detail in U.S. Pat. No. 7,101,053 ('053) Multidirectional Retroreflectors to Parker in 2006, which is incorporated by reference herein, at column 3 line 60 through column 4 line 20. In a conservative estimate, the uncertainty of a measurement by trilateration, using three distances, is 25 times less than a standard measurement using a distance and two angles. Note that '053 was reissued with broadening claims as RE41,877, which is incorporated by reference herein.

The '053 patent makes the argument that the best method to achieve strong measurements is by using a plurality of distance measurements and solving for a coordinate by multilateration, i.e., ignore the angle measurements in the adjustment. Moreover, '053 teaches a retroreflector architecture to eliminate the Abbe error for such a measurement.

Historically, there has been a problem measuring to a common virtual point from multiple directions, i.e., the absence of an omnidirectional retroreflector target. One solution for conventional total stations is found in U.S. Pat. No. 6,484,381 System and method for aligning aircraft coordinate systems to Cunningham et al., which is incorporated by reference herein. However, this architecture depends on the measurement of the two angles by the total station-which is a weaker measurement.

U.S. Pat. RE41,877 includes a review of prior art related to the problem of an omnidirectional retroreflector. It also teaches a solution to the problem for many applications. A conventional retroreflector comprises three mutually orthogonal reflecting surfaces intersecting at the apex. The properties of the three mirrors are such that a first beam of light intersecting a first mirror reflects to a second mirror and then a third mirror. After three reflections, the first beam of light reflects from the retroreflector in a second beam of light parallel to the first beam of light. Moreover, the optical path length is the same as the optical path length to the apex-regardless of the offset of the beam to the axis of symmetry. This is what RE41,877 refers to as a "three-mirror" retroreflector, which is how the term is used hereafter herein.

RE41,877 teaches that a mirror that bisects the line between the apex of a retroreflector and a virtual point forms a conjugate pair between the apex and the virtual point. A beam of light that projects along a ray to the virtual point reflects from the mirror to the retroreflector and back to the mirror. The optical path length and the angle of the return ray are virtually the same as though the apex of the retroreflector was at the virtual point. This is what RE41,877 refers to as a "four-mirror" retroreflector, which is how the term is used hereafter herein.

Since the beam of light does not actually go to the virtual point, a second three-mirror retroreflector can be located at the virtual point. One instrument can measure to the virtual point via the four-mirror retroreflector and another instrument can measure to the virtual point via the second three-mirror retroreflector. Of course, they can be aimed in different directions. Various other configurations are disclosed in RE41,877.

Multilateration is well known in the art, and software such as STAR*NET V6 is available from Starplus Software, Oakland, Calif., to perform least squares adjustments.

It will be recognized by those skilled in the art that the speed of light through the atmosphere is dependent on temperature, humidity, and pressure; where temperature is the primary uncertainty. Correction methods are addressed in report GBT Archive L0680 *Methods for Correcting the Group Index of Refraction at the ppm Level for Outdoor Electronic Distance Measurements*, which is incorporated by reference herein. In addition to measuring temperature, humidity, and pressure and calculating the index of refraction, methods are disclosed to use fixed bench marks as refractometers and acoustic thermometry to measure the speed of sound-which is also dependent on temperature. Acoustic thermometry is described in GBT Memo 79 *The Feasibility of Acoustic Thermometry for Laser EDM Temperature Correction*, Parker, D. H., et al. (7-92), which is incorporated by reference herein.

Example Electronic Distance Measurements for Large-Scale Metrology

Example measurements made with the PSH97 instrument described hereinabove will illustrate the utility of EDM for Structural Health Monitoring.

GBT MEMO 160 *Laser Rangefinder Deflection Measurements of the GBT Derrick*, incorporated by reference herein, reports on measurements of the deflection of a derrick crane while lifting a 89 500 pound load from a distance of approximately 725 meters from the instrument. One of the figures is reproduced herein as FIG. 1. Note that prior to the time around 18:50 11 the load was hanging freely near the ground with the boom at approximately 45 degrees to the horizon. Starting around 18:50 12 the boom was raised with pauses to adjust the whip line 13 which slightly adjusted the angle of the load, and thus the center of gravity. When the boom reached approximately 75 degrees 14, the boom was swung right 15, and then the boom was lowered slightly 16.

Note that as the boom was raised 12-14, the derrick moved approximately 45 mm in the direction of the instrument due to the reduction in the moment on the 180 foot tall tower to which the derrick was mounted. Also note that other than the adjustments to the whip line 13, the movement of the tower 12-14 was a smooth function.

GBT Archive L0535, incorporated by reference herein, reports on measurements of a point on the Green Bank Telescope (GBT) which shows measurements from approximately 162 m. A figure is reproduced herein as FIG. 2 from which one will recognize that natural frequency vibrations 21 of approximately 60 microns 22 with a period of approximately 1.5 s 23 are clearly detected.

GBT Archive L0485, incorporated by reference herein, reports on measurements of a point on the GBT from approximately 84 meters. A figure is reproduced herein as FIG. 3 which shows the deflection of the telescope structure near the vertex as a tour group walked approximately 50 m out to the vertex starting 31 around 9:08, and starting to return 32 around 9:18. It will also be recognized that thermal changes 33 are also detectable.

These examples clearly show that EDM is capable of measuring distances, with a group refractive index correction, at around the 1 part per million range for absolute distance, i.e., the range accuracy of laser trackers is practical for much longer ranges than presently commercially available. There are no fundamental limitations preventing total stations from combining the long distance capabilities with the higher accuracy capabilities of the laser tracker. Moreover, dynamic measurements of differential changes in distance operate in the noise level of around 10 microns for outdoor measurements. It will be recognized that signal processing techniques may be used to reduce the noise for repeatable motions such as vibrational analysis, and the noise level will be lower for night measurements.

It will be recognized that even in the absence of atmospheric turbulence, there is a fundamental limitation in angle measurements. A telescope is diffraction limited by the Rayleigh criterion $$\sin(\theta) = 1.220 \frac{\lambda}{D} \quad (3)$$

where θ is the angular resolution, λ is the wavelength of light, and D is the diameter of the telescope aperture. In order to measure angles within 1 part per million-even in a vacuum—the telescope optics would be required to be much larger than conventional total stations. It is clear that in order to obtain 3-D coordinates with the accuracy of EDM, it is necessary to use at least three range measuring instruments and calculate the coordinates by trilateration or using more than 3 instruments using multilateration.

Applications of Electronic Distance Measurement to Civil Structural Health Monitoring Consider a civil structure such as, but not limited to, a bridge or the like. Permanent retroreflectors, or permanent mounts for temporary retroreflectors, can easily and economically be installed at a plurality of locations of interest on the structure. A plurality of fixed bench mark locations fixed in the earth adjacent to the bridge provide a local reference coordinate system which could also be fixed to a global coordinate system, such as the National Geodetic Survey (NGS), by differential GPS observations in conjunction with reference NGS bench mark observations.

For the purpose of this discussion, assume any point on the bridge visible from 3 or more widely spaced locations on the ground can be known, by automated measurements, to an absolute coordinate with an absolute uncertainty of around 100 microns (0.004 inches), and the dynamic location can be known to an uncertainty of around 10 microns at a frequency of several Hertz. It will be understood that the absolute coordinates will be for the entire life of the structure and reference coordinate system.

Application to Recited Civil Structural Cases

Given such a capability, a number of applications will be recognized by those skilled in the art. For example, in the case of the I-35W bridge described hereinabove, a finite element model of the bridge would have predicted the deflections for the previous modifications to the bridge. By knowing the actual coordinates of points before and after the modifications, it would have been noted that the model was in error, i.e., the model of the joints was in error. At the time of the collapse, measurements before the contractor started and as work progressed would have identified that concentrated loading of material on the bridge was a problem.

In the case of the US 51 bridge described hereinabove, movement of the bridge due to migration of the main river channel would have been detected as a long term drift in coordinates of the bridge, changes in the deflections under load due to weakness in the foundations, or asymmetry in the deflections due to differences in the foundation of different columns.

In the case of the I-90 bridge described hereinabove, changes in the coordinates of the bridge or asymmetric deflections over solid vs weak foundations would have identified a problem.

In the case of the I-95E bridge described hereinabove, changes in the coordinates of the bridge would have identified the problem at the outset.

In the case of the US 35 bridge described hereinabove, it is not clear if the corrosion resulted in changes in coordinates of points leading up to the single point catastrophic failure. A nonlinear response could be detected by heavily loading the structure by closing the bridge and placing tanks on the bridge which could be filled with metered water to calculate the dead load while observing the deflections for nonlinearities.

In the Other Civil Structural Failures recited hereinabove, there are insufficient details from news reports to know exactly how the failures occurred. Unfortunately, such failures are so commonplace that extensive investigations and official reports are not published. However, it is likely that some could have been prevented by Structural Health Monitoring, including coordinate measurements.

Other Civil Structural Applications

New bridges and buildings undergo extensive Finite Element Model (FEM) analysis in the design phase. However, a number of assumptions are made-just as the assumption was made that the gusset plates in the I-35W bridge were more than adequate and were not checked by calculation, a modern FEM may approximate the joint as a pin connection and not bother with the details of the gusset. It is common to assume symmetry in a FEM and only model half of a structure with assumptions that the centerline is constrained to only move in a vertical plane. In reality there may be significant asymmetries, such as utility pipes and electrical distribution cables, substations, access ladders and catwalks, access hatches, penetrations, and the like on one side of a bridge or containment building. The mesh size and number of the elements is selected in a trade-off between accuracy and computing time. It is assumed that material properties are homogeneous. All of such factors may be part of the engineering experience.

Finite Element Models can predict deflections and natural frequency modes of a structure in stages as it is being built. By actually measuring the deflections and vibrational modes as the structure is built, errors in the model can be detected when the predicted coordinates do not match the experimental data. Moreover, by providing the designer with feedback, confidence will be gained in the design. It will be understood that movements and deflections are resolved into three axes (x,y,z).

It will be recognized by those skilled in the art-such as experienced engineers—that in the absence of a Finite Element Model, there are general characteristics indicative of a healthy structure. Deviations from these general characteristics will be recognized by those skilled in the art as a harbinger to a structural health problem. For example:

1. Deflections should be linear, i.e., they should follow Hooke's law f=kx where f is force, k is a spring constant, and x is the displacement. For example, the deflection of a bridge deck under a 2 ton load should be twice the deflection under a 1 ton load. The deflections of a tower crane should be linear as the load is translated out the arm.
2. Cracks are one source of nonlinearity that will be identifiable. For example, a crack is stiff in compression and weak in tension. Loading that cycles a cracked element between tension and compression shows strong nonlinearities in the movements of points on the structure. For example, a tower crane with no load typically has a net moment produced by the counterweight. This results in elements of the tower on one side being in tension and elements on the opposite side being in compression. By rotating in azimuth, the loads reverse. A structurally sound tower should produce symmetric deflections as a function of azimuth. However, a cracked weld or member will exhibit different properties for compression and tension.
3. Elements operating near their elastic limit will produce nonlinearities in the movements of points.
4. There should be no hysteresis, e.g., a structure should return to the initial position after a load is removed. By measuring a plurality of points, such things as slipping joints are detectable.
5. Movements should be a smooth function. For example, as the temperature goes through a diurnal cycle, a bridge will expand and contract. Typically one end is supported on a bearing to accommodate these movements. If the bearing is not functioning properly, excessive forces may develop until they reach a point of producing slip. This will be easily detectable by accurate coordinate measurements.
6. Plots of the deflections in (x,y,z) of a cardinal point as a vehicle travels over a bridge at uniform velocity should be capable of being expressed as the first few harmonics in a harmonic series, i.e., there should not be any sharp bumps in the plots, and there should be no hysteresis.
7. Long-term creep should be well understood, such as concrete curing or seasonal moisture absorption.
8. Changes in the damping coefficient, or Q, of the structure should be well understood, such as changes in weight due to rain.

It will also be recognized by those skilled in the art that even in the absence of a Finite Element Model, symmetry of a bridge may be exploited in the analysis. For example, most bridges have left-right symmetry about the direction of traffic and one would expect the deflections of a test load on the left side to produce symmetric deflections for the same load applied to the right side. There can also be symmetry between ends, spans, support columns, and even between other bridges of similar design. Prestress or post-tensioned tendon failure could be detected by asymmetry. Internal corrosion of concrete embedded rebar could be detectable-particularly as a long term drift over years.

It is often the case that the highest loads may be experienced during construction. For example, a load may be cantilevered out producing loading on columns that they will not experience under normal operating conditions. By measuring a plurality of points routinely, problem areas can be detected when experimental data does not match predictions, or something creeps.

As will be recognized by those skilled in the art, the integrity of a bridge may come into question as a result of an accident, flood, earthquake, etc. For example, an accident producing a fire on, or under, a bridge my weaken structural members. Bridges over waterways are often hit by ships, flood debris, ice, etc. Simply by knowing that cardinal points on the bridge are not within the seasonal limits could quickly identify problem areas to an experienced engineer.

Implementation of a Structural Health Monitoring Program for Bridges

Figure 4:
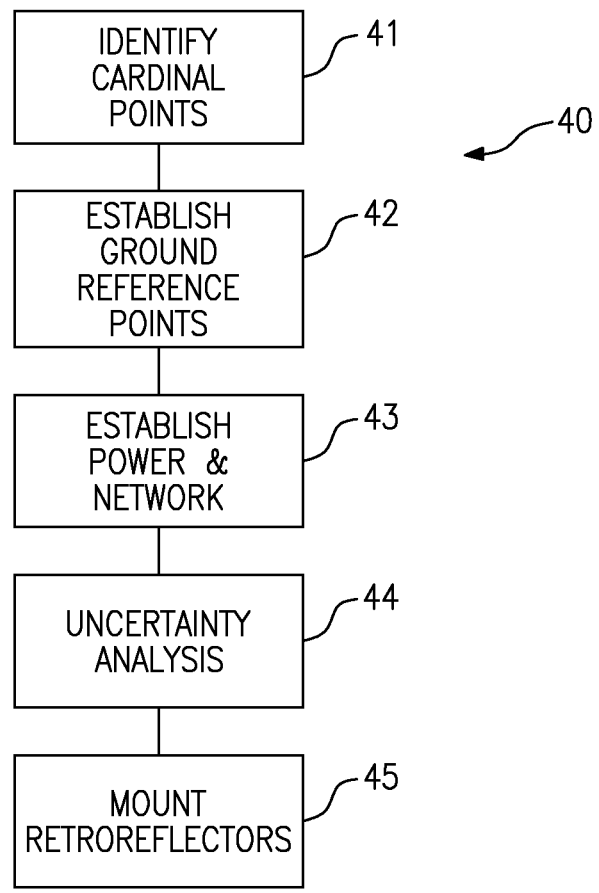
FIG. 4 is a flow chart of the structure preparation for the preferred embodiment.
Figure 5:
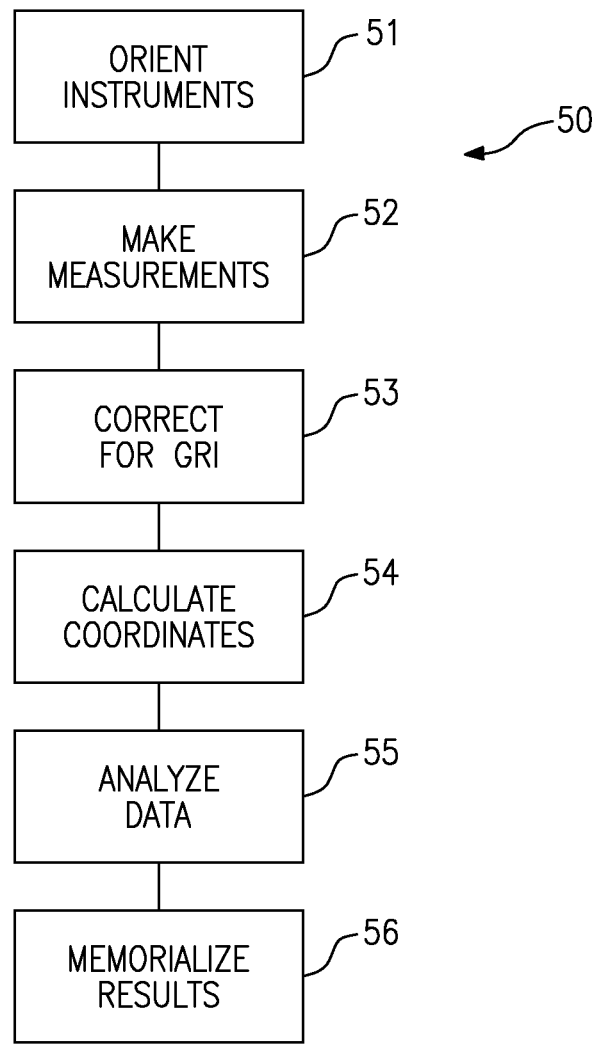
FIG. 5 is a flow chart of the measurement and analysis for the preferred embodiment.

A Structural Health Monitoring Program can be divided into two stages. In the first stage 40, as shown in FIG. 4, the structure is equipped for measurement with permanent fixturing. In the second stage 50, as shown in FIG. 5, the actual measurements are repeated over time, typically using portable instruments.

Stage One

In the US, bridges are typically inspected by State Highway Departments or Railroad owners. Engineers for the responsible agency or owner need to identify cardinal points 41 on the structure that serve as indicators of the health of the structure-including points that should not move in at least one direction. These cardinal points can be added on for existing structures or identified and built into new construction at the design phase.

Stable reference points on the ground need to be established 42 to serve as a reference coordinate system as well as instrument mounting locations. Ideally, electricity and network communications 43 will be available at the instrument locations. In cases of bridges across wide rivers or marshes, it may be necessary to drive pilings to be used as reference points and instrument mountings in order to optimize the geometry of the measurements.

An uncertainty analysis 44 needs to be conducted to determine the optimum geometry for the instrument locations. The software package STAR*NET, described hereinabove, includes a planning utility which generates the error analysis for surveys based on the geometry, instrument accuracies, etc.

Retroreflectors need to be mounted on the structure 45. Due to the relatively low cost and robust design of retroreflectors, they can be left on the structure permanently—although calibration should be taken into account so that the cardinal point can be recovered if the retroreflector require replacement over the life of the structure. Multidirectional retroreflectors, as described in '053 hereinabove, are suggested in order to avoid the Abbe errors.

A conventional survey at the 3 mm uncertainty level is conducted 46 to find the approximate coordinates for instrument pointing.

Stage Two

A means for orienting instruments 51 on a known bench mark is required in order to point the instrument to the approximate coordinates. For example, a Kelvin mount, as used with the PSH97, may be used if the instrument also has a Kelvin mount. More traditionally, instruments measure to reference marks to orient the instruments.

Measurements will be taken to all points and ideally between cooperating instruments 52 to strengthen the baselines. Corrections for temperature, humidity, and pressure, will be made 53 by weather instruments (including possibly acoustic thermometry) or by refractometer measurements based on known baselines. The data will be reduced by multilateration calculations to produce the most accurate coordinate measurements 54.

It will be understood that the measurements can be under static conditions or dynamic load conditions, depending on the nature of the analysis being conducted. While the measurements are preferably performed simultaneously by a plurality of EDM instruments, some meaningful measurements could be made by moving a single instrument to each location. This would probably need to be done in the evening or on overcast days to avoid thermal changes. The data will be analyzed 55 and maintained in the permanent records 56 of the agency or owner for monitoring changes over the life of the structure.

Once the cardinal points and bench marks are established the first time, the process can be repeated by a two person crew in a few hours. For example, a State Highway Department or Railroad can have a traveling crew that could conduct the field survey for several bridges per day. For a more detailed study, or critical structure, the instruments can be operated over a long period of time or be permanent installations.

Example Using a Finite Element Model

Figure 2:
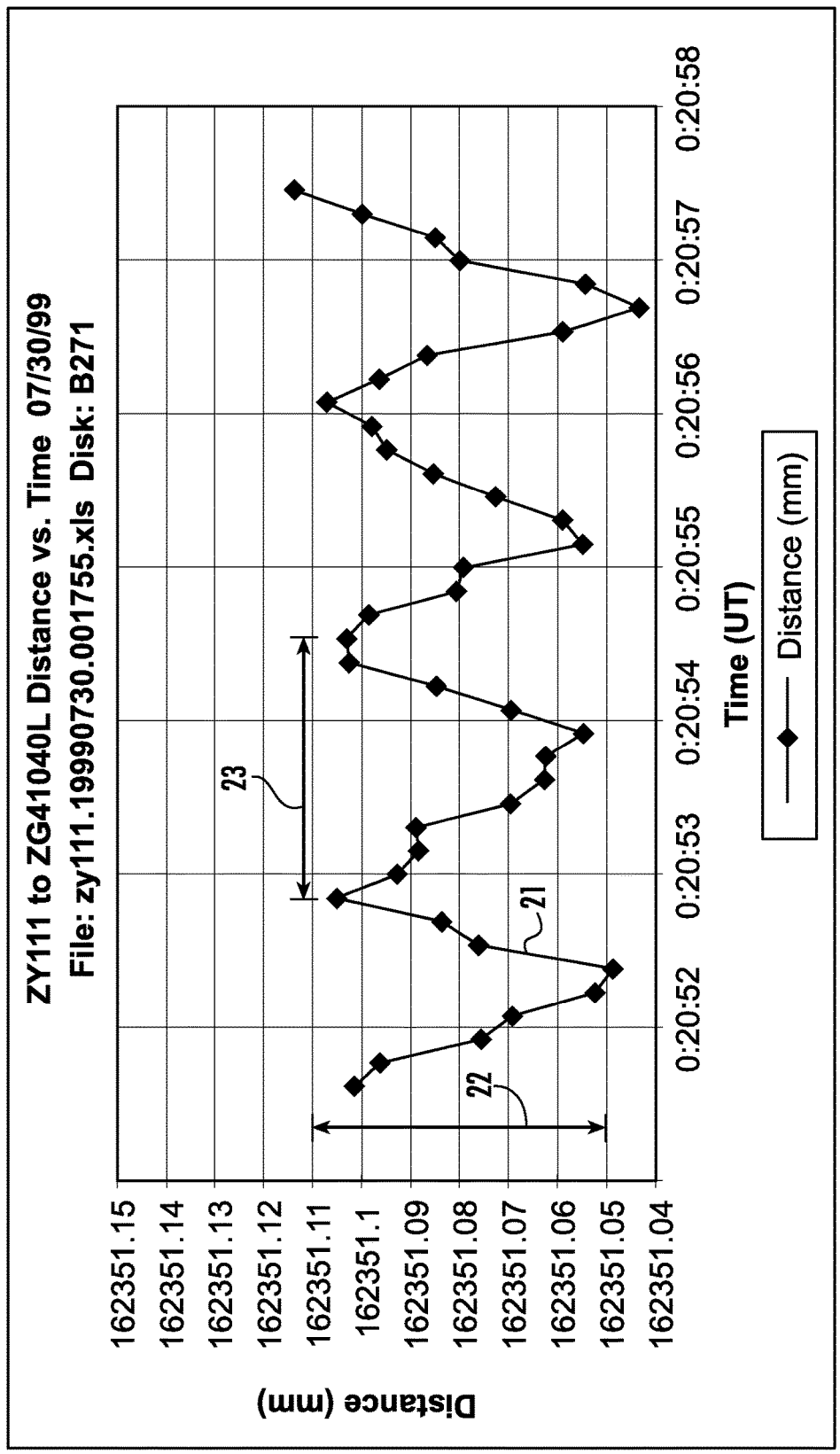
FIG. 2 is a plot of prior art EDM measurements of natural frequency vibrations.
Figure 3:
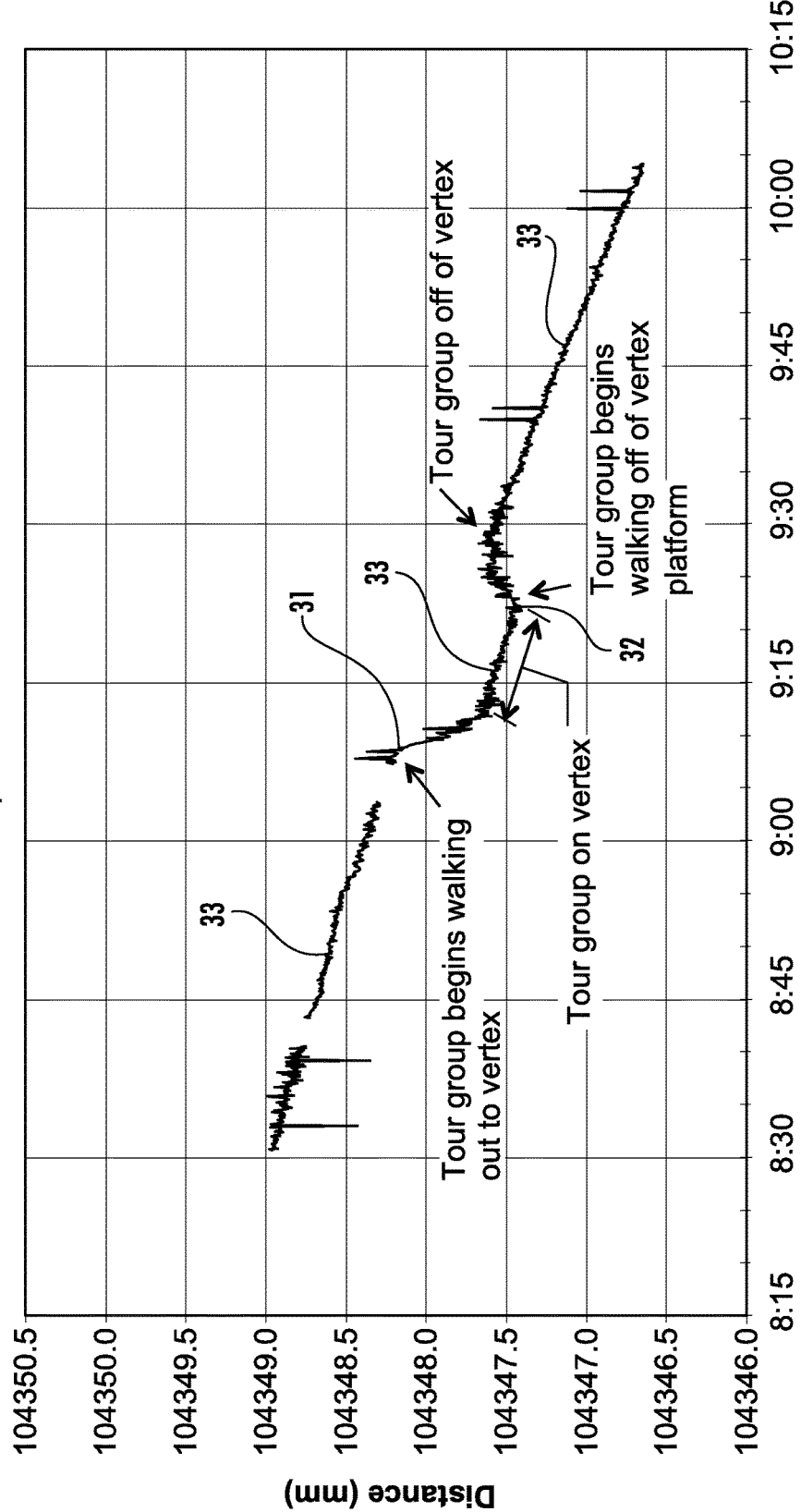
FIG. 3 is a plot of prior art EDM measurements of thermal drift and deflections produced by a tour group walking on a structure.

Most new structures will have a finite element model. As explained hereinabove; the problem is that due to the inherent stiffness, and large size of civil structures, the finite element models are difficult to check experimentally. By using electronic distance measurements from a plurality of locations, extremely accurate measurements can be made to a plurality of points on the civil structure. Moreover, measurements can be made from long distances, as shown in FIGS. 1-3.

Figure 6:
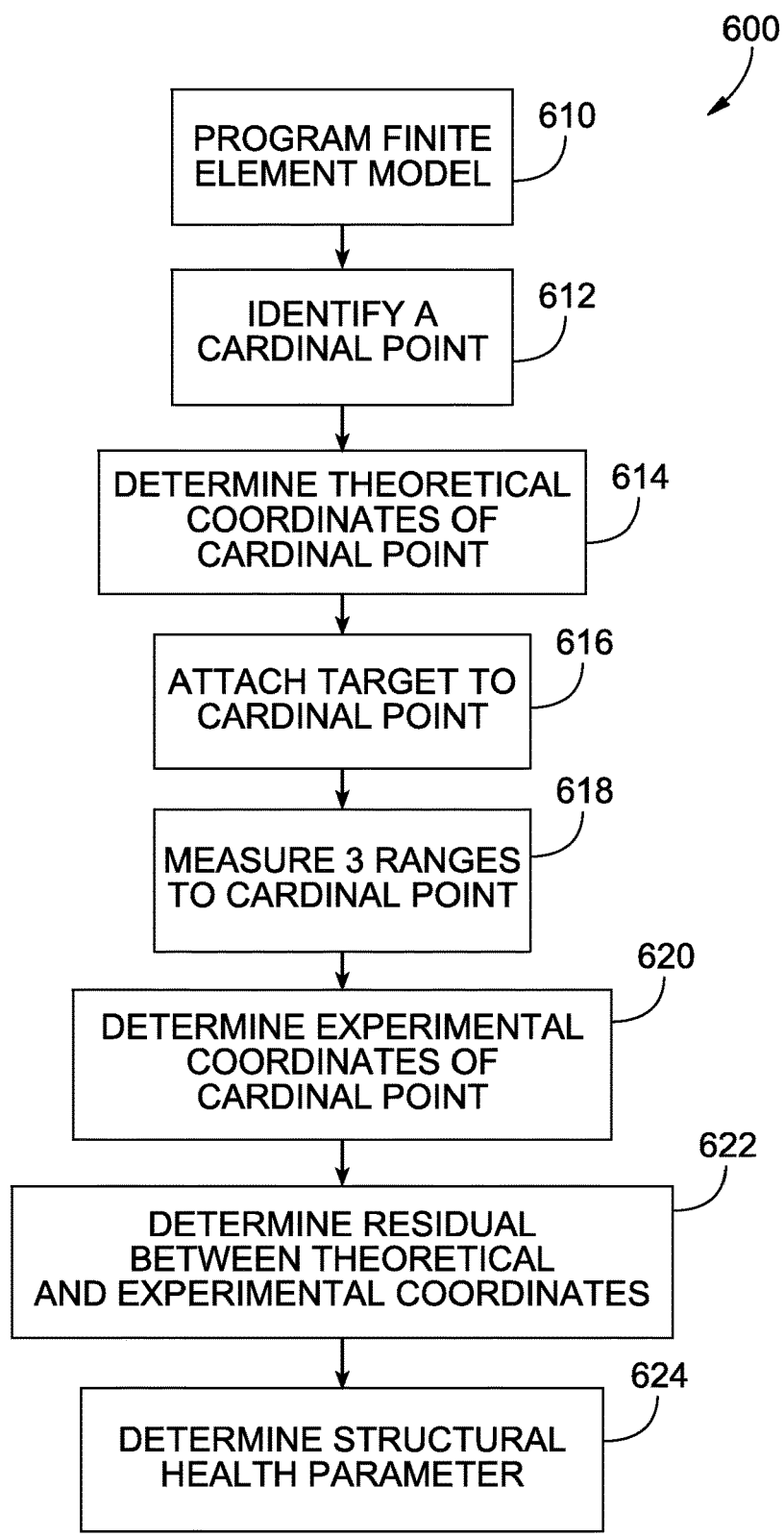
FIG. 6 is a flow chart showing how a finite element model and EDM can be used to determine structural health.

FIG. 6 shows a method 600 using a finite element model in conjunction with experimental EDM measurements to determine structural health parameters. The finite element model is programmed 610 based on materials properties, loading, industry standards, rules of thumb, and other parameters well known in the art. Many assumptions must be made in order to approximate ideal models. For example, a joint may be modeled as a pin free to rotate about an axis, and thus does not exhibit a torque about the axis of the pin-even though the joint may in fact be bolted or welded. Forces may be modeled to intersect at a virtual point. In reality, the actual structure is sure to deviate slightly from the ideal model.

Based on engineering experience, including principles recited hereinabove, and the finite element model, cardinal points can be identified 612 which serve as good indicators of the fidelity of the model to reality. The coordinates of the cardinal points 614 are identified and targets are attached 616. Due to the stiffness of the structure, movements of the cardinal points under various loads may be small, and thus high precision measurements are necessary. For example, the deflection of a bridge under the load of a car may be of the order of a fraction of a mm in the vertical direction. Deflections in directions normal to the vertical may be even less in a healthy structure. However, an asymmetry in the structure may result in slight movements in unexpected directions which would probably go undetected in conventional measurements, such as strain gages or LVDT transducers.

Due to the expense of conventional transducers, it is not common to instrument a structure for unexpected conditions. For example, if a member fails or deforms, the loads will shift to a new equilibrium condition. This may require twisting or shifting of members in directions that they would not normally move. By making strong measurements in all 3 dimensions, such unexpected movements of a fraction of a mm would be easily detected. For example, in the case of the I-35W bridge gusset plate, the forces reached a new equilibrium condition. This probably produced slight movements in unexpected directions which propagated to points that may have been measured by EDM, and thus investigated as to the cause of the unexpected movements.

Range measurements are made from three or more locations to each cardinal point 618, and experimental coordinates are determined 620. The residual, or difference between the theoretical and experimental coordinates, is determined 622.

From the residual 622, structural health parameters may be determined 624. Small residuals will bolster confidence in the finite element model, quality of construction, and serve as evidence that verifiable performance specifications have been met. Unexpected residuals may identify errors in the finite element model, or identify potential problem areas that require further inspection.

It will be recognized that the analysis can be extended to vibration and modal analysis. For example, the stiffness of a structure is directly related to the lowest natural frequency. The stiffer the structure is, the higher the lowest natural frequency. For example, the Green Bank Telescope weighs 16,727,000 lbf and has a lowest natural frequency of around 0.9 Hz. The entire structure is welded steel construction, i.e., there are no bolts or rivets which can slip. As a result, the damping coefficient is very small, or the quality factor Q is very high, where $$Q = 2\pi \frac{\text{energy stored}}{\text{energy dissipated per cycle}}. \quad (4)$$

For this reason, the structure rings for a long time after a disturbance. Any change in the natural frequency or Q of the structure would be a sure sign of a problem. For example, a crack would result in a less stiff structure, which would lower the natural frequency. It would also dissipate energy faster, and thus the Q would go down.

Example Using Characteristic Behavior of a Civil Structure

Most older structures have not been modeled using modern finite element model analysis. However, there are many characteristics that can be developed from first principles and engineering experience—for all civil structures. As explained hereinabove, it is generally understood by experienced engineers that a structure should be linear, move as a smooth function, exhibit symmetric deformations along lines of symmetry and between similar structures, not have cracked members, not operate beyond the elastic limit, not exhibit hysteresis, not exhibit higher order harmonics, not exhibit creep, not exhibit a high damping coefficient, not move after an event, not move over time, not change in dynamic behavior over time, and other characteristics of the like that are well known in the art. Even though an unhealthy structure may not exhibit an anomaly in any of these characteristics, an anomaly can be an indicator that closer inspection is required. In particular, a significant change in any characteristic could be an indicator for immediate inspection. As recognized from engineering experience and lessons taught, problems may be more likely under a combination of circumstances. For example, an oversize load may stress a bridge near the established limit. Extra attention may be called for to ensure everything is still within nominal conditions after the load has passed.

Figure 7:
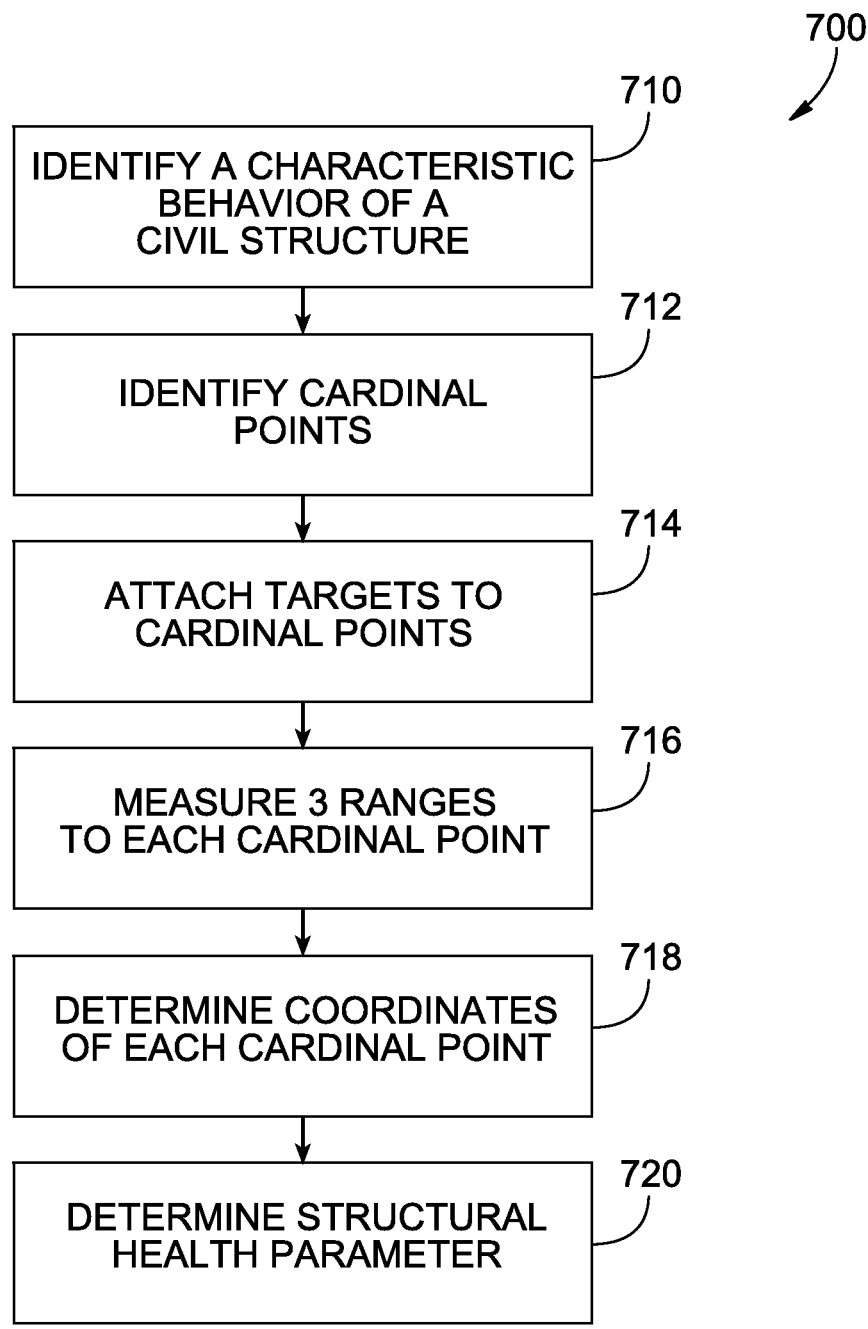
FIG. 7 is a flow chart showing how characteristic behavior and EDM can be used to determine structural behavior.

One method that exploits these characteristics 700 is shown in FIG. 7. Based on engineering experience, a host of characteristics may be identified 710. Depending on the characteristic behavior being investigated, cardinal points can be identified 712 that will serve as good indicators. Targets are attached to the cardinal points 714. Measurements of at least 3 ranges to each cardinal point are made by EDM instruments from stable reference points 716. Coordinates are determined for each cardinal point 718 based on the ranges. Analysis of the coordinates will give strong indicators as to the structural health of the civil structure 720.

Example of a Tower Crane

Figure 8:
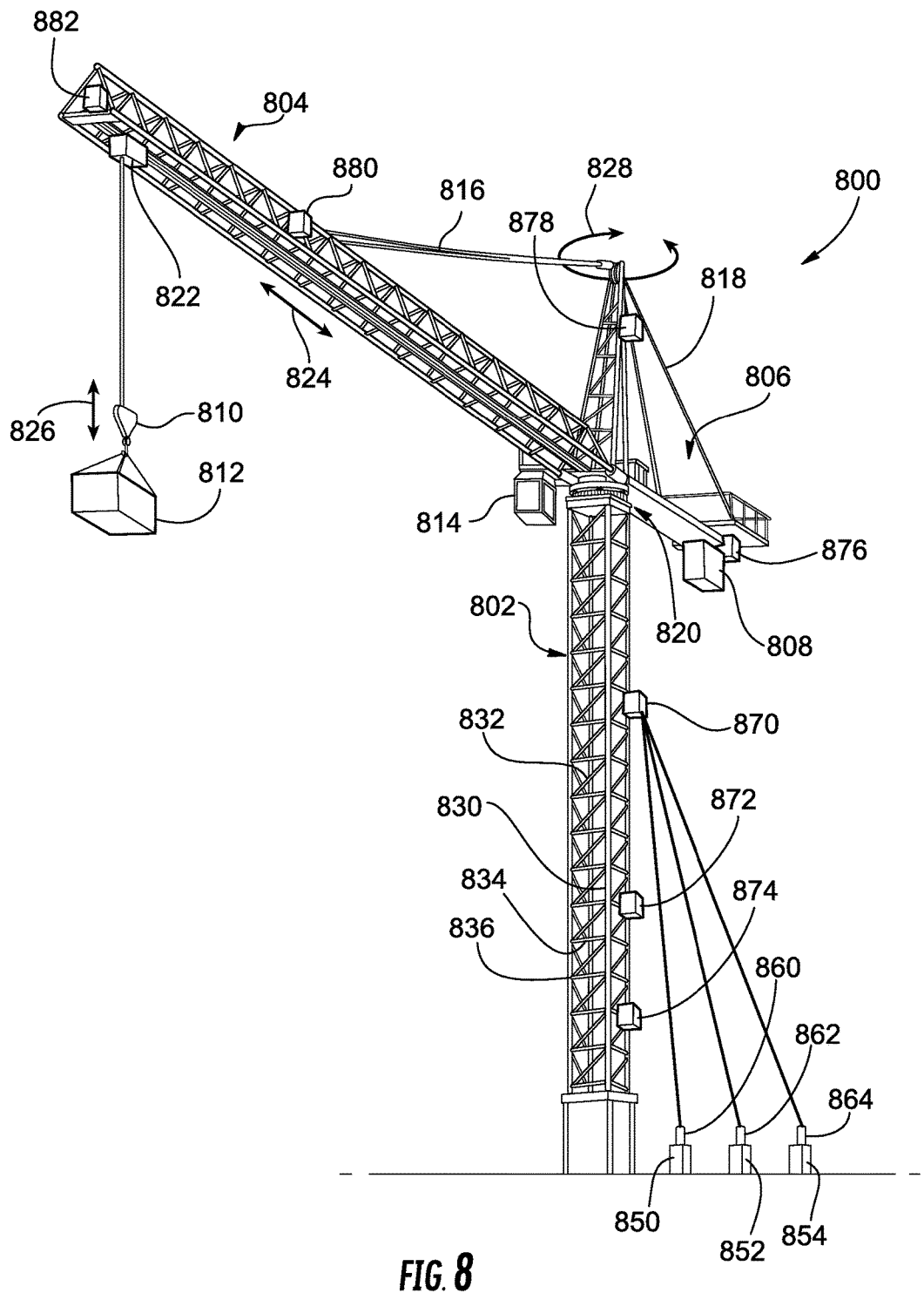
FIG. 8 shows a tower crane being measured.

An example of a tower crane 800, as shown in FIG. 8 will serve to illustrate the method. The tower crane 800 has a rigid tower 802 supporting a load boom 804 and a counterweight boom 806 and counterweight 808. The load boom lifts the load hook 810 and load 812. The operator typically operates the crane 800 from a cab 814 that moves with the load boom 804 for optimal visibility. The load boom 804 is supported by a cable 816 which counters the load 812 by the counterweight 808 and another cable 818. The load boom 804 rotates on the tower 802 via a bearing and drive system 820. The load hook 810 travels along the load boom 804 via a trolley 822 in a radial direction 824, and in the vertical direction 826. By rotating about the tower axis 828, the load 812 can be positioned by the operator. The tower 802 is typically constructed of vertical members 830 with diagonal braces 832 and horizontal braces 834 with welded joints 836. Sections are typically bolted or pinned together in the field.

Electronic distance measurements are made from at least 3 stable instrument locations 850, 852, 854 by EDM instruments 860, 862, 864. Targets are located at a plurality of cardinal points 870, 872, 874, 876, 878, 880, 882. For example, cardinal points 870, 872, 874 on the tower 802 would be good indicators of bending of the tower under load. Ideally, the tower should bend linearly with load 812, and the points on the tower should deflect as a beam fixed at one end, as is well known in the art. For a load balanced by the counterweight, the tower should be straight and in pure compression. Any deviation may be an indication of buckling, which can result in a dramatic failure.

The torque on the tower should be linear with the radial distance of the load 812 from the center of the tower 802. As the boom is rotated about the axis of the tower 828, the moment on the tower will shift directions and vertical members 830 that are in compression will shift to tension, in a sinusoidal function, as the boom 804 is rotated in a complete circle. However, if a joint 836 has a crack, the behavior will not be linear when the load shifts from compression to tension, i.e., the tower will exhibit a non-linear characteristic.

If there is a slippage of the joint, or the crack grows, the tower will exhibit hysteresis, i.e., when the boom 804 returns to the original orientation, the tower will not return to the original coordinates. Using trilateration with three instruments, or multilateration with additional instruments, the coordinates of the cardinal points can be resolved to a fraction of a mm, which will enable engineers to make very good assessments as to the structural health of the tower crane.

As shown in FIG. 8 the top cord of the load boom 804 will be in tension, and the bottom cord will be in compression, due to the cable 816 and tower 802 supporting the load 812. If the trolley 822 is moved inside the cable 816 support point, the loads on the load boom 804 will reverse, i.e., the bottom cord will be in tension. By watching the behavior of targets 882, 880 on the load boom 804, an engineer could make an educated judgment as to the health of the load boom 804.

It will be recognized that based on the teachings of the spirit of the invention, a similar analysis can be conducted for other types of cranes and civil structures.

Crane manufacturers establish safe wind loads. Of course this could depend on many factors which can not be determined in the field. The net result is that the load limits are set very conservatively. This results in a lot of lost time if the guidelines are strictly followed, or possible accidents if judgment calls are incorrect. An architecture as shown in FIG. 8 could be used to set safe operating conditions based on actual deflections in real time. This would result in less lost time, safer lifts, and reduced insurance rates. Factors which could easily offset the expense of the electronic distance measurement instrumentation 860, 862, 864.

In the case of lifts near the manufacturer's limits, or engineered lifts, 29 CFR 1926.550 (a)(1), quoted hereinabove, a qualified engineer is required to document and record the limitations. Needless to say, an engineer would feel much more confident in any recommendations if there were objective measurements upon which to base such recommendations. In the absence of such measurements the engineer is likely to recommend against a questionable lift, which may require bringing in additional equipment or delaying the project. Of course an accident would be even worse. In either case, bringing in EDM instrumentation to make actual measurements would be much more cost effective.

Other Civil Structure Applications

It will be understood by those skilled in the art that the spirit of the methods are not limited to a bridge or crane. For example, after the Sep. 11, 2001 terrorist attack in New York, the structural integrity of buildings in proximity to the World Trade Center were in question. By measuring cardinal points on buildings with respect to a local reference coordinate system before an incident, post incident measurements could assure confidence in the integrity of a building.

Had the World Trade Center Towers been equipped with EDM instrumentation on 9/11, measurements could have provided warning that the building was creeping. For example, the structure should have been rising and tilting to the west due to the morning sun warming the structure, as explained in US 2009/0171619 Surveying procedure and system for a high-rise structure to Van Cranenbroeck, which is incorporated by reference herein. The coefficient of expansion for steel is around 11 parts per million/° C. A point 150 meters (approximately 500 feet) up the structure would rise approximately 1.6 mm/° C. Points above the fire would rise even more. By measuring the differential between the top and mid section of the structure, it would have raised concerns to see the mid section rising, while the top was creeping down instead of up.

Buildings are also susceptible to such things as subsidence due to; foundation faults, water main breaks, tunneling for utilities or commuter rail system construction, earthquakes, hurricanes, or the like. Building integrity can also be called into question by fires, explosions, ramming, renovations, etc.

Indoor sporting arenas, such as the aforementioned Hartford Civic Center and Kemper Arena, have very large open roof structures. Unusual conditions, such as wind or snow loads may put the structure under loads approaching the maximum limit. The invention could be used to monitor conditions of the roof-particularly when it is occupied by thousands of people attending an event.

It would be useful to monitor the health of cranes, or structures in amusement parks, such as roller coasters—in particular when conducting engineered lifts near the design capacity of the crane, or in crowded locations which would endanger life or property in the event of an accident. For example, U.S. Pat. No. 7,681,468 Testing device for tracks of roller coasters to Verl, et al., incorporated by reference herein, discloses a device for testing roller coaster tracks. However it does not measure the structure that supports the tracks-which this invention does.

U.S. Pat. No. 7,580,800 Tools for evaluating and reporting canopy integrity and U.S. Pat. No. 7,819,008 Method of inspecting canopy structures to Winter et al., both incorporated by reference herein, describe inspection of canopy structures-such as canopies at fueling stations. The methods describe the state-of-the-art for inspecting such structures. It will be recognized by those skilled in the art that a much better method would be by making high precision EDM measurements of cardinal points on the structure while subjecting the structure to controlled loading conditions, such as pulling on predefined points on the canopy using a come along, or chain hoist, with a load cell to measure the applied load, and monitoring the movements of the canopy. Alternative methods for loading the structure are disclosed in U.S. Pat. No. 6,757,620 Method for examining structures having high natural vibration frequency using alternating manual vibration-exciting method to Yoon, et al., which is incorporated by reference herein, such as the human vibration-exciting method and the steel-wire cutting method. Hidden interior rust would be evident based on excessive deflections, symmetry, and fidelity to the finite element model for such loading conditions.

Modern civil structures undergo extensive Finite Element Model analysis in the design phase. A number of assumptions must be made in order to simplify the analysis. In the aircraft industry, the models are checked against experimental data to confirm the safety of an aircraft design. In the case of one-of-a kind civil structures, the FEMs are hardly ever checked against the as-built structure. These methods could provide feedback to the FEMs and identify errors in the models.

It will also be recognized that the architecture described could be used indoors, where higher accuracy is desirable, similar to: U.S. Pat. No. 6,484,381 System and method for aligning aircraft coordinate systems to Cuningham et al.; U.S. Pat. No. 7,194,326, Methods and Systems for Large-Scale Airframe Assembly to Cobb et al.; U.S. Pat. No. 7,672,817 Flight in Factory to Marsh et al.; and U.S. Pat. No. 8,688,408 Flight in Factory to Marsh et al.; all four of which are incorporated by reference herein. The architecture could be used outdoors for such large-scale applications as ship building and repair, broadcast towers, dams, etc. It is routine practice to inspect roller coasters daily. However, real-time measurements of roller coaster structures would provide additional assurances and reduce insurance rates.

Pressure Vessel Structural Health Applications

Turning now to applications of EDM instrumentation to measure the safety and performance of pressure vessels, we disclose heretofore unknown methods for measuring and testing large pressure vessels-such as boilers, receivers, nuclear reactor containment structures, storage tanks, tank trucks, railway tank cars, ships, buoyant structures, reservoirs, vacuum chambers, aircraft, spacecraft, and the like.

An extensive search of the prior art, which was summarized in the background hereinabove, failed to find any use of electronic distance measurement instrumentation to make actual measurements of deformations of pressure vessels over time, variable pressure load conditions, or variable mechanical load conditions. Exemplary embodiments will serve to illustrate the methods, in light of which, the spirit of the invention will be recognized by those skilled in the art to be adaptable to solving related measurement and testing problems for other applications.

Containment Building

U.S. Pat. No. 4,080,256 ('256) Nuclear reactor apparatus to Braun et al., incorporated by reference herein, discloses a containment structure for a commercial nuclear power reactor. The right cylindrical, domed roof, concrete structure, disclosed in 1974 is the now iconic structure associated with PWR containment buildings. BWR containment buildings typically employ a smaller containment design with a more conventional outer building. While a PWR design will be used in this example, it will be recognized that similar methods can be applied to a BWR containment structure.

Braun describes the containment building as being about 200 feet in height, and about 140 feet in diameter, with a larger below grade truss section about 180 feet in diameter and about 36 feet in depth. The containment is reinforced concrete with a thickness of around two feet and precompressed by tendons which are tensioned by anchors and tensioning apparatus. As explained hereinabove, in the event of a loss of coolant accident, the containment structure is designed to contain the steam and hydrogen gas up to a design pressure of around 80 psig, i.e., the entire building is designed to perform as a pressure vessel.

As required by 10 CFR Appendix J to Part 50, the containment building must undergo periodic testing to verify the performance and safety of the pressure vessel. The most basic test is to pressurize the containment building, close the pressure source, and watch the pressure for indications of leaks, i.e., if the pressure goes down, they look for the source of the leak. For example, there are pressure lock doors with seals, and many sealed penetrations for pipes and cables through the concrete wall which can fail.

There are no known prescribed test methods which actually measure the deformation of the pressure vessel under the pressure test. For example, under a pressure of 80 psig, a 140 foot diameter dome would experience a vertical force $f_y$ of $$f_y = 80\pi(70 \times 12)^2 \quad (5)$$
$$= 177\,336\,622 \text{ lbf} \quad (6)$$

lifting the dome. This would produce a vertical stress $\sigma_y$ in the 2 foot thick concrete wall of approximately $$\sigma_y = \frac{80\pi(70 \times 12)^2}{\pi 140 \times 12 \times 2 \times 12} \quad (7)$$
$$= 1\,400 \text{ lbf/in}^2 \quad (8)$$

and a hoop stress $\sigma_\theta$ in the 2 foot thick concrete wall of $$\sigma_\theta = \frac{80 \times 70 \times 12}{2 \times 12} \quad (9)$$
$$= 2\,800 \text{ lbf/in}^2 \quad (10)$$

It is well known in the art that concrete has very low tensile strength. The strength to contain the forces for an internally pressurized containment building are due almost entirely to the internal reinforcement bar and tendons. The exact strength depends on the design, but we can get an order of magnitude for the deflections by an estimation.

Young's modulus E is $$E = \frac{\text{stress}}{\text{strain}} \quad (11)$$
$$= \frac{\sigma}{\Delta L/L} \quad (12)$$
$$= \frac{\sigma}{\epsilon} \quad (13)$$

which is around 29 000 000 lbf/in² for steel. If we temporarily assume the containment building is made entirely of steel, which is much stronger in tension that reinforced concrete, we can get a conservative estimate for the minimum deformations. The change $\Delta$ in the length L of the cylindrical structure would be $$\Delta L = \frac{\sigma_y L}{E} \quad (14)$$
$$= \frac{1\,400 \times 236 \times 12}{2.9 \times 10^7} \quad (15)$$
$$= 0.136 \text{ in} \quad (16)$$

or 48 ppm, and the increase in circumference $\Delta C$ would B $$\Delta C = \frac{\sigma_\theta C}{E} \quad (17)$$
$$= \frac{2\,800\pi \times 140 \times 12}{2.9 \times 10^7} \quad (18)$$
$$= 0.509 \text{ in} \quad (19)$$

or a change in the radius of 0.081 in, or about 96 parts per million (ppm).

If we assume reinforced concrete in tension has a more realistic Young's modulus of 10% of that of steel, the deformations would be 10 times those estimated for all steel. Deformation of magnitudes much less than expected are clearly measurable by EDM. For gross deformations, single total stations could be used. If one wanted to conduct tests at reduced pressures, e.g., under safer conditions or more frequently, laser tracker instruments would be required. If one wanted to look at fine detail, such as looking for asymmetries in the response of the pressure vessel due to such things as deteriorated (or improperly placed) reinforcing bars or tendons, cracks, stresses around penetrations or doors; measurement by multilateration would be much more conclusive.

Figure 9:
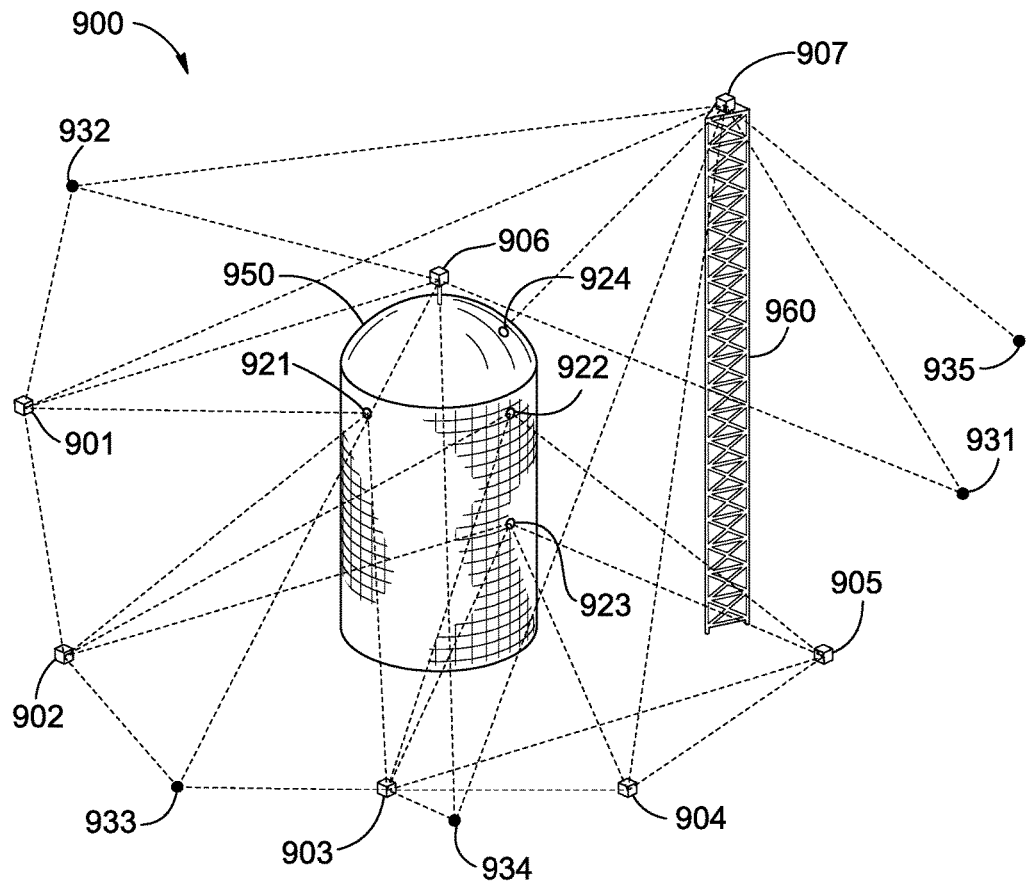
FIG. 9 shows a nuclear power plant containment structure being measured.

One embodiment of a measurement and testing architecture 900 is shown in FIG. 9. Containment building 950 is equipped with retroreflector targets 921, 922, 923, 924 around the cylindrical wall and dome roof.

Preliminary work would be similar to the description for measuring a civil structure in FIG. 4. Multidirectional retroreflectors, as described in US reissued patent RE41877 to Parker, incorporated by reference hereinabove, are ideal for such applications. Multiple instruments can simultaneously measure to a common virtual reflection point using passive retroreflectors.

EDM instruments are attached to stable ground monuments 901, 902, 903, 904, 905. In order to measure to the dome roof, a tower 960 is equipped with an EDM instrument 907. In order to get an accurate location for the tower mounted instrument 907, stable targets are mounted in a fixed geometry on the ground 931, 932, 933, 934, 935. Distances between the tower instrument 907 and the fixed ground targets 907/931, 907/932, 907/934, 907/935 can be used to uniquely determine the coordinates of the instrument.

An EDM instrument can also be mounted on the top of the dome 906 which can measure to fixed ground targets 906/931, 906/932, 906/933, 906/934. Ground instruments 901, 902, 903, 904, 905 can also measure to the ground targets 931, 932, 933, 934, 935. The ground monuments may also be equipped with targets which facilitate measurements between instruments 901, 902, 903, 904, 905, 906. Moreover, the instruments may be equipped with targets which can be turned to cooperate with neighboring instruments to measure between instruments, as described hereinabove for the model PSH97 instruments. The net result is a complex virtual truss architecture of distance measurements which can be used to measure three-dimensional (3-D) coordinates with an accuracy of around 0.100 mm and a resolution of around 0.010 mm.

Measurement procedures and data analysis could be similar to those described in FIGS. 5-7 mutatis mutandis. For example, the location of cardinal points on the containment structure could be measured over the life of the structure. Any changes in the shape or symmetries would be indicators of concern. The structure could be pressure tested at full load and measured to look for changes over the life of the structure. A negative pressure could be applied, which would provide valuable data for hysteresis due to cracks, improperly pre-tensioned tendons, etc. Lower pressure tests could be conducted while the plant is in operation, or on a routine basis.

Ground Transportation

Pressure vessels used to transport materials present additional opportunities for measuring and testing by EDM. In addition to forces exerted by the contents of the vessel, tanks used in transportation are also exposed to forces due to transportation. Increased safety margins are required to protect the public in the event of an accident or leak and to reduce liability for property damages.

For example, as explained in U.S. Pat. No. 4,805,540 ('540) Center stub still railway tank car construction to Mundloch et al., incorporated by reference herein, in railway tank cars, the cylindrical tank is part of the railcar structure. Modern US tank cars no longer have a center sill running between the two couplers to carry the draft load of the train. Instead, a stub sill and coupler is attached to each end of the tank. The tank is attached to the stub sill by a saddle arrangement as described in U.S. Pat. No. 5,351,625 Weld support for railway tank car underbody construction to Culligan et al., U.S. Pat. No. 5,467,719 Method and apparatus for securing a tank to a tank car sill to Dalrymple et al., and U.S. Pat. No. 7,806,058 Tank car stub sill attachment to Saxton et al. for example, all three of which are incorporated by reference herein. Each stub sill is pivotally connected to a truck with 4 wheels and springs to support the respective end and roll on the tracks. The coupler forces are transferred from a first coupler on a first end through a first stub sill to the tank, through the tank, to a second stub sill, and to a second coupler on a second end.

As explained in '540, because the stub sill assembly and the coupler are attached to the lower side of the car, there is a significant moment introduced into the tank structure by the coupler forces. For example, for the first coupler and the second coupler in tension, or when the slack is out, the forces on the tank will be in tension at the lower side of the tank and in compression at the upper side of the tank. The forces will be reversed when the slack is in.

As explained in '540;

Because the center stub sill assembly and the coupler carried thereby were located somewhat below the level of the bottom of the tank (about 8-12 inches below the bottom of the tank), and because the cylindrical tank structure carried the longitudinal train loads axially of the car, an offset moment arm between the tank structure and the centerline of the coupler was present. This offset resulted in a significant overturning moment being induced in the center stub sill and in the end portion of the tank such that the end of the tank and the center sill assembly must withstand these overturning moments. It will be appreciated that the longitudinal train loads that the car is required to withstand, in accordance with the American Association of Railroads (AAR) is a dynamic or impact load of 1,250,000 pounds and a static squeeze of compression load of about 1,000,000 pounds. Because of the vertical offset and the magnitude of the loads, the overturning moments are very significant.

Under normal operation, the saddle is supported on a center plate which acts as a bearing between the saddle and truck bolster. The center plate mates to a bowl shaped portion on the bolster, much like a thrust washer. This results in minimal twisting of the tank, even if the track is uneven, e.g., at an industrial siding that is privately owned and maintained. However, as explained in U.S. Pat. No. 6,357,363 Railroad tank car to Miltaru, incorporated by reference herein, . . . the end portions of the underframe of such a car have to be of relatively heavy construction in order to permit the car when loaded to be supported on jacks located at the corners of the underframe, since there is a relatively long lever arm between the corners of the underframe and the saddle attachment locations, where the weight of the tank and included freight is transferred to the underframe.

As explained in U.S. Pat. No. 5,076,173 Lifting hook arrangement for railway tank car to Baker, et al., incorporated by reference herein, AAR requires provisions for vertical lifting of a tank car by a crane, which can also introduce twisting forces into the tank shell. In some cases, such as cars rated for PIH or TIH lading, the structural requirements may be dictated by the ability to withstand a crash, or puncture resistance. U.S. Pat. No. 7,975,622 System and method for reinforcing railway tank cars to Dalrymple et al., incorporated by reference herein, is an example of such a TIH rated car.

As detailed hereinabove, transportation of hazardous materials is closely regulated by Congress through the DOT. U.S. Pat. No. 6,597,973 ('973) Method and arrangement for inspection and requalification of lined vehicles used for transporting commodities and/or hazardous materials; U.S. Pat. No. 6,832,183 ('183) Method and database arrangement for inspection and requalification of vehicles used for transporting commodities and/or hazardous materials; and U.S. Pat. No. 6,955,100 ('100) Method and arrangement for inspection and requalification of vehicles used for transporting commodities and/or hazardous materials to Barich et al., all three of which are incorporated by reference herein, outline how General Electric Railcar Services Corporation conducts inspections in compliance with 49 CFR non-destructive testing (NDT) regulations. Transportation of corrosive lading requires lining or coating to protect the integrity of the tank as explained in '973. A lining presents additional challenges, since the lining prevents visual inspections of the inside of the tank. Leaks in the lining can allow corrosive material to weaken the tank shell.

Thickness of the tank shell is typically measured by ultrasound measurement, but there are no known measuring and testing methods using large-scale dimensional measurements of tank cars in the prior art.

Figure 10:
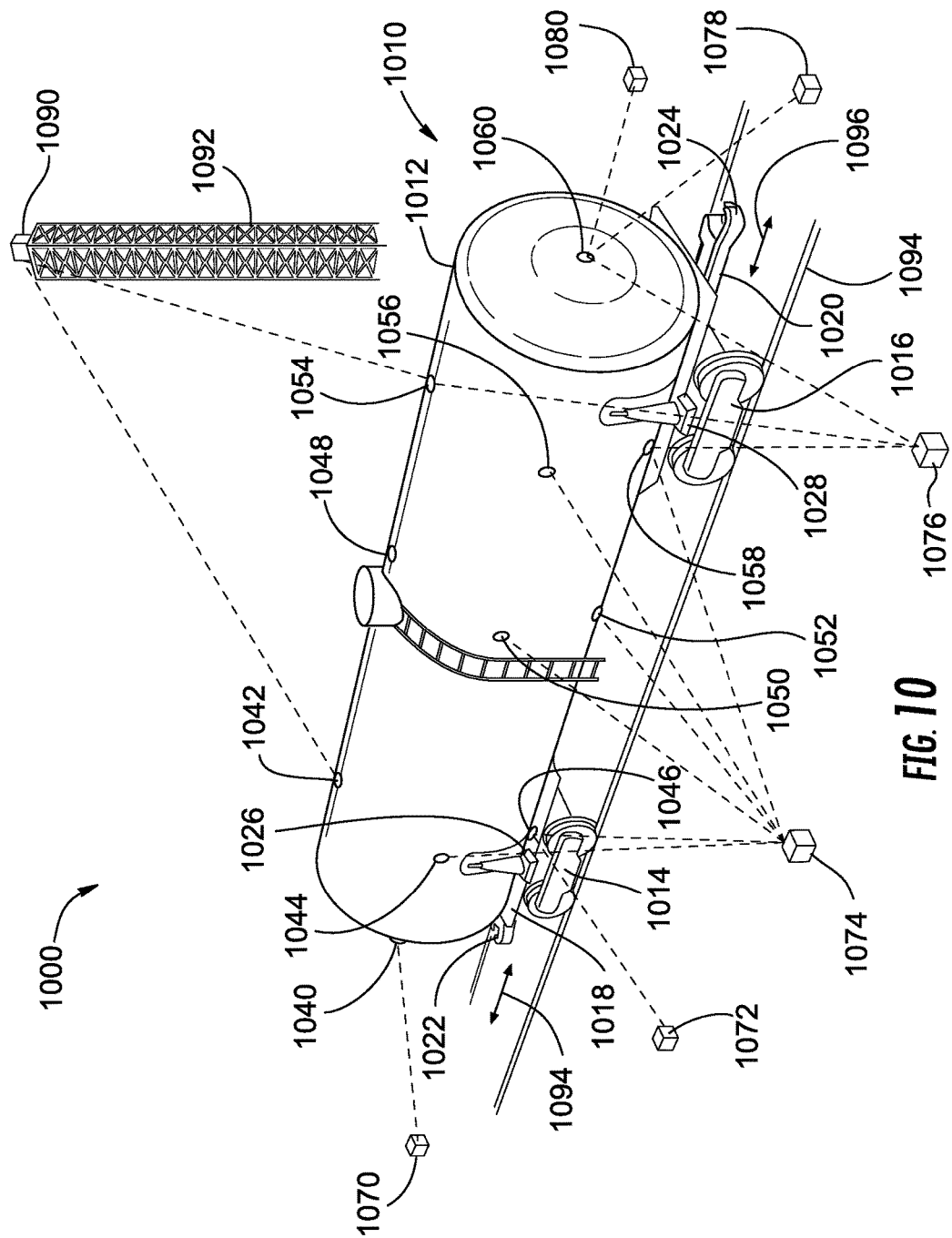
FIG. 10 shows a railway tank car being measured.

Turning now to FIG. 10, one embodiment of an architecture 1000 for measuring and testing a railway tank car 1010 is disclosed. The tank car 1010 includes a tank shell 1012 supported by trucks 1014, 1016 with stub sills 1018, 1020 and couplers 1022, 1024. The stub sills include jacking pads 1026, 1028. The tank shell 1012 is equipped with retroreflector targets 1040, 1042, 1044, 1046, 1048, 1050, 1052, 1054, 1056, 1058, 1060. EDM instruments are located on stable reference points 1070, 1072, 1074, 1076, 1078, 1080. An elevated EDM instrument 1090 is located on tower 1092. In one embodiment, additional EDM instruments may be located in a pit (not shown) below the track 1094 in order to measure additional points under the tank shell 1012 from below.

In one method, the EDM instruments measure all of the targets visible to each instrument. The EDM instruments also measure between stable reference points. The 3-D coordinates are determined for each target under a first condition. For example, the first condition may be unloaded.

The first condition is modified to a second condition. For example, the second condition may be a change in internal pressure of the tank; lifting a corner of the car at a jacking pad 1026, 1028; or exerting a tension or compression force 1094, 1096 on the couplers 1022, 1024. By repeating the EDM measurements and determining the changes in the 3-D coordinates, the deformations for the prescribed load conditions can be determined. The load conditions can then be modified again and the measurement process repeated. It will be recognized that parameters such as linearity and hysteresis can be determined from such measurements. In particular, due to the fusion welded design of tank cars, there should be little or no hysteresis and non-linearity. By applying a slight vacuum inside the tank, any cracks would be put into compression instead of tension. This would result in a deviation from a linear response, i.e., the tank would be slightly stronger under a vacuum load. The degree of the deviation could provide a good indication of fracture cracking.

The measuring and testing can be repeated on a periodic basis, e.g., annually, every 5 years, etc. It will be recognized that such a method can be implemented in a semi-automated program. The only manual operation would be to re-attach the retroreflector targets to benchmark pads welded to the tank shell and apply the load conditions. For example, to test the 280,000 tank cars in the fleet every 5 years, 1076 cars would have to be tested per week. Assuming five day operation of three shifts, this would require testing around 9 cars per hour. This would probably require 9 inspection stations across the US.

Exerting the tension or compression force 1094, 1096 on the couplers 1022, 1024 can be by a hydraulic jack and anchor fixtures designed to exert 1 250 000 lbf in the horizontal direction. This may require a heavy grade beam between the ends of the car to anchor the fixturing against the large forces and moments produced by the jack and anchor. Due to the sensitivity of the EDM measurements, the pressure and coupler load testing may be conducted at reduced pressures and forces for some tests-which would make the tests safer to conduct and less expensive fixturing could be used.

For some investigations, the tank may be dynamically tested by exciting the tank cavity into resonant vibrational modes. This is relatively easily achieved by driving the tank cavity with pulses of air, or other methods well known in the art. By measuring such things as the resonant frequencies and the Q of the tank, the presence of cracks could be ruled out. The amplitude of the low frequency resonant mode vibrations are easily measured by EDM.

While using tank cars to illustrate the methods, the same principles can be applied to motor carriers. Again, measurement procedures and data analysis could be similar to those described in FIGS. 5-7 mutatis mutandis.

Aircraft

It will now be recognized that the methods described for civil structures, containment structures, and railway tank cars can be adapted in the same spirit for aircraft. For example, in the cited cases of the Aloha Airlines flight 243 and Southwest Airlines flight 812, measurements of three-dimensional coordinates of cardinal points of the fuselage at the 1 part per million accuracy would likely detect anomalies in the linearity and hysteresis of the aircraft undergoing pressurizations. In particular, defects such as elongated holes would be particularly evident by positively pressurizing the cabin while measuring the deformations, returning the cabin to ambient pressure, and then negatively pressurizing the cabin. When the forces are reversed between positive and negative cabin pressure, the joints will slip nonlinearly and the condition at ambient will depend on the path from positive pressure to ambient or negative pressure to ambient, i.e., there will be a difference in the shape of the fuselage depending on the previous state. Moreover, the cracks will be subject to asymmetric strength depending on the direction of the forces-which of course should not be the case for a healthy structure.

Reservoirs

Reservoirs can be classified as both a civil structure and a pressure vessel. Pumped-storage reservoirs for electrical power generation are a particularly interesting application. There are 19 such reservoirs in the US operated by 19 different companies:

1. Bad Creek, S.C.—Duke Power
2. Bath County, Va.—Dominion Virginia Power
3. Blenheim-Gilboa, N.Y.—New York Power Authority
4. Cabin Creek, Colo.—Xcel Energy
5. Castaic, Calif.—Los Angeles Department of Water & Power
6. Gianelli, Calif.—California Department of Water Resources
7. Helms, Calif.—Pacific Gas and Electric
8. Jocassee, S.C.—Duke Energy Carolinas
9. Ludington, Mich.—CMS Energy
10. Mount Elbert, Colo.—US Bureau of Reclamation
11. Muddy Run, Pa.—Excelon Power
12. Northfield Mountain, Mass.—FirstLight Power Resources
13. Olivenhain-Hodges, Calif.—San Diego County Water Authority
14. Racoon Mountain, Tenn.—Tennessee Valley Authority
15. Rocky Mountain, Ga.—Oglethorpe Power
16. Salina, Okla.—Grand River Dam Authority
17. Seneca, Pa.—FirstEnergy
18. Smith Mountain, Va.—Appalachian Power
19. Taum Sauk, Mo.—Ameren Missouri On Dec. 14, 2005 the Taum Sauk, Mo. reservoir suffered a breach in the dike, which catastrophically emptied the reservoir causing injuries and significant property damages. While the root cause of the accident was an equipment and operator failure which resulted in overfilling the reservoir, the structural failure illustrates the potential for injuries and property damages from a structural failure.

It is well known in the art that fatigue is often correlated with the number of stress cycles an element undergoes. In the case of pumped-storage dams and reservoirs, the ideal condition is for the reservoir to be completely filled each evening during minimal power demand and emptied each day during peak power demand. Unlike conventional dams, this results in the load on the dam being cycled every day.

In one embodiment, EDM instruments could be used to measure the deformations of such a structure and watch for long term movements and changes in the performance of the structure.

Prestressed Concrete Tensioning Structural Health Applications

Turning now to applications of EDM instrumentation to measure the safety and performance of prestressed concrete, we disclose heretofore unknown methods for measuring and testing prestressed concrete undergoing tensioning changes-such as slabs, columns, girders, bridges, towers, elevated storage tanks, silos, cooling towers, wind power generation towers, liquefied gas storage tanks, nuclear power containment buildings, and the like.

An extensive search of the prior art, which was summarized in the background hereinabove, failed to find any use of electronic distance measurement instrumentation to make actual measurements of deformations of prestressed concrete undergoing tensioning or detensioning. Exemplary embodiments of post-tensioning operations will serve to illustrate the methods, in light of which, the spirit of the invention will be recognized by those skilled in the art to be adaptable to solving related measurement and testing problems for other applications, including during the release of jacks following curing of pre-tensioned concrete.

Figure 11:
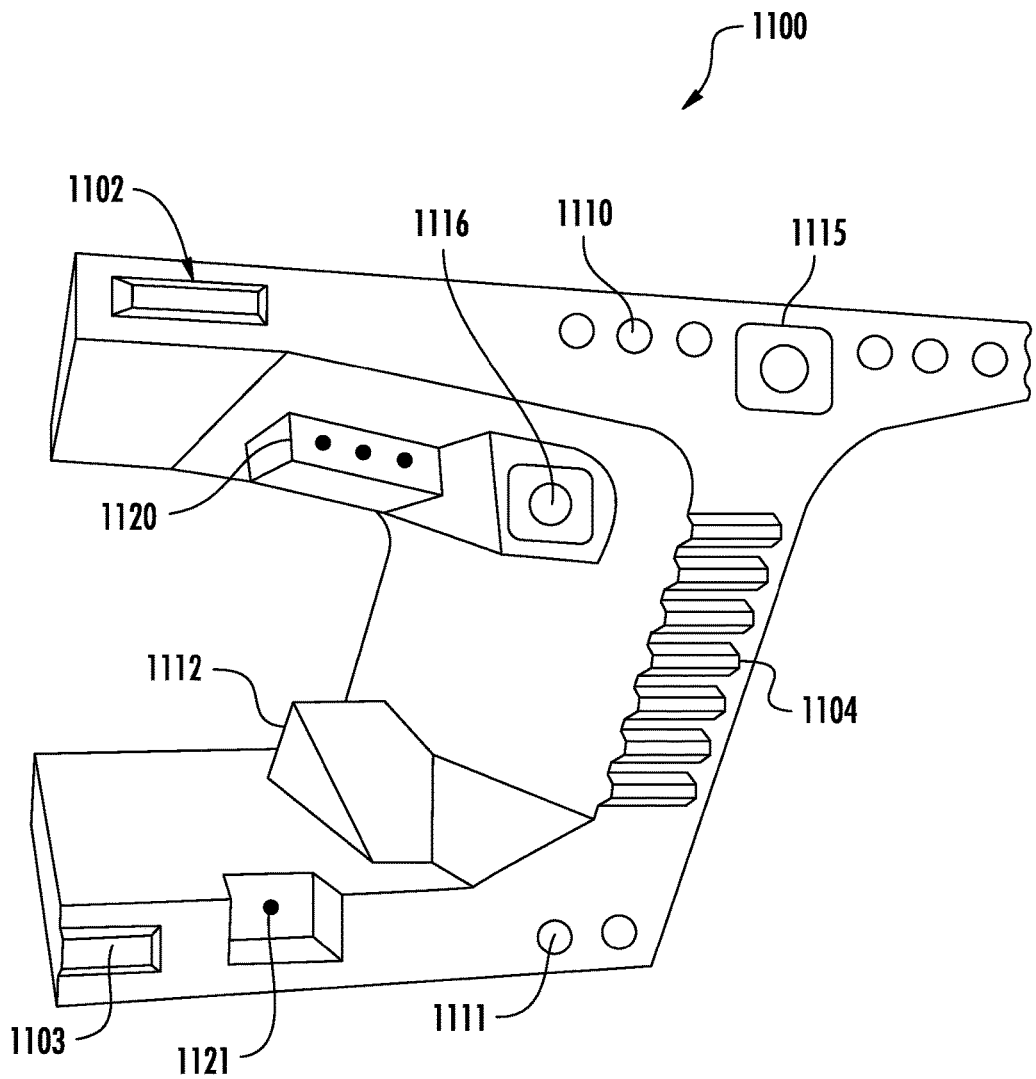
FIG. 11 shows a section of a box girder bridge segment.

FIG. 11 is a section of a box girder bridge segment 1100, as shown on page 23 of *New Directions for Florida Post-Tensioned Bridges*, which was incorporated by reference hereinabove, and includes many other post-tensioning examples. The segment 1100 is precast and delivered to the bridge site for erection. The segments are interlocked by keys in the deck at the top 1102, at the bottom 1103, and in the web on the side 1104. Conduits at the top 1110 and bottom 1111 provide clearance for continuity tendons that run through the section. Continuity tendons may anchor to blister blocks 1112. Some conduits provide clearance for cantilever tendons that are anchored on the segment face 1115 at one end and at blisters 1116 on the other end. Additional anchors may be provided in the top 1120 and bottom 1121 for temporary tendons used for erection.

FIG. 12A shows an erected box girder bridge 1200, and FIG. 12B shows a detail 1250 of the top and bottom tendons anchored to blisters 1116, 1112, as shown on page 26 of *New Directions for Florida Post-Tensioned Bridges*. In some embodiments, the segments 1100 are assembled from piers on the left 1210 and right 1211. Segments from the left 1260 are cantilevered out from the left pier 1210, and sections from the right 1270 are cantilevered out from the right pier 1211. They meet at a closure joint 1251 that is poured to join the two sides 1260, 1270 together.

Figure 13:
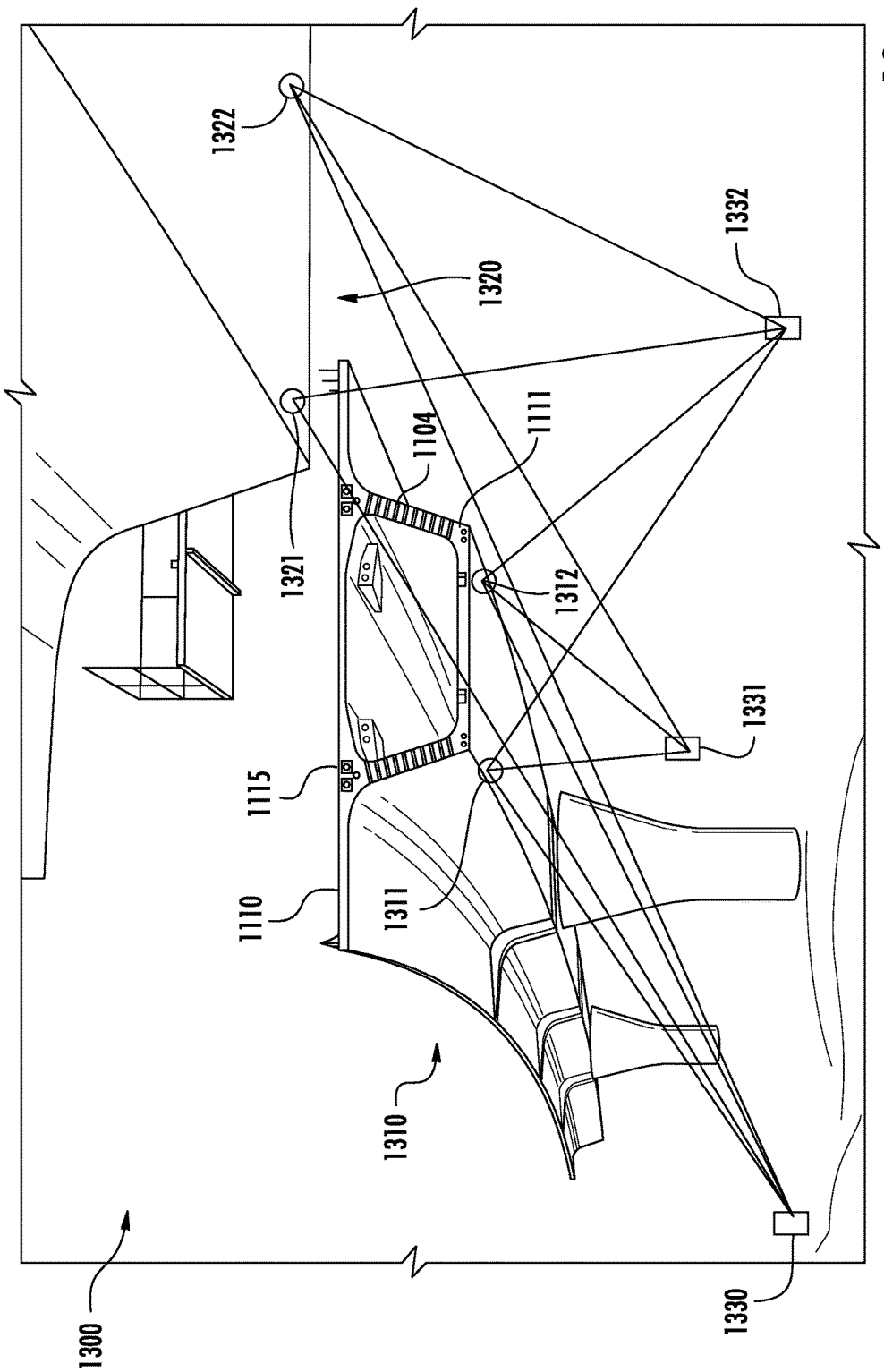
FIG. 13 shows a bridge under construction and a measurement system.

FIG. 13 shows an embodiment of a bridge 1300 under construction with a left segment 1310 and a right segment 1320 to be joined. At this stage of construction, the left segment 1310 is cantilevered from the pier. Temporary tendons anchored on the top segment face 1115 counteract the moment of the segment 1310. Tension at the top compresses the concrete in the top of the segment and the moment compresses the concrete in the bottom of the segment. When the left segment 1310 is joined with the right segment 1320, deflection of the bridge by a live load will put the bottom in tension and the top in compression, i.e., the load distribution changes after the closure joint 1251 is poured and construction is completed. This is counteracted by the tendons in the bottom 1111, which put the concrete in the bottom under compression.

To monitor how the changes in load and tendon tensions affect the bridge, retroreflector targets 1311, 1312 are attached to cardinal points on the left segment 1310 and retroreflector targets 1321, 1322 are attached to cardinal points on the right segment 1320. EDM instruments 1330, 1331, 1332 are attached to stable ground monuments with a plurality of unobstructed paths between the retroreflector targets 1311, 1312, 1321, 1322 and the EDM instruments 1330, 1331, 1332. The number of retroreflector targets and EDM instruments are merely to illustrate the measurement principles. In practice, many additional retroreflector targets and EDM instruments may be used.

By measuring the distances to each retroreflector target 1311, 1312, 1321, 1322 from at least three locations 1330, 1331, 1332, the three-dimensional coordinates of the cardinal points can be measured with very high accuracy, e.g., of the order of one part per million. Measurement procedures and data analysis could be similar to those described in FIGS. 5-7 mutatis mutandis.

Recall that the coefficient of thermal expansion of concrete is around 8 to 12 parts per million per ° C., or 8 to 12 microstrains per ° C. It should also be noted that for concrete with a modulus of elasticity E of $3 \times 10^6$ psi, a change of strain $\epsilon$ of one microstrain corresponds to a change in stress $\sigma$ of 3 psi.

While strain gages and extensometers have the sensitivity to measure changes in strain in the order of microstrains, they typically only measure differential movement between two relatively close locations bonded to the structure, and they only measure one degree of freedom, i.e., along a single axis. In contrast, this invention measures three-dimensional coordinates, in an absolute coordinate system, over hundreds of meters-without contact by the measurement instruments.

The selection of the cardinal points to be measured is based on engineering experience, a finite element models of the structure, a plan for tensioning the tendons, and possibly other factors. Engineering experience includes principles described hereinabove, e.g., Hooke's law, crack behavior, elastic limits, hysteresis, smooth functions, harmonic analysis, creep, damping coefficient, and other accepted engineering principles. Engineering experience also includes many factors that may be unique to a particular project, including such things as: industry and government standards, regulatory requirements, lessons learned from previous projects in the industry, contractor performance history, level of confidence in quality control, level of confidence in the finite element model, complexity and uniqueness of the design, confidence in assumptions made, test results, consequences of a failure, litigation potential, establishment of liability, safety concerns for the workers and final users, schedule, cost, weather conditions, preservation of personal and company reputation, demonstration of understanding to convince others, prototype evaluation, etc. For example, if concrete test results are marginal or in question, additional measurements of the completed structure may be needed to ensure confidence in the as-built structure. If technical credibility with the public or a regulatory agency is in question, additional measurements may be in order to assure confidence and expedite acceptance or negate the need for additional testing.

Note that the bridge 1300 is curved-much like the Las Lomas Bridge and the Kapiolani Interchange On-Ramp Project that experienced pullout of horizontally curved tendons, and cracks and spalling, as described hereinabove in the BACKGROUND. As an example, retroreflector targets 1311, 1312, 1321 are near the lower continuity tendons 1111 and retroreflector target 1322 is near the center.

By measuring the three-dimensional coordinates of the cardinal points as the tendons are tensioned, or detensioned, the movements could be compared to predictions from the finite element model and the tensioning plan. Deviations from the model would be detected before failures occurred, i.e., before hearing a loud bang. Note that if the tensioning plan calls for asymmetrically tensioning tendons, or the segments are not uniformly made, the end of the segment 1310 will not only compress along the longitudinal axis of the tendons, but will also deflect in the transverse and vertical directions. Moreover, it will possibly twist and distort the segment 1310. The combination of retroreflector targets 1311 and 1312 will clearly show changes in five degrees of freedom, i.e., three degrees of motion and rotations about the longitudinal axis and the vertical axis. With a third non-coaxial retroreflector target, all six degrees of freedom can be measured.

Had such a system been in place during tension of the Las Lomas Bridge and the Kapiolani Interchange On-Ramp Project, and the engineers were aware of the heretofore unavailable measurement accuracies of the system, anomalies would have probably been detected well before tendon failures were experienced. For example, larger than expected deflection would have been measured in the transverse direction along the radius of curvature due to the radial forced developed by the bottom continuity tendons 1111. When bottom continuity tendons 1111 started crushing the conduits, nonlinearities would have been measured in the deflection vs tendon load. Horizontal forces causing movement of the structure on the piers would have been measured.

Glišić, et al., described the distortion of box girders in, *Structural Health Monitoring Method for Curved Concrete Bridge Box Girders*, which is incorporated by reference herein. They describe measurements of the distortion using 1 meter long deformation sensors, or extensometers. Each deformation sensor only measures one degree of freedom along the 1 m axis. To measure shear, instruments are used in pairs. They augmented the measurements with tilt meters and thermocouples.

On such curved bridges, engineers may have concerns about the horizontal forces that would tend to distort the trapezoid shape of the segments 1310, 1320. Some segments may include diaphragms transverse to the tendons to prevent distortion. The engineers may want to put additional retroreflector targets above retroreflector targets 1311, 1312, 1321 near the stiff upper deck that would resist the horizontal bending more than the narrower bottom of the segments 1310, 1320, where the bottom continuity tendons 1111 develop large radial forces. By measuring the relative movement between the top and bottom of the web, distortion of the trapezoid could easily be measured in three dimensions—with an accuracy in the order of microstrains—and compared to the finite element model predictions. Significant deviations between the predicted and measured deflections would alert the engineers to halt the tensioning operation for further analysis.

Figure 14:
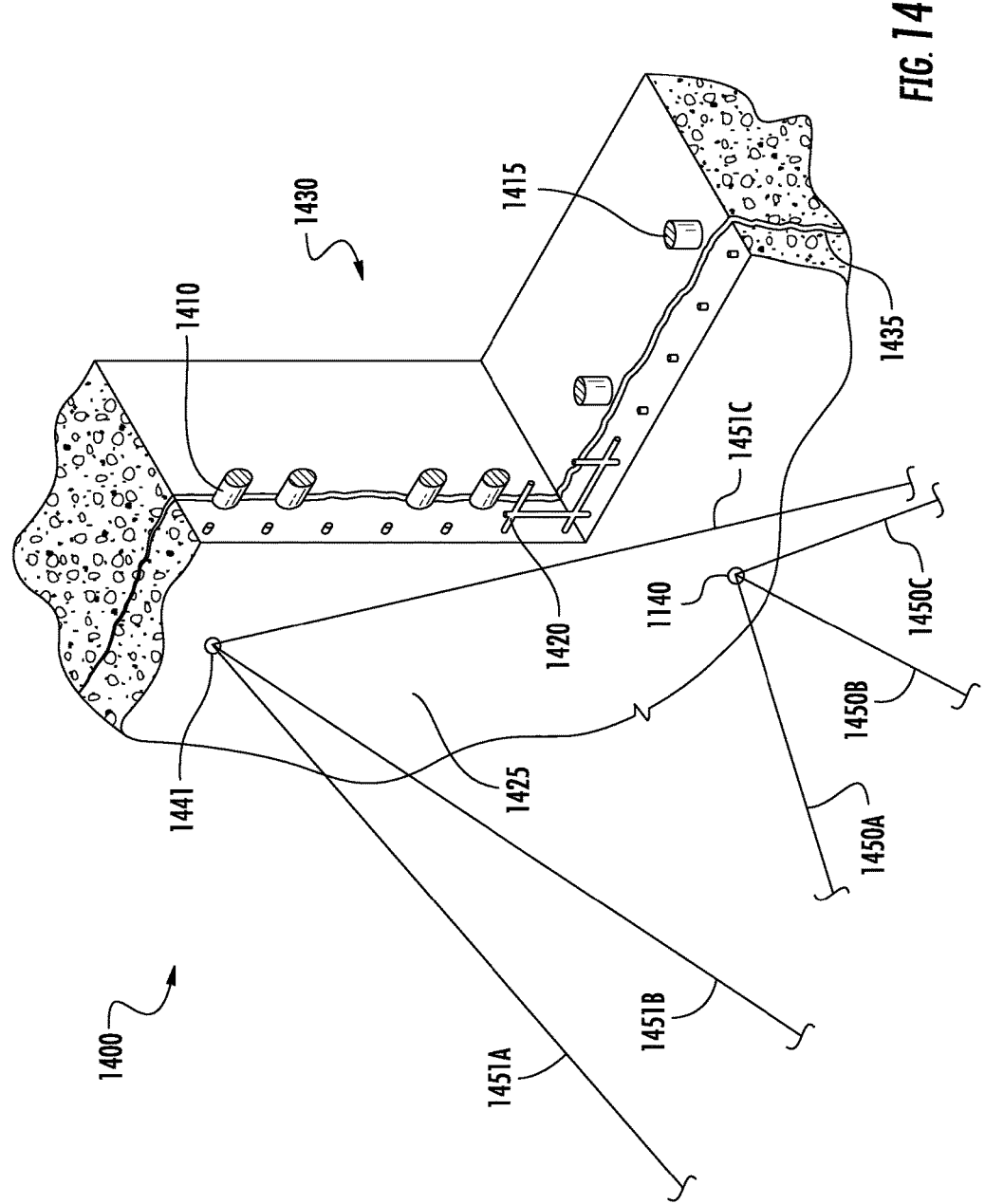
FIG. 14 shows a section of concrete from the Crystal River Nuclear Power Plant containment building, including a measurement system.

FIG. 14 shows a section of concrete 1400 from the Crystal River Unit 3 Nuclear Power Plant containment building that delaminated, as described hereinabove in the BACKGROUND and shown on page 15 of the Progress Energy presentation incorporated by reference hereinabove. Horizontal tendons 1410, vertical tendons 1415 and rebar 1420 are located near the outer wall 1425. The concrete is 42 inches between the outer wall 1425 and the inner wall 1430. When the tendons 1410, 1415 were detensioned, a crack 1435 developed along the plane of the tendons 1410, 1415.

Figure 15A:
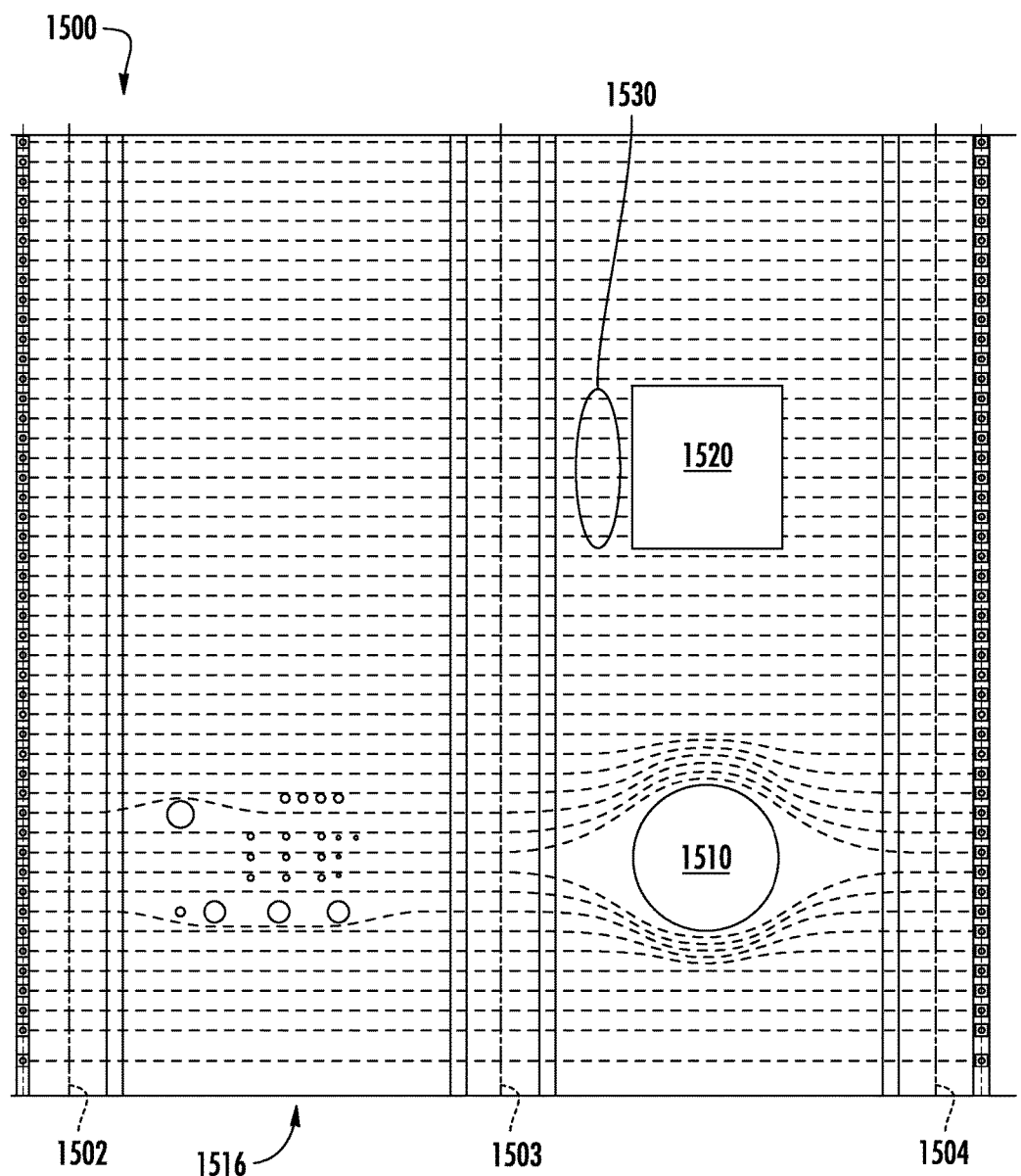
FIG. 15A shows a first set of horizontal tendons in a nuclear power plant containment building.

As described hereinabove in the BACKGROUND, a first set of horizontal tendons extend from a second buttress, through a third buttress, and terminates on a fourth buttress. A second set of tendons extends from the third buttress, through the fourth buttress, and terminates on a fifth buttress. As described in the BACKGROUND the first set are identified by a prefix of 42H, and the second set is identified by a prefix of 53H. As shown on page 35 of the Progress Energy presentation, FIG. 15A shows the first set of horizontal tendons 1500 anchored at buttress number 2 1502 and buttress number 4 1504. As shown on page 36 of the Progress Energy presentation, FIG. 15B shows the second set of horizontal tendons 1501 anchored at buttress number 3 1503 and buttress number 5 1505.

The containment building has an equipment hatch 1510 in bay 34 and various pipe and conduit penetrations 1515, 1516 in bay 23 and bay 45. In order to cut a temporary construction opening 1520 in bay 34 of the containment wall 1400 for replacement of the steam generator, 8 tendons 42H27 through 42H34 1530 and 9 tendons 53H27 through 53H35 1531 were detensioned at the elevation of the temporary construction opening 1520. The corresponding vertical tendons passing through the temporary construction opening 1520 were also detensioned.

Figure 15B:
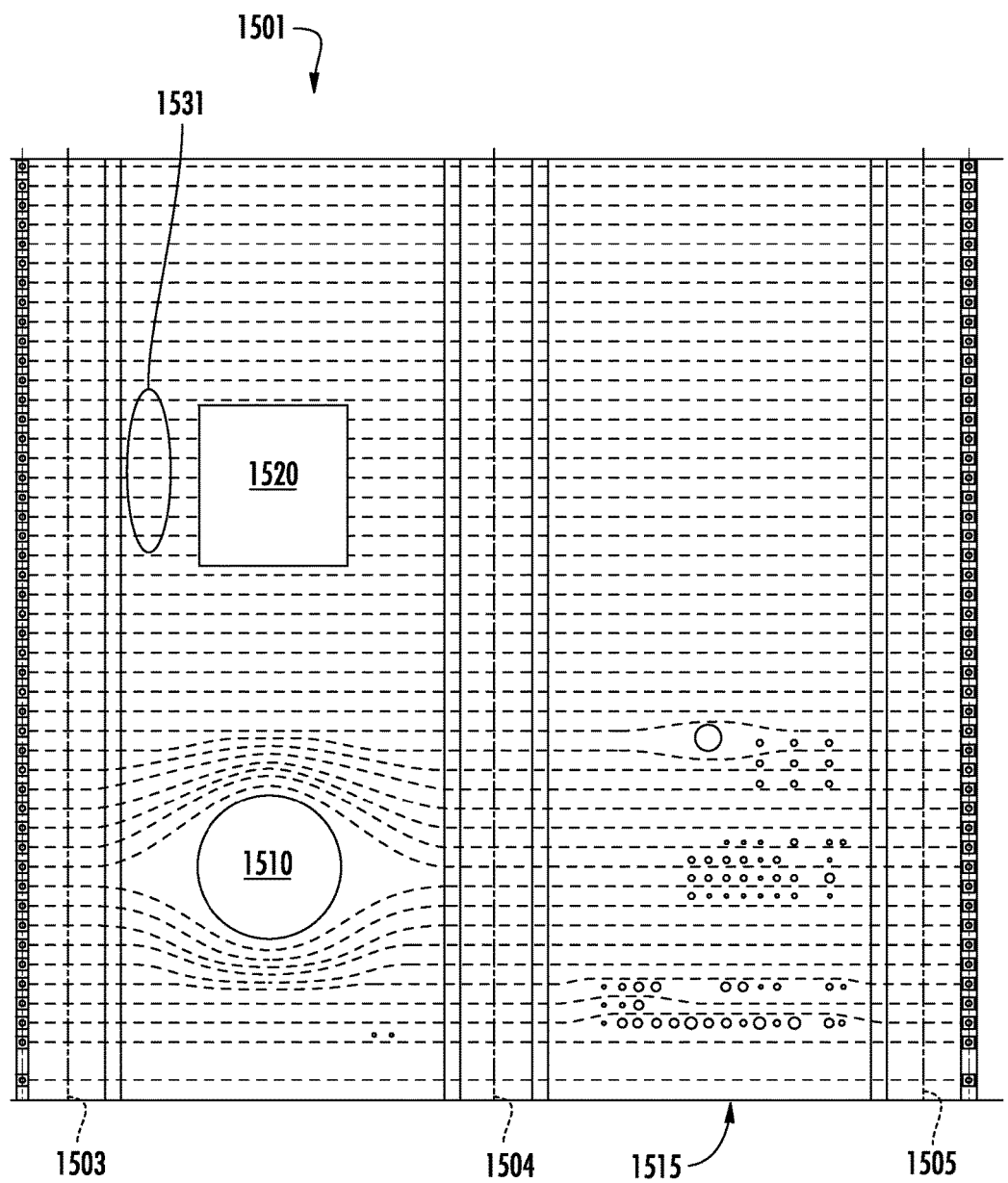
FIG. 15B shows a second set of horizontal tendons in a nuclear power plant containment building.

As is clear from FIGS. 15A and 15B, the stresses developed by an individual tendon is complex, e.g., in order to release the horizontal tendons for the temporary construction opening 1520 in bay 34, tension on tendons for bay 23 and bay 45 are also affected.

Since the tendons above and below the temporary construction opening 1520 were not detensioned, the loads on tendons immediately above and below the temporary construction opening 1520 were probably increased due to the relaxation of the compression on the band through the opening. Large gradients could develop in the strain between adjacent tensioned and untensioned tendons, producing large shear forces. Moreover, since the tendons were fully released in series, there could be transient differential stresses within the concrete.

It is not shown in FIG. 15A and FIG. 15B, but the 42H tendons connect to the 64H tendons at buttress 4, and they connect to the 62H tendons at buttress 2. This is better visualized by the buttress plan view on page 29 of the Progress Energy presentation, which is not reproduced herein. The combined 42H, 64H, and 62H tendons form a complete hoop around the containment building with anchors at buttresses 2, 4, and 6. Likewise, the 53H tendons connect to the 51H tendons at buttress 5, and they connect to the 31H tendons at buttress 3. The combined 53H, 51H, and 31H tendons form a complete hoop around the containment building with anchors at buttresses 1, 3, and 5.

When things are in the normal state, the horizontal forces on buttress 4 are balanced by the tension on tendon 42H pulling CW and the tension of tendon 64H pulling CCW. The horizontal forces on buttress 3 are balanced by the tension of tendon 53H pulling CCW and the tension of tendon 31H pulling CW.

By releasing the 8 42H tendons 1530, at buttresses 2 and 4, the horizontal forces on buttresses 2 and 4 become unbalanced and buttresses 2 and 4 must deflect to accommodate the unbalanced horizontal forces. Likewise, by releasing the 9 53H tendons 1531, at buttresses 3 and 5, the horizontal forces on buttresses 3 and 5 become unbalanced and buttresses 3 and 5 must deflect to accommodate the unbalanced horizontal forces. The deflections of the buttresses in turn reduce the tension on the companion tendons that complete each hoop. Moreover, the unbalance reduced the radial force of the buttresses pushing the containment wall inward, so the buttresses, and wall, also deflect outward radially.

Releasing the tendons to cut the temporary construction opening 1520 in bay 34 caused the loads to redistribute throughout the entire containment building-including horizontal bending loads on the buttresses.

According to the Progress Energy presentation, the horizontal tendons were designed to be loaded to 1,635 kips (1,635,000 lbf). The net result is that in the detensioned mode, buttresses number 2 and 4 experienced 8×1,635=13,080 kips, or 13,080,000 lbf of unbalanced horizontal force bending the buttress, and buttress number 3 and 5 experienced 9×1, 635=14, 715 kips, or 14,715,000 lbf of unbalanced horizontal force bending the buttress.

From the lengthy analysis, by the top engineering experts in the industry, described in the BACKGROUND, it is clear that even after the first failure brought attention to the complexity of the detensioning and retensioning operation it was still not understood well enough to avoid another failure during subsequent retensioning.

It is noteworthy that during retensioning on Mar. 14, 2011, strain gages and acoustical emissions were used to monitor the operation. According to the reports, there were no indications of anomalies prior to strain gages failing and active acoustic emissions for about 20 minutes. Clearly, the instrumentation was totally inadequate to prevent another delamination in bay 5-6. On Jul. 26, 2011, another delamination was detected when an area of concrete fell from bay 1-2, i.e., there was no instrumentation warning.

The incidents at Turkey Point and Crystal River, and the absence of a definitive answer as to how to prevent similar occurrences in the future, are sure to cause concerns for the next nuclear power plant that needs to cut a temporary construction opening in the containment building or dome. The incidents are also likely to be of concern for the Light Water Reactor Sustainability Program to extend the operating licenses for nuclear power plants beyond the current 60 year retirement.

If prior to detensioning the tendons, retroreflector targets 1440, 1441 had been anchored to the wall 1400 and buttresses (not shown), and EDM instruments (not shown) had been used to measure the distances along at least rays 1450A, 1450B 1450C to retroreflector target 1440 and along at least rays 1451A, 1451B, 1451C to retroreflector target 1441, and to the retroreflector targets on the buttresses, the three-dimensional coordinates of cardinal points could have been measured with very high accuracy. Measurement procedures and data analysis could be similar to those described in FIGS. 5-7 mutatis mutandis.

It will be understood that retroreflector targets 1440, 1441 are shown for illustration only. Based on engineering experience, a finite element model, and a detensioning plan, additional retroreflector targets, and instruments, would need to be added. In one embodiment the retroreflector targets and instruments may be arranged as shown in FIG. 9. At a minimum, buttresses 2-5 1502, 1503, 1504, 1505 would need to be modeled and measured. While the retroreflector targets 1440, 1441 are illustrated as being on the outer wall 1425, they could also be located on the inner wall 1430 to measure differences in motion between the inside and outside of the wall 1400 which would measure shear between the inside and outside and delamination cracks opening voids in the wall.

By comparing the measured three dimensional coordinates of the cardinal points with predictions as the tendons were released, or retensioned, and by looking at differential motions between cardinal points 1440, 1441 and determining the three dimensional strain—with accuracies in the order of microstrains-anomalies could be detected before the concrete failed and cracked. The detensioning process could have been halted in the early stages and the loss of the entire multi-billion dollar nuclear plant could possibly have been avoided.

As to the delamination of the domes at Turkey Point and Crystal River, it will be recognized in light of the disclosure herein that a similar measurement architecture could possibly have prevented those failures.

As to the Prestressed Concrete Containment Vessel Model, it will be recognized in light of the disclosure herein that measurements similar to those shown in FIG. 9 could produce additional useful data to confirm the finite element models, and possibly predict the location and time of failure.

In all of the examples, it will be recognized that the number and location of the instruments and targets shown is merely illustrative and the number and location of instruments and targets will be selected for the desired parameters being measured.

It will be recognized that the same principles of symmetry, linearity, hysteresis, creep, damping coefficient, fidelity to a finite element model, etc., as described for civil structures; and measurements of large pressure vessels, such as, but not limited to, boilers, receivers, storage tanks, ships, buoyant structures, reservoirs, vacuum chambers, spacecraft, and the like; also apply to measurements of prestressed concrete undergoing changes in tendon tensioning. It will also be recognized that measurements are not limited to single purposes, but can be used for at least all of the purposes described hereinabove. For example, measurements initially made for post-tensioning may be used for long-term structural health monitoring.

The description, drawings, and preferred embodiments serve to illustrate the invention, and are not to be construed as limitations of the invention, which is defined by the appended claims. It will be clear to those skilled in the art that modifications may be made without departing from the spirit of the invention.

What is claimed is:

1. A method for post-tensioning a concrete structure with steps comprising:
   (a) programming a finite element model of the concrete structure, which when executed by a processor predicts coordinates of a plurality of points on the concrete structure as a function of a plurality of tensions applied to a corresponding plurality of tendons within the concrete structure;
   (b) developing a post-tensioning plan for applying the plurality of tensions, wherein the post-tensioning plan is a written document that specifies an order in which the plurality of tendons are tensioned and a tensioning force to be applied to each of the plurality of tendons;
   (c) identifying a plurality of cardinal points from the plurality of points on the concrete structure, wherein the identifying is based at least in part on the finite element model, the post-tensioning plan, the predicted coordinates of the plurality of cardinal points, and engineering experience;
   (d) attaching a plurality of retroreflectors to the concrete structure at locations corresponding to the plurality of cardinal points;
   (e) measuring at least a first range from a first electronic distance measurement instrument to a first cardinal point, a second range from a second electronic distance measurement instrument to the first cardinal point, and a third range from a third electronic distance measurement instrument to the first cardinal point, wherein
   the first electronic distance measurement instrument is at a first location, the second electronic distance measurement instrument is at a second location, the third electronic distance measurement instrument is at a third location, and
   the first location, the second location, and the third location are three different locations;
   (f) storing at least the first, second, and third ranges;
   (g) computing a first three-dimensional coordinate of the first cardinal point, based at least in part on the first, second, and third ranges;

(h) applying a first tensioning force to a first of the plurality of tendons as specified by the post-tensioning plan;

(i) measuring at least a fourth range from the first electronic distance measurement instrument to the first cardinal point, a fifth range from the second electronic distance measurement instrument to the first cardinal point, and a sixth range from the third electronic distance measurement instrument to the first cardinal point;

(j) storing the fourth, fifth, and sixth ranges;

(k) computing a second three-dimensional coordinate of the first cardinal point, based at least in part on the fourth, fifth, and sixth ranges;

(l) modifying the post-tensioning plan based at least in part on the finite element model, the applied first tensioning force, the first three-dimensional coordinate, the second three-dimensional coordinate, and the engineering experience; and (m) applying a second tensioning force to a second of the plurality of tendons as specified by the modified post-tensioning plan.

2. The method of claim 1 wherein the modifying is selected from the group consisting of halting execution of the post-tensioning plan, modifying the order in which the plurality of tendons are tensioned, and modifying the tensioning force to be applied to each of the plurality of tendons.

3. The method of claim 1 wherein the programming of the finite element model is modified based at least in part on the finite element model, the applied first tensioning force, the first three-dimensional coordinate, the second three-dimensional coordinate, and the engineering experience.

4. The method of claim 1 wherein the engineering experience includes general factors based on Hooke's law, crack behavior, elastic limits, hysteresis, smooth functions, harmonic analysis, creep, damping coefficient, or symmetry.

5. The method of claim 1 wherein the engineering experience includes factors specific to the concrete structure based on history of accidents, history of floods, history of earthquakes, history of fire, seasonal weather conditions, industry and government standards, regulatory requirements, lessons learned from previous projects in the industry, contractor performance history, level of confidence in quality control, level of confidence in the finite element model, complexity and uniqueness of the design, confidence in assumptions made, test results, consequences of a failure, litigation potential, establishment of liability, safety concerns for the workers and final users, schedule, cost, weather conditions, preservation of personal and company reputation, demonstration of understanding to convince others, or prototype evaluation.

* * * * *